United States Patent
Thomas et al.

(10) Patent No.: US 6,855,719 B1
(45) Date of Patent: Feb. 15, 2005

(54) IMIDAZO[1,2-A]PYRIDINE AND PYRAZOLO [2,3-A]PYRIDINE DERIVATIVES

(75) Inventors: Andrew Peter Thomas, Macclesfield (GB); Gloria Anne Breault, Macclesfield (GB); John Franklin Beattie, Macclesfield (GB); Phillip John Jewsbury, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/069,019

(22) PCT Filed: Aug. 15, 2000

(86) PCT No.: PCT/GB00/03139

§ 371 (c)(1),
(2), (4) Date: Feb. 21, 2002

(87) PCT Pub. No.: WO01/14375

PCT Pub. Date: Mar. 1, 2001

(30) Foreign Application Priority Data

Aug. 21, 1999 (GB) .............................................. 9919778

(51) Int. Cl.⁷ .................... C07D 471/04; A61K 31/437; A61P 35/00
(52) U.S. Cl. ....................... 514/269; 514/272; 544/321; 544/331
(58) Field of Search ................................ 544/321, 331; 514/269, 272

(56) References Cited

U.S. PATENT DOCUMENTS

| | | | |
|---|---|---|---|
| 4,983,608 A | 1/1991 | Effland et al. | 544/319 |
| 5,516,775 A | 5/1996 | Zimmermann et al. | 514/275 |
| 5,521,184 A | 5/1996 | Zimmermann | 514/252 |
| 5,610,303 A | 3/1997 | Kimura et al. | 544/253 |
| 5,739,143 A | 4/1998 | Adams et al. | 544/122 |
| 5,859,041 A | 1/1999 | Liverton et al. | 544/298 |

FOREIGN PATENT DOCUMENTS

| | | |
|---|---|---|
| CA | 2231765 | 9/1998 |
| EP | 0 135 472 | 3/1985 |
| EP | 0 363 002 | 4/1990 |
| EP | 0 379 806 B1 | 8/1990 |
| EP | 0 564 409 A | 10/1993 |
| EP | 0 945 433 A1 | 9/1999 |
| EP | 0 945 443 A1 | 9/1999 |
| WO | 91/18887 | 12/1991 |
| WO | 92/20642 | 11/1992 |
| WO | 95/09847 | 4/1995 |
| WO | 95/09851 | 4/1995 |
| WO | 95/09852 | 4/1995 |
| WO | 95/09853 | 4/1995 |
| WO | 95/15952 | 6/1995 |
| WO | 96/05177 | 2/1996 |
| WO | 96/28427 | 9/1996 |
| WO | 96/40143 | 12/1996 |
| WO | 97/19065 | 5/1997 |
| WO | 97/35856 | 10/1997 |
| WO | 97/40017 | 10/1997 |
| WO | 97/44326 | 11/1997 |
| WO | 97/47618 | 12/1997 |
| WO | 98/11095 | 3/1998 |
| WO | 98/16230 | 4/1998 |
| WO | 98/18782 | 5/1998 |
| WO | 98/25619 | 6/1998 |
| WO | 98/33798 | 8/1998 |
| WO | 98/41512 | 9/1998 |
| WO | 98/54093 | 12/1998 |

(List continued on next page.)

OTHER PUBLICATIONS

Donnellan et al., FASEB Journal, 13, 773–777, 1999.*

Ghosh, 2,4–Bis(arylamino)–6–methylpyrimidines as an antimicrobial agents, Chemical Abstract No. 97712f, vol. 95, 1981, pp. 648.

Schmidt et al.; "A Convenient Synthesis of 2–substituted 4–Amino–5–pyrimidinecarbonitriles"; J. Heterocycle Chem., 1997, vol. 24, No. 5, pp. 1305–1307.

Zimmeramann et al., "Phenylamino–Pyrimidine (PAP) Derivatives: A New Class of Potent and Selective Inhibitors of Protein Kinase C (PKC)", Archiv der Pharmazie, de, VCH, Verlagsgesellschaft MBH, Weinheim, 329 (7), 1996, 371–376.

(List continued on next page.)

*Primary Examiner*—Venkataraman Balasubramanian
(74) *Attorney, Agent, or Firm*—Morgan, Lewis & Bockius LLP

(57) ABSTRACT

A compound of formula (I) wherein Ring A is imidazol[1, 2a]pyrid-3-yl or pyrazolo[2,3a]pyrid-3-yl; $R^2$ is as defined within; m is 0–5; wherein the values of $R^2$ may be the same or different; $R^1$ is as defined within; n is 0 to 2, wherein the values of $R^1$ may be the same or different; Ring B is phenyl or phenyl fused to a $C_{5-7}$cycloalkyl ring; $R^3$ is as defined within; p is 0–4; wherein the values of $R^3$ may be the same or different; $R^4$ is as defined within; q is 0–2; wherein the values of $R^4$ may be the same or different; and wherein $p+q \leq 5$; or a pharmaceutically acceptable salt or an in vivo hydrolyzable ester thereof is described. The use of compounds of formula (I) in the inhibition of cell cycle kinases CDK2, CDK4, and CDK6 are also described. Pharmaceutical compositions, methods and processes for preparation of compounds of formula (I) are detailed.

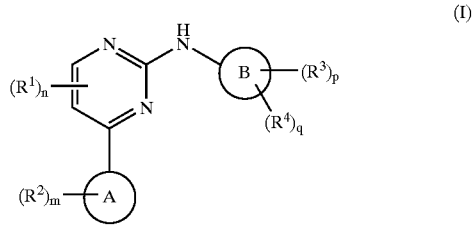

(I)

12 Claims, No Drawings

FOREIGN PATENT DOCUMENTS

| | | |
|---|---|---|
| WO | 98/56788 | 12/1998 |
| WO | 99/01136 | 1/1999 |
| WO | 99/32121 | 1/1999 |
| WO | 99/18096 | 4/1999 |
| WO | 99/18942 | 4/1999 |
| WO | 99/31073 | 6/1999 |
| WO | 99/41253 | 8/1999 |
| WO | 99/42153 | 8/1999 |
| WO | 99/50250 | 10/1999 |
| WO | 99/50251 | 10/1999 |
| WO | 00/12485 | 3/2000 |
| WO | 00/12486 | 3/2000 |
| WO | 00/17202 | 3/2000 |
| WO | 00/17203 | 3/2000 |
| WO | 00/21926 | 4/2000 |
| WO | 00/25780 | 5/2000 |
| WO | 00/26209 | 5/2000 |
| WO | 00/39101 | 6/2000 |
| WO | 00/44750 | 8/2000 |
| WO | 00/49018 | 8/2000 |
| WO | 00/53595 | 9/2000 |
| WO | 00/55161 | 9/2000 |
| WO | 00/59892 | 10/2000 |
| WO | 00/78731 A1 | 12/2000 |
| WO | 01/29009 A1 | 4/2001 |
| WO | 01/30778 A1 | 5/2001 |
| WO | 01/37835 A1 | 5/2001 |
| WO | 01/47897 A1 | 5/2001 |
| WO | 01/47921 A1 | 5/2001 |
| WO | 01/60816 A1 | 8/2001 |
| WO | 01/64653 A1 | 9/2001 |
| WO | 01/64654 A1 | 9/2001 |
| WO | 01/64655 A1 | 9/2001 |
| WO | 01/64656 A1 | 9/2001 |
| WO | 01/72717 A1 | 10/2001 |
| WO | 02/04429 A1 | 1/2002 |
| WO | 02/20512 A1 | 3/2002 |
| WO | 02/066481 A1 | 8/2002 |
| WO | 02/096887 A1 | 12/2002 |

OTHER PUBLICATIONS

Boschelli et al., "Synthesis and Tyrosine Kinase Inhibitory Activity of a Series of 2–Amino–8H–pyrido[2,3–d]pyrimidines: Identification of Potent, Selective Platelet–Derived Growth Factor Receipt Tyrosine Kianse Inhibitors", J Med. Chem. 41(22), 1998, 4365–4377.

Deady et all, "Reactions of some Quinazoline Compounds with Ethoxymethylenemalonic Acid Deriviatives", J Heterocycle Chem, 26(1), 1989, pp. 161–168.

El–Kerdawy et al.; 2,4–Bis(Substituted)–5–Nitropyrimidnes of Expected Diuretic Action; Egypt J. Chem. vol. 29, No. 2, 1986, pp. 247–251.

Fiziol Akt Veshchestva, 1975, vol. 7, pp. 68–72.

Ghosh et al.; 2,4–Bis(arylamino)–5–methylpyrimidines as Antimicrobial Agents; ; J. Med. Chem., 1967, vol. 10, No. 5, pp. 974–975.

* cited by examiner

IMIDAZO[1,2-A]PYRIDINE AND PYRAZOLO [2,3-A]PYRIDINE DERIVATIVES

The invention relates to pyrimidine derivatives, or pharmaceutically acceptable salts or in vivo hydrolysable esters thereof, which possess cell-cycle inhibitory activity and are accordingly useful for their anti-cell-proliferation (such as anti-cancer) activity add are therefore useful in methods of treatment of the human or animal body. The invention also relates to processes for the manufacture of said pyrimidine derivatives, to pharmaceutical compositions containing them and to their use in the manufacture of medicaments of use in the production of an anti-cell-proliferation effect in a warm-blooded animal such as man.

A family of intracellular proteins called cyclins play a central role in the cell cycle. The synthesis and degradation of cyclins is tightly controlled such that their level of expression fluctuates during the cell cycle. Cyclins bind to cyclin-dependent serine/threonine kinases (CDKs) and this association is essential for CDK (such as CDK1, CDK2, CDK4 and/or in CDK6) activity within the cell. Although the precise details of how each of these factors combine to regulate CDK activity is poorly understood the balance between the two dictates whether or not the cell will progress through the cell cycle.

The recent convergence of oncogene and tumour suppressor gene research has identified regulation of entry into the cell cycle as a key control point of mitogenesis in tumours. Moreover, CDKs appear to be downstream of a number of oncogene signalling pathways. Disregulation of CDK activity by upregulation of cyclins and/or deletion of endogenous inhibitors appears to be an important axis between mitogenic signalling pathways and proliferation of tumour cells.

Accordingly it has been recognised that an inhibitor of cell cycle kinases, particularly inhibitors of CDK2, CDK4 and/or CDK6 (which operate at the S-phase, G1-S and G1-S phase respectively) should be of value as a selective inhibitor of cell proliferation, such as growth of mammalian cancer cells.

The present invention is based on the discovery that certain pyrimidine compounds surprisingly inhibit the effects of cell cycle kinases showing selectivity for CDK2, CDK4 and CDK6, and thus possess anti-cell-proliferation properties. Such properties are expected to be of value in the treatment of disease states associated with aberrant cell cycles and cell proliferation such as cancers (solid tumours and leukemias), fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation.

Accordingly, the present invention provides a compound of formula (I):

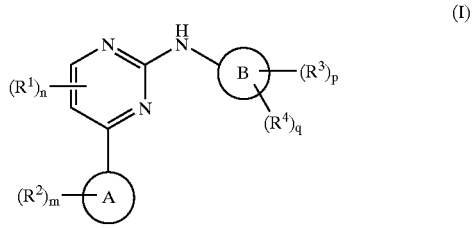

(I)

wherein:
Ring A is imidazo[1,2a]pyrid-3-yl or pyrazolo[2,3a]pyrid-3-yl;
$R^2$ is attached to a ring carbon and is selected from halo, nitro, cyano, hydroxy, trifluoromethyl, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N-($C_{1-6}$alkyl)amino, N,N-($C_{1-6}$alkyl)$_2$ amino, $C_{1-6}$alkanoylamino, N-($C_{1-6}$alkyl)carbamoyl, N,N-($C_{1-6}$alkyl)$_2$carbamoyl, $C_{1-6}$alkylS(O)$_a$ wherein a is 0 to 2, $C_{1-6}$alkoxycarbonyl, N-($C_{1-6}$alkyl)sulphamoyl, N,N-($C_{1-6}$alkyl)$_2$sulphamoyl, phenyl heterocyclic group, phenylthio or (heterocyclic group)thio; wherein any $C_{1-6}$alkyl, $C_{2-6}$alkenyl, $C_{2-6}$alkynyl, phenyl or heterocyclic group may be optionally substituted on carbon by one or more G; and wherein if said heterocyclic group contains an —NH— moiety that nitrogen may be optionally substituted by a group selected from Q;
m is (0-5; wherein the values of $R^2$ may be the same or different;
$R^1$ is halo, nitro, cyano, hydroxy, trifluoromethyl, trifluoromethoxy, amino, carboxy, carbamoyl, mercapto, sulphamoyl, $C_{1-3}$alkyl, $C_{2-3}$alkenyl, $C_{2-3}$alkynyl, $C_{1-3}$alkoxy, $C_{1-3}$alkanoyl, N-($C_{1-3}$alkyl)amino, N,N-($C_{1-2}$alkyl)$_2$amino, $C_{1-3}$alkanoylamino, N-($C_{1-2}$alkyl)carbamoyl, N,N-($C_{1-2}$alkyl)$_2$carbamoyl, $C_{1-3}$alkylS(O)$_a$ wherein a is 0 to 2, N-($C_{1-3}$alkyl)sulphamoyl or N,N-($C_{1-3}$alkyl)$_2$sulphamoyl; wherein any $C_{1-2}$alkyl, $C_{1-3}$alkyl, $C_{2-3}$alkenyl or $C_{2-3}$alkynyl may be optionally substituted on carbon by one or more J;
n is 0 to 2, wherein the values of $R^1$ may be the same or different;
Ring B is phenyl or phenyl fused to a $C_{5-7}$cycloalkyl ring;
$R^3$ is halo, nitro, cyano, hydroxy, amino, carboxy, carbamoyl, mercapto, sulphamoyl, $C_{2-6}$alkenyl or $C_{2-6}$alkynyl;
p is 0–4; wherein the values of $R^3$ may be the same or different;
$R^4$ is a group A—E—; wherein
A is selected from $C_{1-6}$alkyl, phenyl, a heterocyclic group, $C_{3-8}$cycloalkyl, phenyl$C_{1-6}$alkyl, (heterocyclic group)$C_{1-6}$alkyl or $C_{3-8}$cycloalkyl$C_{1-6}$cycloalkyl; which $C_{1-6}$alkyl, phenyl, a heterocyclic group, $C_{3-8}$cycloalkyl, phenyl$C_{1-6}$alkyl, (heterocyclic group)$C_{1-6}$alkyl or $C_{3-8}$cycloalkyl$C_{1-6}$cycloalkyl may be optionally substituted on carbon by one or more D; and wherein if said heterocyclic group contains an —NH— moiety that nitrogen may be optionally substituted by a group selected from R;
E is a direct bond or —O—, —C(O)—, —OC(O, —C(O)O—, —N($R^a$)C(O)—, —C(O)N($R^a$)—, —N($R^a$)—, —S(O)$_r$, —SO$_2$N($R^a$)— or —N($R^a$)SO$_2$—; wherein $R^a$ is hydrogen or $C_{1-6}$alkyl optionally substituted by one or more D and r is 0–2;
D is independently selected from oxo, halo, nitro, cyano, hydroxy, trifluoromethyl, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N-($C_{1-6}$alkyl)amino, N,N-($C_{1-6}$alkyl)$_2$ amino, $C_{1-6}$alkanoylamino, N-($C_{1-6}$alkyl)carbamoyl, N,N-($C_{1-6}$alkyl)$_2$carbamoyl, $C_{1-6}$alkylS(O)$_a$ wherein a is 0 to 2, $C_{1-6}$alkoxycarbonyl, C$_{1-6}$alkoxycarbonylamino, benzyloxycarbonylamino, N-(C$_{1-6}$alkyl)sulphamoyl and N,N-(C$_{1-6}$alkyl)$_2$ sulphamoyl; wherein any C$_{1-6}$alkyl, C$_{2-6}$alkenyl, C$_{2-6}$alkynyl or phenyl may be optionally substituted on carbon by one or more K;

q is −2; wherein the values of R$^4$ may be the same or different; and wherein p+q≦5;

G, J and K are independently selected from halo, nitro, cyano, hydroxy, trifluoromethoxy, trifluoromethyl, amino, carboxy, carbamoyl, mercapto, sulphamoyl, methyl, ethyl methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl ethoxycarbonyl, N-methylsulphamoyl, N-ethylsulphamoyl N,N-dimethylsulphamoyl, N,N-diethylsulphamoyl or N-methyl-N-ethylsulphamoyl; and Q and R are independently selected from C$_{1-4}$alkyl, C$_{1-4}$alkanoyl, C$_{1-4}$alkylsulphonyl, C$_{1-4}$alkoxycarbonyl, carbamoyl, N-(C$_{1-4}$alkyl)carbamoyl, N,N-(C$_{1-4}$alkyl) carbamoyl, benzyl, benzyloxycarbonyl, benzoyl and phenylsulphonyl;

or a pharmaceutically acceptable salt or an in vivo hydrolysable ester thereof.

For the avoidance of doubt, the phrase "wherein any C$_{1-6}$alkyl is optionally substituted" and other such phrases also includes the possibility of optional substitution on other groups that contain a C$_{1-6}$alkyl group, for example a C$_{1-6}$alkoxy, C$_{1-6}$alkanoyl, C$_{1-6}$alkanoyloxy, N-(C$_{1-6}$alkyl) amino, N,N-(C$_{1-6}$alkyl)$_2$amino, C$_{1-6}$alkanoylamino, N-(C$_{1-6}$ alkyl)carbamoyl, N,N-(C$_{1-6}$alkyl)$_2$carbamoyl, C$_{1-6}$alkylS (O)$_a$ wherein a is 0 to 2, C$_{1-6}$alkoxycarbonyl, C$_{1-6}$alkoxycarbonylamino, N-(C$_{1-6}$alkyl)sulphamoyl or a N,N-(C$_{1-6}$alkyl)$_2$sulphamoyl.

In this specification the term "alkyl" includes both straight and branched chain alkyl groups but references to individual alkyl groups such as "propyl" are specific for the straight chain version only. For example, "C$_{1-6}$alkyl" includes C$_{1-4}$alkyl, C$_{1-3}$alkyl, C$_{1-2}$alkyl, propyl, isopropyl and t-butyl. However, references to individual allyl groups such as 'propyl' are specific for the straight chained version only and references to individual branched chain alkyl groups such as 'isopropyl' are specific for the branched chain version only. A similar convention applies to other radicals, for example "phenylC$_{1-6}$alkyl" includes phenylC$_{1-4}$alkyl, benzyl, 1-phenylethyl and 2-phenylethyl. The term "halo" refers to fluoro, chloro, bromo and iodo.

Where optional substituents are chosen from "one or more" groups it is to be understood that this definition includes all substituents being chosen from one of the specified groups or the substituents being chosen from two or more of the specified groups.

A "heterocyclic group" is a saturated, partially saturated or unsaturated, mono or bicyclic ring containing 412 atoms of which at least one atom is chosen from nitrogen, sulphur or oxygen, which may, unless otherwise specified, be carbon or nitrogen linked, wherein a —CH$_2$— group can optionally be replaced by a —C(O)—, a ring nitrogen atom may optionally bear a C$_{1-6}$alkyl group and form a quaternary compound or a ring nitrogen and/or sulphur atom may be optionally oxidised to form the N-oxide and or the S-oxides. Examples and suitable values of the term "heterocyclic group" are morpholino, piperidyl, pyridyl, pyranyl, pyrrolyl, isothiazolyl, indolyl, quinolyl, thienyl, 1,3-benzodioxolyl, thiadiazolyl, piperazinyl, thiazolidinyl, pyrrolidinyl, thiomorpholino, pyrrolinyl, homopiperazinyl, 3,5-dioxapiperidinyl, tetrahydropyranyl, imidazolyl, pyrimidyl, pyrazinyl pyridazinyl, isoxazolyl, N-methylpyrrolyl, 4-pyridone, 1-isoquinolone, 2-pyrrolidone, 4-thiazolidone, pyridine-N-oxide and quinoline-N-oxide. Preferably a "heterocyclic group" is a saturated, partially saturated or unsaturated, mono or bicyclic ring containing 5 or 6 atoms of which at least one atom is chosen from nitrogen, sulphur or oxygen, which may, unless otherwise specified, be carbon or nitrogen linked, wherein a —CH$_2$— group can optionally be replaced by a —C(O)—, a ring nitrogen atom may optionally bear a C$_{1-6}$alkyl group and form a quaternary compound or a ring nitrogen and/or sulphur atom may be optionally oxidised to form the N-oxide and or the S-oxides.

A suitable value for phenyl fused to a C$_{5-7}$cycloalkyl ring is indanyl or tetralinyl.

An example of "C$_{1-6}$alkanoyloxy" is acetoxy. Examples of "C$_{1-6}$alkoxycarbonyl" include C$_{1-4}$alkoxycarbonyl, methoxycarbonyl, ethoxycarbonyl, n- and t-butoxycarbonyl. Examples of "C$_{1-4}$alkoxy" include C$_{1-3}$alkoxy, methoxy, ethoxy and propoxy. Examples of "C$_{1-6}$alkanoylamino" include C$_{1-3}$alkanoylamino, formamido, acetamido and propionylamino. Examples of "C$_{1-6}$alkylS(O)$_a$ wherein a is 0 to 2" include C$_{1-4}$alkylsulphonyl, C$_{1-3}$alkylS(O)$_a$, methylthio, ethylthio, methylsulphinyl, ethylsulphinyl mesyl and ethylsulphonyl. Examples of "C$_{1-6}$alkanoyl" include C$_{1-4}$alkanoyl, C$_{1-3}$alkanoyl propionyl and acetyl. Examples of "N-(C$_{1-6}$alkylamino" include N-(C$_{1-3}$alkyl)amino, methylamino and ethylamino. Examples of "N,N-(C$_{1-6}$alkyl)$_2$amino" include N,N-(C$_{1-2}$alkyl)$_2$amino, di-N-methylamino, di-N-ethyl)amino and N-ethyl-N-methylamino. Examples of "C$_{2-6}$alkenyl" are C$_{2-3}$alkenyl, vinyl allyl and 1-propenyl. Examples of "C$_{2-6}$alkynyl" are C$_{2-3}$alkynyl, ethynyl, 1-propynyl and 2-propynyl. Examples of "N-(C$_{1-6}$alkyl)sulphamoyl" are N-(C$_{1-3}$alkyl)sulphamoyl, N-(methyl)sulphamoyl and N-(ethyl)sulphamoyl. Examples of "N-(C$_{1-6}$alkyl)$_2$sulphamoyl" are N,N-(C$_{1-3}$alkyl)$_2$sulphamoyl, N,N-(dimethyl)sulphamoyl and N-(methyl)-N-(ethyl)sulphamoyl. Examples of "N-(C$_{1-6}$alkyl)carbamoyl" are N-(C$_{1-4}$alky)carbamoyl, N-(C$_{1-3}$alkyl)carbamoyl, methylaminocarbonyl and ethylaminocarbonyl. Examples of "N,N-(C$_{1-6}$alkyl)$_2$carbamoyl" are N,N-(C$_{1-4}$alkyl) carbamoyl, N,N-(C$_{1-2}$alkyl)$_2$carbamoyl, dimethylaminocarbonyl and methylethylaminocarbonyl. Examples of "C$_{5-7}$cycloalky ring" are cyclopropyl and cyclohexyl. Examples of "(heterocyclic group)C$_{1-6}$alkyl" include pyridylmethyl, 3-morpholinopropyl and 2-pyrimid-2-ylethyl. Examples of "(heterocyclic group)thio" include thienylthio and pyridylthio. Examples of "C$_{3-8}$cycloalky" include cyclopropyl and cyclohexyl. Examples of "C$_{3-8}$cycloalkylC$_{1-6}$cycloalkyl" include cyclopropylmethyl and 2-cyclohexylpropyl. Examples of "C$_{1-4}$alkoxycarbonylamimo" include methoxycarbonylamino and t-butoxycarbonylamino.

A suitable pharmaceutically acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

The compounds of the formula (I) may be administered in the form of a pro-drug which is broken down in the human or animal body to give a compound of the formula (I). Examples of pro-drugs include in vivo hydrolysable esters of a compound of the formula (a).

An in vivo hydrolysable ester of a compound of the formula (I) containing carboxy or hydroxy group is, for example, a pharmaceutically acceptable ester which is hydrolysed in the human or animal body to produce the parent acid or alcohol. Suitable pharmaceutically acceptable esters for carboxy include $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyloxyethyl and may be formed at any carboxy group in the compounds of this invention.

An in vivo hydrolysable ester of a compound of the formula (I) containing a hydroxy group includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxymethoxy and 2,2-dimethylpropionyloxy-methoxy. A selection of in vivo hydrolysable ester forming groups for hydroxy include alkanoyl, benzoyl phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. Examples of substituents on benzoyl include morpholino and piperazino linked from a ring nitrogen atom via a methylene group to the 3- or 4 position of the benzoyl ring.

Some compounds of the formula (I) may have chiral centres and/or geometric isomeric centres (E- and Z-isomers), and it is to be understood that the invention encompasses all such optical, diastereoisomers and geometric isomers that possess CDK inhibitory activity.

The invention relates to any and all tautomeric forms of the compounds of the formula (I) that possess CDK inhibitory activity.

It is also to be understood that certain compounds of the formula (I) can exist in solvated as well as unsolvated forms such as, for example, hydrated forms. It is to be understood that the invention encompasses all such solvated forms which possess CDK inhibitory activity.

In another aspect of the invention, there is provided a compound of formula (I) (as depicted above) wherein:

Ring A is imidazo[1,2a]pyrid-3-yl or pyrazolo[2,3a]pyrid-3-yl;

$R^2$ is attached to a ring carbon and is selected from halo, nitro, cyano, hydroxy, trifluoromethyl, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N-($C_{1-6}$alkyl)amino, N,N-($C_{1-6}$alkyl)$_2$ amino, $C_{1-6}$alkanoylamino, N-($C_{1-6}$alkyl)carbamoyl, N,N-($C_{1-6}$alkyl)$_2$carbamoyl, $C_{1-6}$alkylS(O)$_a$ wherein a is 0 to 2, $C_{1-6}$alkoxycarbonyl, N-($C_{1-6}$alkyl)sulphamoyl and N,N-($C_{1-6}$alkyl)$_2$sulphamoyl;

m is 0–5; wherein the values of $R^2$ may be the same or different;

$R^1$ is halo, nitro, cyano, hydroxy, trifluoromethyl, trifluoromethoxy, amino, carboxy, carbamoyl, mercapto, sulphamoyl $C_{1-3}$alkyl, $C_{2-3}$alkenyl, $C_{2-3}$alkynyl, $C_{1-3}$alkoxy, $C_{1-3}$alkanoyl, N-($C_{1-3}$alkyl) amino, N,N-($C_{1-2}$alkyl)$_2$amino, $C_{1-3}$alkanoylamino, N-($C_{1-3}$alkyl)carbamoyl, N,N-($C_{1-2}$alkyl)$_2$carbamoyl, $C_{1-3}$alkylS(O)$_a$ wherein a is 0 to 2, N-($C_{1-3}$alkyl) sulphamoyl or N,N-($C_{1-3}$alkyl)$_2$sulphamoyl;

n is 0 to 2, wherein the values of $R^1$ may be the same or different;

Ring B is phenyl or phenyl fused to a $C_{5-7}$cycloalkyl ring;

$R^3$ is halo, nitro, cyano, hydroxy, amino, carboxy, carbamoyl, mercapto, sulphamoyl, $C_{2-4}$alkenyl or $C_{2-6}$alkynyl;

p is 0–4; wherein the values of $R^1$ may be the same or different;

$R^4$ is a group A—E—; wherein

A is optionally substituted on carbon by one or more D and is selected from $C_{1-6}$alkyl, phenyl, a heterocyclic group, phenyl$C_1$alkyl or (heterocyclic group)$C_{1-6}$alkyl;

E is a direct bond or O—, —C(O)—, —OC(O)—, —C(O)O—, —N($R^a$)C(O)—, —C(O)N($R^a$)—, —N($R^a$)—, —S(O)$_r$—, —SO$_2$N($R^a$)— or —N($R^a$)SO$_2$—; wherein $R^a$ is hydrogen or $C_{1-6}$allyl optionally substituted by one or more D and r is 0–2;

D is independently selected from oxo, halo, nitro, cyano, hydroxy, trifluoromethyl, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N-($C_{1-6}$alkyl)amino, N,N-($C_{1-6}$alkyl)$_2$ amino, $C_{1-6}$alkanoylamino, N-($C_{1-6}$alkyl)carbamoyl, N,N-($C_{1-6}$alkyl)$_2$carbamoyl, $C_{1-6}$alkylS(O)$_a$ wherein a is 0 to 2, $C_{1-6}$alkoxycarbonyl, N-($C_{1-6}$alkyl)sulphamoyl and N,N-($C_{1-6}$alkyl)$_2$sulphamoyl; and q is 0–2; wherein the values of $R^4$ maybe the same or different; and wherein p+q≦5;

or a pharmaceutically acceptable salt or an in vivo hydrolysable ester thereof.

Preferred values of $R^1$, $R^2$, $R^3$, $R^4$, n, m, p, q, Ring A and Ring B are as follows. Such values may be used where appropriate with any of the definitions, claims or embodiments defined hereinbefore or hereinafter.

In one aspect of the invention preferably Ring A is imidazo[1,2a]pyrid-3-yl.

In another aspect of the invention preferably Ring A is pyrazolo[2,3a]pyrid-3-yl.

Preferably $R^2$ is attached to a ring carbon and is selected from halo, nitro, cyano, hydroxy, trifluoromethyl, trifluoromethoxy, amino, carboxy, carbamoyl, sulphamoyl $C_{1-3}$alkyl, $C_{2-3}$alkenyl, $C_{1-3}$alkoxy, $C_{1-3}$alkanoyl, $C_{1-3}$alkanoyloxy, N-($C_{1-3}$alkyl)amino, N,N-($C_{1-2}$alkyl)$_2$ amino, $C_{1-3}$alkanoylamino, N-($C_{1-3}$alkyl)carbamoyl, N,N-($C_{1-2}$alkyl)$_2$carbamoyl, $C_{1-3}$alkylS(O)$_a$ wherein a is 0 to 2, N-($C_{1-3}$alkyl)sulphamoyl and N,N-($C_{1-3}$alkyl)$_2$sulphamoyl.

More preferably $R^2$ is attached to a ring carbon and is $C_{1-3}$alkyl.

Particularly $R^2$ is attached to a ring carbon and is methyl.

In another aspect of the invention, preferably $R^2$ is attached to a ring carbon and is selected from halo, nitro, cyano, hydroxy, trifluoromethyl, trifluoromethoxy, amino, carboxy, carbamoyl mercapto, sulphamoyl, $C_{1-3}$alkyl, $C_{2-3}$alkenyl, $C_{2-3}$alkynyl $C_{1-3}$alkoxy, $C_{1-3}$alkanoyl, $C_{1-3}$alkanoyloxy, N-($C_{1-3}$alkyl)amino, N,N-($C_{1-3}$alky)$_2$ amino, $C_{1-3}$alkanoylamino, N-($C_{1-3}$alkyl)carbamoyl, N,N-($C_{1-3}$alkyl)$_2$carbamoyl, $C_{1-3}$alkylS(O), wherein a is 0 to 2, $C_{1-3}$alkoxycarbonyl, N-($C_{1-3}$alkyl)sulphamoyl, N,N-($C_{1-}$ ₃alkyl)₂sulphamoyl, phenyl, heterocyclic group, phenylthio or (heterocyclic group)thio; wherein any $C_{1-3}$alkyl, $C_{2-3}$alkenyl, $C_{2-3}$alkynyl, phenyl or heterocyclic group may be optionally substituted on carbon by one or more G; and wherein if said heterocyclic group contains an —NH— moiety that nitrogen may be optionally substituted by a group selected from Q.

In another aspect of the invention, more preferably $R^2$ is attached to a ring carbon and is selected from halo, cyano, $C_{1-6}$alkyl, $C_{1-6}$alkoxy, $C_{1-6}$alkylS(O)$_a$ wherein a is 0, phenyl, phenylthio or (heterocyclic group)thio; wherein any $C_1$alkyl, phenyl or heterocyclic group may be optionally substituted on carbon by one or more G; wherein G is selected from hydroxy and dimethylamino.

In another aspect of the invention, particularly $R^2$ is attached to a ring carbon and is selected from bromo, cyano, methyl, methoxy, ethylthio, 2-hydroxyethylthio, 2-dimethylaminoethylthio, phenyl, phenylthio or thien-2-ylthio.

In another aspect of the invention, more particularly $R^2$ is attached to a ring carbon and is selected from bromo, cyano, methyl, methoxy, ethylthio, 2-hydroxyethylthio or 2-dimethylaminoethylthio.

In another aspect of the invention, particularly preferred $R^2$ is attached to a ring carbon and is selected from 2-hydroxyethylthio.

In a further aspect of the invention, preferably $R^2$ is attached to a ring carbon and is selected from fluoro, chloro, bromo, cyano, methyl, methoxy, ethylthio, 2-hydroxyethylthio or 2-dimethylaminoethylthio.

Preferably m is 0–2; wherein the values of $R^2$ may be the same or different.

In one aspect of the invention preferably m is 0.

In another aspect of the invention preferably m is 1.

In a further aspect of the invention preferably m is 2; wherein the values of $R^2$ may be the same or different.

In a further aspect of the invention, preferably $R^2$ is attached to a ring carbon and is selected from fluoro, chloro, bromo, cyano, methyl, methoxy, ethylthio, 2-hydroxyethylthio or 2-dimethylaminoethylthiom and m is 0–2; wherein the values of $R^2$ may be the same or different.

Preferably $R^2$ is attached to a ring carbon and is selected from bromo, cyano, methyl, methoxy, ethylthio, 2-hydroxyethylthio or 2-dimethylaminoethylthio and m is 0–2; wherein the values of $R^2$ may be the same or different.

Preferably Ring A and $(R^2)_m$ together form imidazo[1,2a]pyrid-3-yl, pyrazolo[2,3a]pyrid-3-yl, 2-methylimidazo[1,2a]pyrid-3-yl, 2-methylpyrazolo[2,3a]pyrid-3-yl or 2,5-dimethylimidazo[1,2a]pyrid-3-yl.

In another aspect of the invention preferably Ring A and $(R^2)_m$ together form imidazo[1,2a]pyrid-3-yl, pyrazolo[2,3a]pyrid-3-yl, 2-methylimidazo[1,2a]pyrid-3-yl, 2-methylpyrazolo[2,3a]pyrid-3-yl, 2,5-dimethylimidazo[1,2a]pyrid-3-yl, 6-phenylimidazo[1,2a]pyrid-3-yl, 2-methyl-6-methoxyimidazo[1,2a]pyrid-3-yl, 5-bromoimidazo[1,2a]pyrid-3-yl, 5-phenylthioimidazo[1,2a]pyrid-3-yl, 5-ethylthioimidazo[1,2a]pyrid-3-yl, 52-hydroxyethylthio)imidazo[1,2a]pyrid-3-yl, 5-thien-2-ylthioimidazo[1,2a]pyrid-3-yl, 5-cyanoimidazo[1,2a]pyrid-3-yl or 5-(2-dimethylaminoethylthio)imidazo[1,2a]pyrid-3-yl.

In another aspect of the invention more preferably Ring A and $(R^2)_m$ together form imidazo[1,2a]pyrid-3-yl or 5-(2-hydroxyethylthio)imidazo[1,2a]pyrid-3-yl.

Preferably n is 0 or 1 and where n is 1 preferably $R^1$ is attached to the 5-position of the pyrimidine ring.

More preferably n is 0.

Preferably $R^1$ is halo or $C_{1-3}$alkylS(O)$_a$ wherein a is 0; wherein the $C_{1-3}$alkyl group may be optionally substituted on carbon by one or more J; wherein J is hydroxy.

More preferably $R^1$ is bromo or 2-hydroxyethylthio.

Particularly $R^1$ is bromo or 2-hydroxyethylthio and n is 0–1.

Preferably Ring B is phenyl or indanyl.

More preferably Ring B is phenyl or indan-5-yl.

Particularly Ring B is phenyl.

Preferably $R^3$ is halo or sulphamoyl.

More preferably $R^3$ is fluoro, chloro, bromo or sulphamoyl.

Particularly $R^3$ is chloro or sulphamoyl.

More particularly $R^3$ is sulphamoyl.

Preferably p is 0–2; wherein the values of $R^3$ may be the same or different.

In one aspect of the invention preferably p is 0.

In another aspect of the invention preferably p is 1.

In a further aspect of the invention preferably p is 2 wherein the values of $R^3$ may be the same or different.

Preferably $R^3$ is fluoro, chloro, bromo or sulphamoyl; and p is 1.

In a further aspect of the invention when Ring B is phenyl and p is 1, preferably $R^3$ is attached meta to the —NH— moiety of formula (I).

Preferably $R^a$ is hydrogen.

Preferably E is —NHSO₂—.

Preferably $R^4$ is a group A—E—; wherein
  A is optionally substituted on carbon by one or more D and is selected from $C_{1-4}$alkyl, phenyl, a heterocyclic group or phenyl$C_{1-4}$alkyl;
  E is a direct bond or —O—, —C(O)—, —N(R$^a$)C(O)—, —S(O)$_r$— or —N(R$^a$)SO₂—; wherein R$^a$ is hydrogen, methyl or ethyl and r is 0–2;
  D is oxo, cyano, hydroxy, amino, carboxy, carbamoyl, sulphamoyl, $C_{1-3}$alkyl, $C_{2-3}$alkenyl, $C_{2-3}$alkynyl, $C_{1-3}$alkoxy, $C_{1-3}$alkanoyl, N-($C_{1-3}$alkyl)amino, N,N-($C_{1-2}$alkyl)₂amino, $C_{1-3}$alkanoylamino, N—($C_{1-3}$alkyl)carbamoyl, N,N-($C_{1-2}$alkyl)₂carbamoyl, $C_{1-3}$alkylS(O)$_a$ wherein a is 0 to 2, N-($C_{1-3}$alkyl)sulphamoyl or N,N-($C_{1-3}$alkyl)₂sulphamoyl.

More preferably $R^4$ is a group A—E—; wherein
  A is optionally substituted on carbon by one or more D and is selected from $C_{1-4}$alkyl, phenyl, a heterocyclic group or phenyl$C_{1-4}$alkyl;
  E is a direct bond or —O—, —C(O)— or —S(O)$_r$—; wherein r is 0–2;
  D is hydroxy or N,N-($C_{1-2}$alkyl)₂amino.

Particularly $R^4$ is methyl, ethyl, methoxy, methylthio, mesyl, acetyl, 3-N,N-dimethylamino-2-hydroxypropoxy, 2-N,N-diethylaminoethoxy, benzyloxy, anilinosulphonyl, pyrimidin-2-ylaminosulphonyl, phenoxy, 3,5-dioxapiperidin-1-ylsulphonyl.

In another aspect of the invention, preferably $R^4$ is a group A—E—; wherein
  A is selected from $C_{1-4}$alkyl, phenyl, a heterocyclic group, $C_{3-8}$cycloalkyl, phenyl$C_{1-6}$alkyl, (heterocyclic group)$C_{1-6}$alkyl or $C_{3-8}$-cycloalkyl$C_{1-6}$cycloalkyl; which $C_{1-6}$alkyl, phenyl, a heterocyclic group, $C_{3-8}$cycloalkyl, phenyl$C_{1-6}$alkyl, (heterocyclic group)$C_{1-6}$alkyl or $C_{3-8}$cycloalkyl$C_{1-6}$cycloalkyl may be optionally substituted on carbon by one or more D; and wherein if said heterocyclic group contains an —NH— moiety that nitrogen may be optionally substituted by a group selected from R;
  E is a direct bond or —O—, —C(O)—, —N(R$^a$)C(O)—, —S(O)$_r$— or —N(R$^a$)SO₂—; wherein R$^a$ is hydrogen, or $C_{1-6}$alkyl and r is 0–2;

D is independently selected from hydroxy, amino, $C_{1-6}$alkoxy, N-($C_{1-6}$alkyl)amino, N,N-($C_{1-6}$alkyl)$_2$ amino, $C_{1-6}$alkoxycarbonylamino or benzyloxycarbonylamino; wherein any $C_{1-6}$alkyl may be optionally substituted on carbon by one or more K;

K is selected from hydroxy or diethylamino; and

R is $C_{1-4}$alkyl.

In another aspect of the invention, more preferably $R^4$ is a group A—E—; wherein A is selected from methyl, ethyl, propyl, pentyl, phenyl, pyrimidyl, 3,5-dioxapiperidin-1-yl, cyclopropyl, benzyl, pyrrolidin-1-ylethyl, piperidin-1-ylethyl, pyrrolidin-2-ylethyl, 3-(2-oxo-pyrrolidin-1-yl)propyl, 3-imidazol-1-ylpropyl, 2-morpholinoethyl, 3-morpholinopropyl, 2-imidazol-4-ylethyl, 2-piperazin-1-ylethyl, 3-piperazin-1-ylpropyl or cyclopropylmethyl; wherein A may be optionally substituted on carbon by one or more D; and wherein pyrrolidin-2-yl, imidazol-4-yl or piperazin-1-yl may be optionally substituted on nitrogen by a group selected from R;

E is a direct bond or —O—, —C(O)—, —N($R^a$)C(O), —S(O)$_r$— or —N($R^a$)SO$_2$—; wherein $R^a$ is hydrogen or methyl and r is 0–2;

D is independently selected from hydroxy, amino, methoxy, methylamino, ethylamino, isopropylamino, N,N-dimethylamino, N,N-diethylamino, t-butoxycarbonylamino or benzyloxycarbonylamino; wherein any methyl, ethyl, isopropyl or t-butyl may be optionally substituted on carbon by one or more K;

K is selected from hydroxy or diethylamino; and

R is methyl.

In another aspect of the invention, particularly $R^4$ is methyl, ethyl, methoxy, methylthio, acetyl benzyloxy, mesyl, N,N-diethylaminoethoxy, 3-N,N-dimethylamino-2-hydroxypropoxy, phenoxy, N-methylcarbamoyl, N,N-dimethylcarbamoyl, N-(3-imidazol-1-ylpropyl)carbamoyl, N-[3-(2-oxo-pyrrolidin-1-yl)propyl]carbamoyl, 3,5-dioxapiperidin-1-ylsulphonyl, N-cyclopropylsulphamoyl, N-cyclopropylmethylsulphamoyl, anilinosulphonyl, N-pyrimidin-2-ylsulphamoyl, N-methylsulphamoyl, N-propylsulphamoyl, N-(2-methoxyethyl)sulphamoyl, N-(2-methylaminoethyl)sulphamoyl, N-(2-isopropylaminoethyl)sulphamoyl, N-(2-dimethylaminoethyl)sulphamoyl N-(2-diethylaminoethyl)sulphamoyl, N-[2-(hydroxyethylamino)ethyl]sulphamoyl, N-[2-(diethylaminoethyl)ethyl]sulphamoyl, N-(pyrrolidin-1-ylethyl)sulphamoyl, N-[2-(1-methylpyrrolidin-2-yl)ethyl]sulphamoyl, N-(2-piperidin-1-ylethyl)sulphamoyl, N-(2-piperazin-1-ylethyl)sulphamoyl, N-(2-morpholinoethyl) sulphamoyl, N-(2-imidazol-4-ylethyl)sulphamoyl, N-(3-hydroxypropyl)sulphamoyl, N-(2,3-dihydroxypropyl) sulphamoyl, N-(3-methoxypropyl)sulphamoyl, N-(3-aminopropyl)sulphamoyl, N-(3-methylaminopropyl) sulphamoyl, N-(3-dimethylaminopropyl)sulphamoyl, N-(3-diethylaminopropyl)sulphamoyl, N-(3-isopropylaminopropyl)sulphamoyl, N-(3-t-butoxycarbonylaminopropyl)sulphamoyl, N-(3-benzyloxycarbonylaminopropyl)sulphamoyl, N-[3-(2-oxopyrrolidin-1-yl)propyl]sulphamoyl, N-(3-morpholinopropyl)sulphamoyl, N-[3-(4-methylpiperazin-1-yl)propyl]sulphamoyl, N-(3-imidazol-1-ylpropyl) sulphamoyl or N-(5-hydroxypentyl)sulphamoyl.

In another aspect of the invention, more particularly $R^4$ is N-methylsulphamoyl, N-(2-methoxyethyl)sulphamoyl, N-(2-methylaminoethyl)sulphamoyl, N-(2-dimethylaminoethyl)sulphamoyl, N-(3-methoxypropyl) sulphamoyl, N-(3-dimethylaminopropyl)sulphamoyl or N-(3-isopropylaminopropyl)sulphamoyl.

Preferably $R^4$ is methyl, ethyl, methoxy, methylthio, acetyl, benzyloxy, mesyl, N,N-diethylaminoethoxy, 3-N,N-dimethylamino-2-hydroxypropoxy, phenoxy, N-methylcarbamoyl, N,N-dimethylcarbamoyl, N-(3-imidazol-1-ylpropyl)carbamoyl, N-[3-(2-oxo-pyrrolidin-1-yl)propyl]carbamoyl, 3,5-dioxapiperidin-1-ylsulphonyl, N-cyclopropylsulphamoyl, N-cyclopropylmethylsulphamoyl, anilinosulphonyl, N-pyrimidin-2-ylsulphamoyl, N-methylsulphamoyl, N-propylsulphamoyl, N-(2-methoxyethyl)sulphamoyl, N-(2-methylaminoethyl)sulphamoyl, N-(2-isopropylaminoethyl)sulphamoyl, N-(2-dimethylaminoethyl)sulphamoyl, N-(2-diethylaminoethyl) sulphamoyl, N-[2-(hydroxyethylamino)ethyl]sulphamoyl, N-[2-(diethylaminoethylethyl]sulphamoyl, N-(pyrrolidin-1-ylethyl)sulphamoyl, N-[2-(1-methylpyrrolidin-2-yl)ethyl] sulphamoyl, N-(2-piperidin-1-ylethyl)sulphamoyl, N-(2-piperazin-1-ylethyl)sulphamoyl, N-(2-morpholinoethyl) sulphamoyl, N-(2-imidazol-4-ylethyl)sulphamoyl, N-(3-hydroxypropyl)sulphamoyl, N-(2,3 dihydroxypropyl) sulphamoyl, N-(3-methoxypropyl)sulphamoyl, N-(3-aminopropyl)sulphamoyl, N-(3-methylaminopropyl) sulphamoyl, N-(3-dimethylaminopropyl)sulphamoyl, N-(3-diethylaminopropyl)sulphamoyl, N-(3-isopropylaminopropyl)sulphamoyl, N-(3-t-butoxycarbonylaminopropyl)sulphamoyl, N-(3-benzyloxycarbonylaminopropyl)sulphamoyl, N-[3-(2-oxopyrrolidin-1-yl)propyl]sulphamoyl, N-(3-morpholinopropyl)sulphamoyl, N-[3-(4-methylpiperazin-1-yl)propyl]sulphamoyl, N-(3-imidazol-1-ylpropyl) sulphamoyl or N-(5-hydroxypentyl)sulphamoyl; and q is 1.

Preferably q is 0–1.

In one aspect of the invention q is 0.

In another aspect of the invention q is 1.

In a further aspect of the invention when Ring B is phenyl and q is 1, preferably $R^4$ is attached para to the —NH— moiety of formula (I).

Preferably Ring B, $(R^3)_p$ $(R^4)_q$ and together form phenyl, 2-fluorophenyl, 3-fluorophenyl, 4-fluorophenyl, 2-chlorophenyl, 3-chlorophenyl, 4-chlorophenyl, 3-bromophenyl, 3-methylphenyl, 4-methylphenyl, 3-ethylphenyl, 3-methoxyphenyl, 4-methoxyphenyl, 3-methylthiophenyl, 4-methylthiophenyl, 4-mesylphenyl, 3-sulphamoylphenyl, 4-sulphamoylphenyl, 3-acetylphenyl, 3,4-dichlorophenyl, 3-chloro-4-fluorophenyl, 2-chloro-4-methylphenyl, 43-N,N-dimethylamino-2-hydroxypropoxy) phenyl, 4-benzyloxyphenyl, 4-anilinosulphonylphenyl, 4-(pyrimidin-2-ylsulphonyl)phenyl, 4-phenoxyphenyl, 4-(2-N,N-diethylaminoethoxy)phenyl, 4-(3,5-dioxapiperidin-1-ylsulphonyl)phenyl or indanyl.

In another aspect of the invention, more preferably Ring B, $(R^3)_p$ $(R^4)_q$ and together form phenyl, 2-chlorophenyl, 2-fluorophenyl, 3-fluorophenyl, 3-chlorophenyl, 3-bromophenyl, 3-methylphenyl, 3-methoxyphenyl, 3-methylthiophenyl, 3-acetylphenyl, 3-ethylphenyl, 3-sulphamoylphenyl, 4-fluorophenyl, 4-chlorophenyl, 4-methylphenyl, 4-methoxyphenyl, 4-sulphamoylphenyl, 3-methyl 4-sulphamoylphenyl, 4-(N-methylcarbamoyl) phenyl, 4-(N,N-dimethylcarbamoyl)phenyl, 4-methylthiophenyl, 4-mesylphenyl, 4N-methylsulphamoyl)phenyl, 4N-propylsulphamoyl) phenyl, 3-chloro-4-(N-propylsulphamoyl)phenyl, 4N,N-diethylaminoethoxy)phenyl, 4-benzyloxyphenyl, 4-phenoxyphenyl, 4-(N-cyclopropylsulphamoyl)phenyl, 4-(N-cyclopropylmethylsulphamoyl)phenyl, 4-(3,5- dioxapiperidin-1-ylsulphonyl)phenyl, 4-anilinosulphonylphenyl, 4-(N-pyrimidin-2-ylsulphamoyl) phenyl, 4-[N-(2-methoxyethyl)sulphamoyl]phenyl, 3-chloro-4[N-(2-methoxyethyl)sulphamoyl]phenyl, 3-methyl-4-[N-(2-methoxyethyl)sulphamoyl]phenyl, 4-[N-(3-diethylaminopropyl)sulphamoyl]phenyl, 4-{N-[2-(1-methylpyrrolidin-2-yl)ethyl]sulphamoyl]}phenyl, 3-chloro-4-fluorophenyl, 3,4-dichlorophenyl, 2-chloro-4-methylphenyl, 4-(3-N,N-dimethylamino-2-hydroxypropoxy)phenyl, 4-[N-(3-hydroxypropyl) sulphamoyl]phenyl, 4-{N-[3-(2-oxopyrrolidin-1-yl)propyl] sulphamoyl}phenyl, 4-[N-(5-hydroxypentyl)sulphamoyl] phenyl, 4-[N-(3-methoxypropyl)sulphamoyl]phenyl, indan-5-ylamino, 4-[N-(3-isopropylaminopropyl)sulphamoyl] phenyl, 4-[N-(2-isopropylaminoethyl)sulphamoyl]phenyl, 4-[N-(3-imidazol-1-ylpropyl)sulphamoyl]phenyl, 4-[N-(3-dimethylaminopropyl)sulphamoyl]phenyl, 4-[N-(3-morpholinopropyl)sulphamoyl]phenyl, 3-methyl-4[N-(3-morpholinopropyl)sulphamoyl]phenyl, 4-[N-(3-aminopropyl)sulphamoyl)phenyl, 4-{N-[2-hydroxyethylamino)ethyl]sulphamoyl}phenyl, 4-[N-(2-imidazol-4-ylethyl)sulphamoyl]phenyl, 4-[N-(3-methylaminopropyl)sulphamoyl]phenyl, 4-[N-(2-piperazin-1-ylethyl)sulphamoyl]phenyl, 4-[N-[3-(4-methylpiperazin-1-yl)propyl]sulphamoyl]phenyl, 4-[N-(2,3-dihydroxypropyl)sulphamoyl]phenyl, 4-[N-(3-imidazol-1-ylpropyl)carbamoyl]phenyl, 4-[N-[2-diethylaminoethyl) ethyl]sulphamoyl]phenyl, 4-[N-[3-(2-oxopyrrolidin-1-yl) propyl]carbamoyl]phenyl, 4-[N-(2-diethylaminoethyl) sulphamoyl]phenyl, 4-[N-(2-morpholinoethyl)sulphamoyl] phenyl, 3-methyl-4[N-(2-morpholinoethyl)sulphamoyl] phenyl, 4-[N-(pyrrolidin-1-ylethyl)sulphamoyl]phenyl, 4[N-(2-methylaminoethyl)sulphamoyl]phenyl, 4-[N-(2-piperidin-1-ylethyl)sulphamoyl]phenyl, 4-[N-(2-diethylaminoethyl)sulphamoyl]phenyl, 4-[N-(3-t-butoxycarbonylaminopropyl)sulphamoyl]phenyl, 4-[N-(3-benzyloxycarbonylaminopropyl)sulphamoyl]phenyl or 4-[N-(3-diethylaminopropyl)sulphamoyl]phenyl.

In another aspect of the invention, particularly Ring B, $(R^3)_p$ $(R^4)_q$ and together form 4-sulphamoylphenyl, 4-(N-methylsulphamoyl)phenyl, 4-[N-(2-methoxyethyl) sulphamoyl]phenyl, 4-[N-(3-methoxypropyl)sulphamoyl] phenyl, 4[N-(3-isopropylaminopropyl)sulphamoyl]phenyl, 4-[N-(3-dimethylaminopropyl)sulphamoyl]phenyl, 4-[N-(2-dimethylaminoethyl)sulphamoyl]phenyl or 4-[N-(2-methylaminoethyl)sulphamoyl]phenyl Therefore in one aspect of the invention, there is provided a compound of formula (I) as depicted above wherein:
  Ring A is imidazo[1,2a]pyrid-3-yl or pyrazolo[2,3a]pyrid-3-yl;
  $R^2$ is attached to a ring carbon and is selected from halo, nitro, cyano, hydroxy, trifluoromethyl, trifluoromethoxy, amino, carboxy, carbamoyl, sulphamoyl, $C_{1-3}$alkyl, $C_{2-3}$alkenyl, $C_{1-3}$alkoxy, $C_{1-3}$alkanoyl, $C_{1-3}$alkanoyloxy, N-($C_{1-3}$alkyl)amino, N,N-($C_{1-2}$alkyl)$_2$amino, $C_{1-3}$alkanoylamino, N-($C_{1-3}$ alkyl)carbamoyl, N,N-($C_{1-2}$alkyl)$_2$carbamoyl, $C_{1-3}$alkylS(O)$_a$ wherein a is 0 to 2, N-($C_{1-3}$alkyl) sulphamoyl and N,N-($C_{1-3}$alkyl)$_2$sulphamoyl;
  m is 0–2; wherein the values of $R^2$ may be the same or different;
  n is 0;
  Ring B is phenyl or indanyl;
  $R^3$ is halo or sulphamoyl;
  $R^4$ is a group A—E—; wherein
  A is optionally substituted on carbon by one or more D and is selected from $C_{1-4}$alkyl, phenyl, a heterocyclic group or phenyl$C_{1-4}$alkyl;

E is a direct bond or —O—, —C(O)—, —N(R$^a$)C(O)—, —S(O)$_r$— or —N(R$^a$)SO$_2$—; wherein R$^a$ is hydrogen, methyl or ethyl and r is 0–2;
  p is 0–2; wherein the values of $R^3$ may be the same or different;
  D is oxo, cyano, hydroxy, amino, carboxy, carbamoyl, sulphamoyl $C_{1-3}$alkyl, $C_{2-3}$alkenyl $C_{2-3}$alkynyl, $C_{1-3}$alkoxy, $C_{1-3}$alkanoyl, N-($C_{1-3}$alkyl)amino, N,N-($C_{1-2}$alkyl)$_2$amino, $C_{1-3}$alkanoylamino, N-($C_{1-3}$alkyl)carbamoyl, N,N-($C_{1-2}$alkyl)$_2$carbamoyl, $C_{1-3}$alkylS(O)$_a$ wherein a is 0 to 2, N-($C_{1-3}$alkyl)sulphamoyl or N,N-($C_{1-3}$alkyl)$_2$sulphamoyl;
  q is 0–1; wherein the values of $R^4$ may be the same or different;
or a pharmaceutically acceptable salt or an in vivo hydrolysable ester thereof.

Therefore in a further aspect of the invention, there is provided a compound of formula (I) as depicted above wherein:
  Ring A is imidazo[1,2a]pyrid-3-yl or pyrazolo[2,3a]pyrid-3-yl;
  $R^2$ is attached to a ring carbon and is $C_{1-3}$alkyl;
  m is 0–2; wherein the values of $R^2$ may be the same or different;
  n is 0;
  Ring B is phenyl or indan-5-yl;
  $R^3$ is fluoro, chloro, bromo or sulphamoyl;
  p is 0–2; wherein the values of $R^3$ may be the same or different;
  $R^4$ is methyl, ethyl, methoxy, methylthio, mesyl, acetyl, 3-N,N-dimethylamino-2-hydroxypropoxy, 2-N,N-diethylaminoethoxy, benzyloxy, anilinosulphonyl, pyrimidin-2-ylaminosulphonyl, phenoxy, 3,5-dioxapiperidin-1-ylsulphonyl.
  q is 0–1; wherein the values of $R^4$ may be the same or different;
or a pharmaceutically acceptable salt or an in vivo hydrolysable ester thereof.

Therefore in an additional aspect of the invention, there is provided a compound of formula (I) as depicted above wherein:
  Ring A and $(R^2)_m$ together form imidazo[1,2a]pyrid-3-yl, pyrazolo[2,3a]pyrid-3-yl, 2-methylimidazo[1,2a]pyrid-3-yl, 2-methylpyrazolo[2,3a]pyrid-3-yl or 2,5-dimethylimidazo[1,2a]pyrid-3-yl;
  n is 0;
  Ring B, $(R^3)_p$ and $(R^4)_q$ together form phenyl, 2-fluorophenyl, 3-fluorophenyl, 4-fluorophenyl, 2-chlorophenyl, 3-chlorophenyl, 4-chlorophenyl, 3-bromophenyl, 3-methylphenyl, 4-methylphenyl, 3-ethylphenyl, 3-methoxyphenyl, 4-methoxyphenyl, 3-methylthiophenyl, 4-methylthiophenyl, 4-mesylphenyl, 3-sulphamoylphenyl, 4-sulphamoylphenyl, 3-acetylphenyl, 3,4-dichlorophenyl, 3-chloro-4-fluorophenyl, 2-chloro-4-methylphenyl, 4-(3-N,N-dimethylamino-2-hydroxypropoxy)phenyl, 4-benzyloxyphenyl, 4-anilinosulphonylphenyl, 4-(pyrimidin-2-ylsulphonyl) phenyl, 4-phenoxyphenyl 4-(2-N,N-diethylaminoethoxy) phenyl, 4-(3,5-dioxapiperidin-1-ylsulphonyl)phenyl or indanyl;
or a pharmaceutically acceptable salt or an in vivo hydrolysable ester thereof.

Therefore in a further additional aspect of the invention, there is provided a compound of formula (I) as depicted above wherein:

Ring A is imidazo[1,2a]pyrid-3-yl or pyrazolo[2,3a]pyrid-3-yl;

$R^1$ is halo or $C_{1-3}$alkylS(O)$_a$ wherein a is 0; wherein the $C_{1-3}$alkyl group may be optionally substituted on carbon by one or more J; wherein J is hydroxy.

n is 0–1;

$R^2$ is attached to a ring carbon and is selected from halo, cyano, $C_{1-6}$alkyl, $C_{1-6}$alkoxy, $C_{1-6}$alkylS(O)$_a$ wherein a is 0, phenyl, phenylthio or (heterocyclic group)thio; wherein any $C_{1-6}$alkyl, phenyl or heterocyclic group may be optionally substituted on carbon by one or more G; wherein G is selected from hydroxy and dimethylamino.

m is 0–2; wherein the values of $R^2$ may be the same or different;

Ring B is phenyl or indan-5-yl;

$R^3$ is fluoro, chloro, bromo or sulphamoyl;

p is 0–1;

$R^4$ is a group A—E—; wherein

A is selected from $C_{1-6}$alkyl, phenyl, a heterocyclic group, $C_{3-8}$cycloalkyl, phenyl$C_{1-6}$alkyl, (heterocyclic group)$C_{1-6}$alkyl or $C_{3-8}$cycloalkyl$C_{1-6}$cycloalkyl; which $C_{1-6}$alkyl, phenyl, a heterocyclic group, $C_{3-8}$cycloalkyl, phenyl$C_{1-6}$alkyl, (heterocyclic group)$C_{1-6}$alkyl or $C_{3-8}$cycloalkyl$C_{1-6}$cycloalkyl may be optionally substituted on carbon by one or more D; and wherein if said heterocyclic group contains an —NH— moiety that nitrogen may be optionally substituted by a group selected from R;

E is a direct bond or —O—, —C(O)—, —N($R^a$)C(O)—, —S(O)$_r$— or —N($R^a$)SO$_2$; wherein $R^a$ is hydrogen or $C_{1-6}$alkyl and r is 0–2;

D is independently selected from hydroxy, amino, $C_{1-6}$alkoxy, N-($C_{1-6}$alkyl)amino, N,N-($C_{1-6}$alkyl)$_2$ amino, $C_{1-6}$alkoxycarbonylamino or benzyloxycarbonylamino; wherein any $C_{1-6}$alkyl may be optionally substituted on carbon by one or more K;

K is selected from hydroxy or diethylamino; and

R is $C_{1-4}$alkyl; and q is 0–1;

or a pharmaceutically acceptable salt or an in vivo hydrolysable ester thereof.

Therefore in a another additional aspect of the invention, there is provided a compound of formula (I) as depicted above wherein:

Ring A is imidazo[1,2a]pyrid-3-yl;

n is 0;

Ring B is phenyl;

$R^3$ is sulphamoyl;

p is 0–1;

$R^4$ is N-methylsulphamoyl, N-(2-methoxyethyl) sulphamoyl, N-(2-methylaminoethyl)sulphamoyl, N-(2-dimethylaminoethyl)sulphamoyl, N-(3-methoxypropyl)sulphamoyl, N-(3-dimethylaminopropyl)sulphamoyl or N-(3-isopropylaminopropyl)sulphamoyl; and q is 0–1;

or a pharmaceutically acceptable salt or an in vivo hydrolysable ester thereof.

In another aspect of the invention, preferred compounds of the invention are any one of Examples 1–38 or a pharmaceutically acceptable salt or an in vivo hydrolysable ester thereof.

In another aspect of the invention, preferred compounds of the invention are any one of Examples 1–98 or a pharmaceutically acceptable salt or an in vivo hydrolysable ester thereof.

In a further aspect of the invention, preferred compounds of the invention are Examples 7, 39, 40, 52, 53, 55, 65, 68 and 86 or a pharmaceutically acceptable salt or an in vivo hydrolysable ester thereof.

Preferred aspects of the invention are those which relate to the compound of formula (I) or a pharmaceutically acceptable salt thereof.

Another aspect of the present invention provides a process for preparing a compound of formula (I) or a pharmaceutically acceptable salt or an in vivo hydrolysable ester thereof which process (wherein $R^1$, $R^2$, $R^3$, $R^4$, Ring A, Ring B, m, p, q and n are, unless otherwise specified, as defined in formula (I)) comprises of:

a) reaction of a pyrimidine of formula (II):

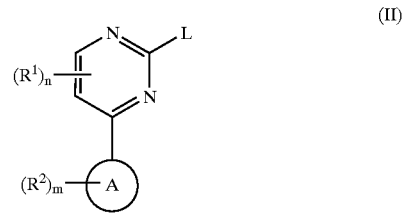

(II)

wherein L is a displaceable group; with an amine of formula (III):

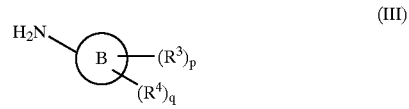

(III)

b) reacting a pyrimidine of formula (IV):

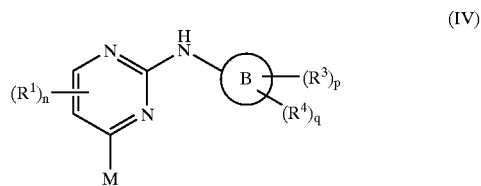

(IV)

with a compound of the formula (V):

(V)

wherein one of M and Q is a displaceable group X and the other is an metallic reagent Y; or c) reacting a compounds of formula (VI):

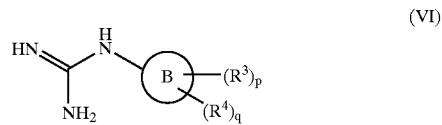

(VI)

with a compound of formula (VII):

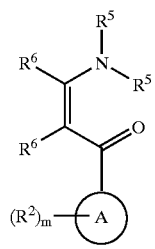

wherein $R^5$ is $C_{1-6}$alkyl and $R^6$ is hydrogen or $R^1$;
and thereafter if necessary:
i) converting a compound of the formula (I) into another compound of the formula (I);
ii) removing any protecting groups;
iii) forming a pharmaceutically acceptable salt or in vivo hydrolysable ester.

L is a displaceable group, suitable values for L are for example, a halogeno or sulphonyloxy group, for example a chloro, bromo, methanesulphonyloxy or toluene-4-sulphonyloxy group.

A suitable displaceable group X is, for example, a halogeno or sulphonyl group, for example a bromo, iodo or trifluoromethylsulphonyl group.

A suitable metallic group Y, is, for example, copper, lithium, an organoboron reagent such as —B(OH)$_2$, —B(OPr$^i$)$_2$ or —B(Et)$_2$, or an organotin compound such as SnBu$_3$, an organosilicon compound such as Si(Me)F$_2$, an organozirconium compound such as ZrCl$_3$, an organoaluminium compound such as AlEt$_2$, an organomagnesium compound such as MgBr, an organozinc compound such as ZnCl or an organomercury compound such as HgBr. Specific reaction conditions for the above reactions are as follows.

a) Pyrimidines of formula (II) and amines of formula (II) may be reacted together:
i) in the presence of a suitable solvent for example a ketone such as acetone or an alcohol such as ethanol or butanol or an aromatic hydrocarbon such as toluene or N-methylpyrrolidine, optionally in the presence of a suitable acid for example an inorganic acid such as hydrochloric acid or sulphuric acid, or an organic acid such as acetic acid or formic acid (or a suitable Lewis acid) and at a temperature in the range of 0° C. to reflux, preferably reflux; or
ii) under standard Buchwald conditions (for example see *J. Am. Chem. Soc.*, 118, 7215; *J. Am. Chem. Soc.*, 119, 8451; *J. Org. Chem.*, 62, 1568 and 6066) for example in the presence of palladium acetate, in a suitable solvent for example an aromatic solvent such as toluene, benzene or xylene, with a suitable base for example an inorganic base such as caesium carbonate or an organic base such as potassium-t-butoxide, in the presence of a suitable ligand such as 2,2'-bis(diphenylphosphino)-1,1'-binaphthyl and at a temperature in the range of 25 to 80° C.

Pyrimidines of the formula (II) may be prepared according to SCHEME I

SCHEME I

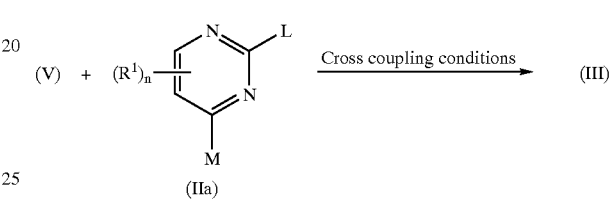

wherein one of M and Q is a displaceable group X as defined above and the other is an metallic reagent Y as defined above.

Cross coupling conditions are well known in the art. Suitable conditions include, for example, those described under b) below.

Where Ring A is imidazo[1,2a]pyrid-3-yl compounds of the formula (II) may also be prepared according to SCHEME II K is a suitable leaving group (for example $C_{1-6}$alkanoyloxy), $R^6$ is as defined above, y is 0–4, $R^7$ is hydrogen or $R^2$; Q is a suitable leaving group (for example $C_{1-6}$alkoxy) and $R^5$ is as defined above.

Where Ring A is pyrazolo[2,3a]pyrid-3-yl compounds of the formula (II) may also be prepared according to SCHEME III

SCHEME II

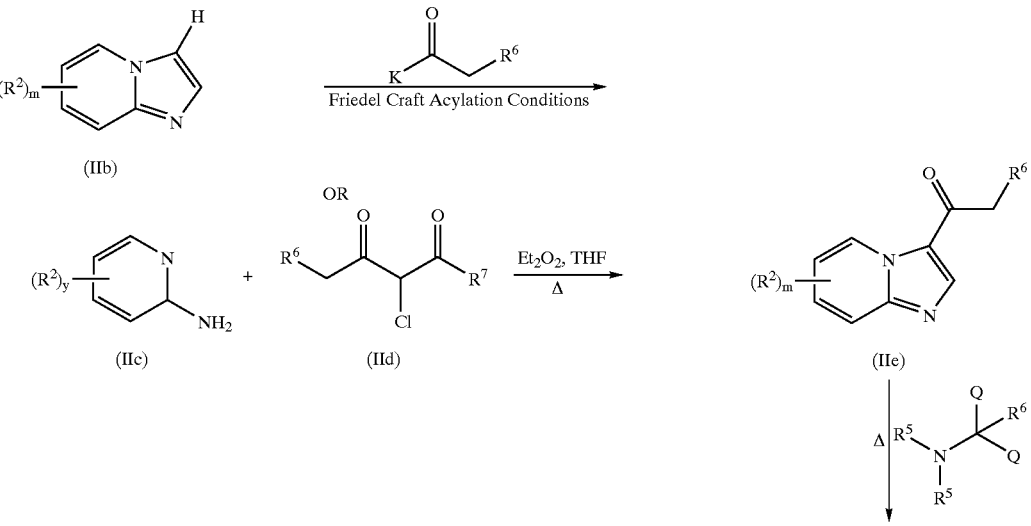

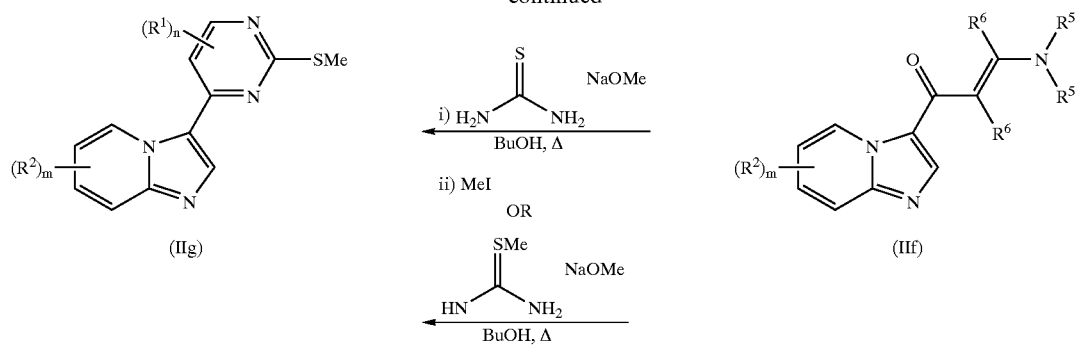

SCHEME III

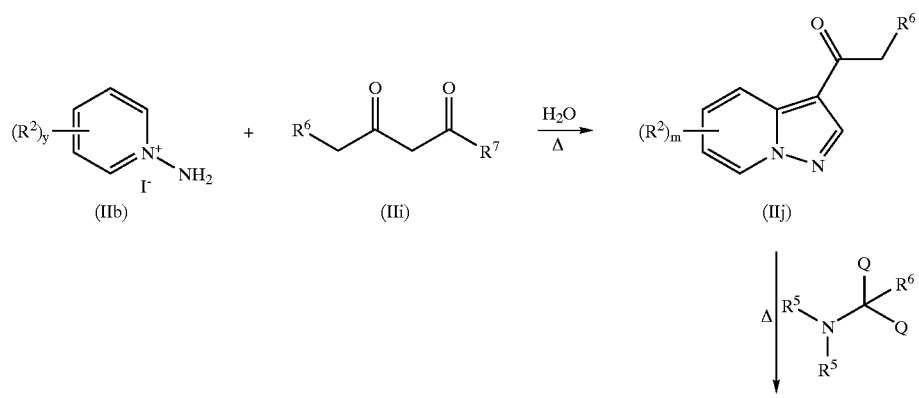

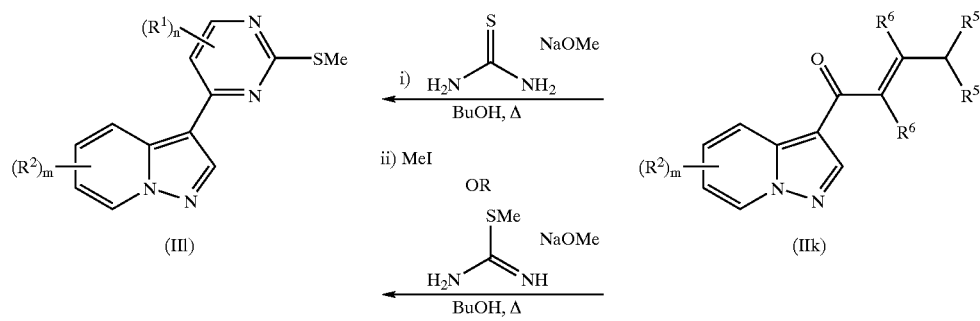

wherein $R^5$, $R^6$ and $R^7$ are as defined above.

Compounds of formula (IIf) or (IIk) may be further modified to produce compounds of formula (IIn):

SCHEME IV

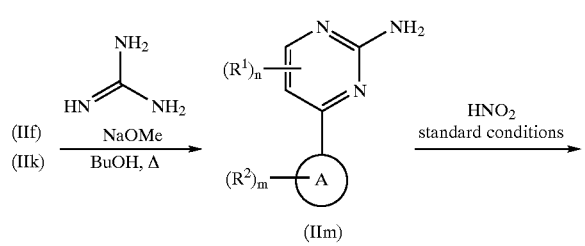

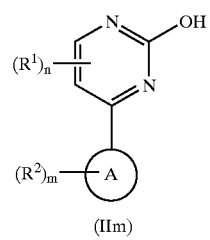

It will be appreciated by those skilled in the art that compounds of formula (IIn) may be additionally modified by standard functional group modification reactions known in the art to produce compounds of formula (II) where L is other leaving groups for example chloro, bromo, tosyl and mesyl.

Compounds of formula (IIa), (IIb), (IIc), (IId), (IIh), (IIi) and (III) are commercially available compounds, or they are known in the literature, or they are prepared by standard processes known in the art.

b) Compounds of formula (IV) and compounds of formula (V) may be reacted together under standard cross coupling conditions. Examples of these are in the presence of a catalyst, for example, a metallic catalyst such as tetrakis(triphenylphosphine)palladium(0), palladium(II) chloride, palladium(II) bromide, nickel(II) chloride, nickel(II) bromide or bis(triphenylphosphine)nickel(II) chloride, in the presence of a suitable inert solvent or diluent, for example tetrahydrofuran, 1,4-dioxan, 1,2-dimethoxyethane, benzene, toluene, xylene, methanol or ethanol. The reaction is preferably conducted in the presence of a suitable base such as, for example, sodium carbonate or potassium carbonate, pyridine, 4-dimethylaminopyridine, triethylamine or morpholine, and conveniently at a temperature in the range, for example 10 to 250° C., preferably in the range 60 to 120° C.

Compounds of formula (MV) may be prepared according to SCHEME V

SCHEME V

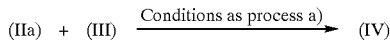

Compounds of formula (V) are commercially available compounds, or they are known in the literature, or they are prepared by standard processes known in the art.

c) compounds of formula (VI) and compounds of formula (VII) are reacted together in a suitable solvent such as N-methylpyrrolidinone or butanol at a temperature in the range of 100–200° C., preferably in the range of 150–170° C. The reaction is preferably conducted in the presence of a suitable base such as, for example, sodium methoxide or potassium carbonate.

Compounds of formula (VI) and (VII) are commercially available compounds, or they are known in the literature, or they are prepared by standard processes known in the art, or compounds of formula (VII) may be prepared by a process similar to that described for (IIf) and (IIk) hereinabove.

It will be appreciated that certain of the various ring substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acyl halide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogeno group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulphinyl or alkylsulphonyl.

It will also be appreciated that in some of the reactions mentioned herein it may be necessary/desirable to protect any sensitive groups in the compounds. The instances where protection is necessary or desirable and suitable methods for protection are known to those skilled in the art. Conventional protecting groups may be used in accordance with standard practice (for illustration see T. W. Green, Protective Groups in Organic Synthesis, John Wiley and Sons, 1991). Thus, if reactants include groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl ethoxycarbonyl or 1-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

As stated hereinbefore the compounds defined in the present invention possesses anti-cell-proliferation activity such as anticancer activity which is believed to arise from the CDK inhibitory activity of the compound. These properties may be assessed, for example, using the procedure set out below:

Assay

The following abbreviations have been used:
HEPES is N-[2-Hydroxyethyl]piperazine-N'-[2-ethanesulfonic acid]
DTT is Dithiothretiol
PMSF is Phenylmethylsulfonyl fluoride The compounds were tested in an in vitro kinase assay in 96 well format using Scintillation Proximity Assay (SPA—obtained from Amersham) for measuring incorporation of [γ-33-P]-Adenosine Triphosphate into a test substrate (GST-Retinoblastoma protein; GST-Rb). In each well was placed the compound to be tested (diluted in DMSO and water to correct concentrations) and in control wells either roscovitine as an inhibitor control or DMSO as a positive control.

Approximately 0.2 µl of CDK2/Cyclin E partially-purified enzyme (amount dependent on enzyme activity) diluted in 25 µl incubation buffer was added to each well then 20 µl of GST-Rb/ATP/ATP33 mixture (containing 0.5 µg GST-Rb and 0.2 µM ATP and 0.14 µCi [γ-33-P]-Adenosine Triphosphate in incubation buffer), and the resulting mixture shaken gently, then incubated at room temperature for 60 minutes.

To each well was then added 150 µL stop solution containing (0.8 mg/well of Protein A-PVT SPA bead (Amersham)), 20 pM/well of Anti-Glutathione Transferase, Rabbit IgG (obtained from Molecular Probes), 61 mM EDTA and 50 mM HEPES pH 7.5 containing 0.05% sodium azide.

The plates were sealed with Topseal-S plate sealers, left for two hours then spun at 2500 rpm, 1124× g., for 5 minutes. The plates were read on a Topcount for 30 seconds per well.

The incubation buffer used to dilute the enzyme and substrate mixes contained 50 mM HEPES pH7.5, 10 mM $MnCl_2$, 1 mM DTT, 100 µM Sodium vanadate, 100 µM NaF, 10 mM Sodium Glycerophosphate, BSA (1 mg/ml final).

Test Substrate

In this assay only part of the retinoblastoma protein (Science 1987 March 13;235(4794):1394–1399; Lee W. H., Bookstein R., Hong F., Young L. J., Shew J. Y., Lee E. Y.) was used, fused to a GST tag. PCR of retinoblastoma gene encoding amino acids 379–928 (obtained from retinoblastoma plasmid ATCC pLRbRNL) was performed, and the sequence cloned into pGEX 2T fusion vector (Smith D. B. and Johnson, K. S. Gene 67, 31 (1988); which contained a tac promoter for inducible expression, internal lac $I^q$ gene for use in any E. Coli host, and a coding region for thrombin cleavage—obtained from Pharmacia Biotech) which was used to amplify amino acids 792–928. This sequence was again cloned into pGEX 2T.

The retinoblastoma 792–928 sequence so obtained was expressed in E. Coli (BL21 (DE3) pLysS cells) using standard inducible expression techniques, and purified as follows.

E. coli paste was resuspended in 10 ml/g of NETN buffer (50 mM Tris pH 7.5, 120 mM NaCl, 1 mM EDTA, 0.5% v/v NP-40, 1 mM PMSF, 1 ug/ml leupeptin, 1 ug/ml aprotinin and 1 ug/ml pepstatin) and sonicated for 2×45 seconds per 100 ml homogenate. After centrifugation, the supernatant was loaded onto a 10 ml glutathione Sepharose column (Pharmacia Biotech, Herts, UK), and washed with NETN buffer. After washing with kinase buffer (50 mM HEPES pH 7.5, 10 mM MgCl2, 1 mM DTT, 1 mM PMSF, 1 ug/ml leupeptin, 1 ug/ml aprotinin and 1 ug/ml pepstatin) the protein was eluted with 50 mM reduced glutathione in kinase buffer. Fractions containing GST-Rb(792–927) were pooled and dialysed overnight against kinase buffer. The final product was analysed by Sodium Dodeca Sulfate (SDS) PAGE (Polyacrylamide gel) using 8–16% Tris-Glycine gels (Novex, San Diego, USA).

CDK2 and Cyclin E

The open reading frames of CDK2 and Cyclin E were isolated by reverse transcriptase-PCR using HeLa cell and activated T cell mRNA as a template and cloned into the insect expression vector pVL1393 (obtained from Invitrogen 1995 catalogue number. V1392-20). CDK2 and cyclin E were then dually expressed [using a standard virus Baculogold co-infection technique] in the insect SF21 cell system (*Spodoptera Frugiperda* cells derived from ovarian tissue of the Fall Army Worm commercially available).

Example Production of Cyclin E/CDK2

The following Example provides details of the production of Cyclin E/CDK2 in SF21 cells (in TC100+10% FBS (TCS)+0.2% Pluronic) having dual infection MOI 3 for each virus of Cyclin E & CDK2.

SF21 cells grown in a roller bottle culture to $2.33 \times 10^6$ cells/ml were used to inoculate 10×500 ml roller bottles at 0.2×10E6 cells/ml. The roller bottles were incubated on a roller rig at 28° C.

After 3 days (72 hrs.) the cells were counted, and the average from 2 bottles found to be 1.86×10E6 cells/ml. (99% viable). The cultures were then infected with the dual viruses at an MOI 3 for each virus.

The viruses were mixed together before addition to the cultures, and the cultures returned to the roller rig 28° C.

After 2 days (48 hrs.) post infection the 5 Litres of culture was harvested. The total cell count at harvest was 1.58×10E6 cells/ml. (99% viable). The cells were spun out at 2500 rpm, 30 mins., 4° C. in Heraeus Omnifuge 2.0 RS in 250 ml. lots. The supernatant was discarded.

Partial Co-Purification of Cdk2 and Cyclin E

Sf21 cells were resuspended in lysis buffer (50 mM Tris pH 8.2, 10 mM $MgCl_2$, 1 mM DTT, 10 mM glycerophosphate, 0.1 mM sodium orthovanadate, 0.1 mM NaF, 1 mM PMSF, 1 ug/ml leupeptin and 1 ug/ml aprotinin) and homogenised for 2 minutes in a 10 ml Dounce homgeniser. After centrifugation, the supernatant was loaded onto a Poros HQ/M 1.4/100 anion exchange column (PE Bio systems, Hertford, UK). Cdk2 and Cyclin E were coeluted at the beginning of a 0–1M NaCl gradient (run in lysis buffer minus protease inhibitors) over 20 column volumes. Co-elution was checked by western blot using both anti-Cdk2 and anti-Cyclin E antibodies (Santa Cruz Biotechnology, California, US).

By analogy, assays designed to assess inhibition of CDK4 and CDK6 may be constructed. CDK2 (EMBL Accession No. X62071) may be used together with Cyclin A or Cyclin E (see EMBL Accession No. M73812), and further details for such assays are contained in PCT International Publication No. WO99/21845, the relevant Biochemical & Biological Evaluation sections of which are hereby incorporated by reference.

Although the pharmacological properties of the compounds of the formula (I) vary with structural change, in general activity possessed by compounds of the formula (I) may be demonstrated at $IC_{50}$ concentrations or doses in the range 250 µM to 1 nM.

When tested in the above in-vitro assay the CDK2 inhibitory activity of Example 11 was measured as $IC_{50}=0.19$ µM and that of Example 12 as $IC_{50}=0.17$ µM.

The in vivo activity of the compounds of the present invention may be assessed by standard techniques, for example by measuring inhibition of cell growth and assessing cytotoxicity.

Inhibition of cell growth may be measured by staining cells with Sulforhodamine B (SRB), a fluorescent dye that stains proteins and therefore gives an estimation of amount of protein (i.e. cells) in a well (see Boyd, M. R. (1989) Status of the NCI preclinical antitumour drug discovery screen. Prin. Prac Oncol 10:1–12). Thus, the following details are provided of measuring inhibition of cell growth:

Cells were plated in appropriate medium in a volume of 100 ml in 96 well plates; media was Dulbecco's Modified Eagle media for MCF-7, SK-UT-1B and SK-UT-1. The cells were allowed to attach overnight, then inhibitor compounds were added at various concentrations in a maximum concentration of 1% DMSO (v/v). A control plate was assayed to give a value for cells before dosing. Cells were incubated at 37° C., (5% $CO_2$) for three days.

At the end of three days TCA was added to the plates to a final concentration of 16% (v/v). Plates were then incubated at 4° C. for 1 hour, the supernatant removed and the plates washed in tap water. After drying, 100 ml SRB dye (0.4% SRB in 1% acetic acid) was added for 30 minutes at 37° C. Excess SRB was removed and the plates washed in 1% acetic acid. The SRB bound to protein was solubilised in 10 mM Tris pH7.5 and shaken for 30 minutes at room temperature. The ODs were read at 540 nm, and the concentration of inhibitor causing 50% inhibition of growth was determined from a semi-log plot of inhibitor concentration versus absorbance. The concentration of compound that reduced the optical density to below that obtained when the cells were plated at the start of the experiment gave the value for toxicity.

Typical $IC_{50}$ values for compounds of the invention when tested in the SRB assay are in the range 1 mM to 1 nM.

According to a further aspect of the invention there is provided a pharmaceutical composition which comprises a pyrimidine derivative of the formulas) or a pharmaceutically acceptable salt or in vivo hydrolysable ester thereof; as defined hereinbefore in association with a pharmaceutically-acceptable diluent or carrier.

According to a further aspect of the invention there is provided a pharmaceutical composition which comprises a compound of formula (I), or a pharmaceutically acceptable salt or in vivo hydrolysable ester thereof as defined hereinbefore in association with a pharmaceutically-acceptable diluent or carrier.

The composition may be in a form suitable for oral administration, for example as a tablet or capsule, for parenteral injection (including intravenous, subcutaneous, intramuscular, intravascular or infusion) as a sterile solution, suspension or emulsion, for topical administration as an ointment or cream or for rectal administration as a suppository.

In general the above compositions may be prepared in a conventional manner using conventional excipients.

The compound of formula (I) will normally be administered to a warm-blooded animal at a unit dose within the range 5–5000 mg per square meter body area of the animal, i.e. approximately 0.1–100 mg/kg, and this normally provides a therapeutically-effective dose. A unit dose form such as a tablet or capsule will usually contain, for example 1–250 mg of active ingredient. Preferably a daily dose in the range of 1–50 mg/kg is employed. However the daily dose will necessarily be varied depending upon the host treated, the particular route of administration, and the severity of the illness being treated. Accordingly the optimum dosage may be determined by the practitioner who is treating any particular patient.

According to a further aspect of the present invention there is provided a compound of the formula (I), or a pharmaceutically acceptable salt or in vivo hydrolysable ester thereof, as defined hereinbefore for use in a method of treatment of the human or animal body by therapy.

We have found that the compounds defined in the present invention, or a pharmaceutically acceptable salt or in vivo hydrolysable ester thereof, are effective cell cycle inhibitors (anti-cell proliferation agents), which property is believed to arise from their CDK inhibitory properties. Accordingly the compounds of the present invention are expected to be useful in the treatment of diseases or medical conditions mediated alone or in part by CDK enzymes, i.e. the compounds may be used to produce a CDK inhibitory effect in a warm-blooded animal in need of such treatment. Thus the compounds of the present invention provide a method for treating the proliferation of malignant cells characterised by inhibition of CDK enzymes, i.e. the compounds may be used to produce an anti-proliferative effect mediated alone or in part by the inhibition of CDKs. Such a compound of the invention is expected to possess a wide range of anti-cancer properties as CDKs have been implicated in many common human cancers such as leukaemia and breast, lung, colon, rectal, stomach, prostate, bladder, pancreas and ovarian cancer. Thus it is expected that a compound of the invention will possess anti-cancer activity against these cancers. It is in addition expected that a compound of the present invention will possess activity against a range of leukaemias, lymphoid malignancies and solid tumours such as carcinomas and sarcomas in tissues such as the liver, kidney, prostate and pancreas. In particular such compounds of the invention are expected to slow advantageously the growth of primary and recurrent solid tumours of, for example, the colon, breast, prostate, lungs and skin. More particularly such compounds of the invention, or a pharmaceutically acceptable salt or in vivo hydrolysable ester thereof, are expected to inhibit the growth of those primary and recurrent solid tumours which are associated with CDKs, especially those tumours which are significantly dependent on CDKs for their growth and spread, including for example, certain tumours of the colon, breast, prostate, lung, vulva and skin.

It is further expected that a compound of the present invention will possess activity against other cell-proliferation diseases in a wide range of other disease states including leukaemias, fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation.

Thus according to this aspect of the invention there is provided a compound of the formula (I), or a pharmaceutically acceptable salt or in vivo hydrolysable ester thereof, as defined hereinbefore for use as a medicament; and the use of a compound of the formula (I), or a pharmaceutically acceptable salt or in vivo hydrolysable ester thereof, as defined hereinbefore in the manufacture of a medicament for use in the production of a cell cycle inhibitory (anti-cell-proliferation) effect in a warm-blooded animal such as man. Particularly, an inhibitory effect is produced by preventing entry into or progression through the S phase by inhibition of CDK2, CDK4 and/or CDK6, especially CDK2.

According to a further feature of the invention there is provided the use of a compound of the formula (I), or a pharmaceutically acceptable salt or in vivo hydrolysable ester thereof, as defined hereinbefore in the manufacture of a medicament for use in the treatment of cancers (solid tumours and leukemias), fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation.

According to a further feature of this aspect of the invention there is provided a method for producing a cell cycle inhibitory (anti-cell-proliferation) effect in a warm-blooded animal, such as man, in need of such treatment which comprises administering to said animal an effective amount of a compound as defined immediately above. Particularly, an inhibitory effect is produced by preventing entry into or progression through the S phase by inhibition of CDK2, CDK4 and/or CDK6, especially CDK2.

As stated above the size of the dose required for the therapeutic or prophylactic treatment of a particular cell-proliferation disease will necessarily be varied depending on the host treated, the route of administration and the severity of the illness being treated. A unit dose in the range, for example, 1–100 mg/kg, preferably 1–50 mg/kg is envisaged.

The CDK inhibitory activity defined hereinbefore may be applied as a sole therapy or may involve, in addition to a compound of the invention, one or more other substances and/or treatments. Such conjoint treatment may be achieved by way of the simultaneous, sequential or separate administration of the individual components of the treatment. In the field of medical oncology it is normal practice to use a combination of different forms of treatment to treat each patient with cancer. In medical oncology the other component(s) of such conjoint treatment in addition to the cell cycle inhibitory treatment defined hereinbefore may be: surgery, radiotherapy or chemotherapy. Such chemotherapy may cover three main categories of therapeutic agent:

(i) other cell cycle inhibitory agents that work by the same or different mechanisms from those defined hereinbefore;

(ii) cytostatic agents such as antioestrogens (for example tamoxifen, toremifene, raloxifene, droloxifene, iodoxyfene), progestogens (for example megestrol acetate), aromatase inhibitors (for example anastrozole, letrazole, vorazole, exemestane), antiprogestogens, antiandrogens (for example flutamide, nilutamide, bicalutamide, cyproterone acetate), LHRH agonists and antagonists (for example goserelin acetate, luprolide), inhibitors of testosterone 5α-dihydroreductase (for example finasteride), anti-invasion agents (for example metalloproteinase inhibitors like marimastat and inhibitors of urokinase plasminogen activator receptor function) and inhibitors of growth factor function, (such growth factors include for example platelet derived growth factor and hepatocyte growth factor such inhibitors include growth factor antibodies, growth factor receptor antibodies, tyrosine kinase inhibitors and serine/threonine kinase inhibitors); and (iii) antiproliferative/antineoplastic drugs and combinations thereof, as used in medical oncology, such as antimetabolites (for example antifolates like methotrexate, fluoropyrimidines like 5-fluorouracil, purine and adenosine analogues, cytosine arabinoside); antitumour antibiotics (for example anthracyclines like doxorubicin, daunomycin, epirubicin and idarubicin, mitomycin-C, dactinomycin, mithramycin); platinum derivatives (for example cisplatin, carboplatin); alkylating agents (for example nitrogen mustard, melphalan, chlorambucil, busulphan, cyclophosphamide, ifosfamide, nitrosoureas, thiotepa); antimitotic agents (for example vinca alkaloids like vincrisitine and taxoids like taxol, taxotere); topoisomerase inhibitors (for example epipodophyllotoxins like etoposide and teniposide, amsacrine, topotecan). According to this aspect of the invention there is provided a pharmaceutical product comprising a compound of the formula (I) as defined hereinbefore and an additional anti-tumour substance as defined hereinbefore for the conjoint treatment of cancer.

In addition to their use in therapeutic medicine, the compounds of formula (I) and their pharmaceutically acceptable salts are also useful as pharmacological tools in the development and standardisation of in vitro and in vivo test systems for the evaluation of the effects of inhibitors of cell cycle activity in laboratory animals such as cats, dogs, rabbits, monkeys, rats and mice, as part of the search for new therapeutic agents.

In the above other pharmaceutical composition, process, method, use and medicament manufacture features, the alternative and preferred embodiments of the compounds of the invention described herein also apply.

EXAMPLES

The invention will now be illustrated by the following non-limiting examples in which, unless stated otherwise:

(i) temperatures are given in degrees Celsius (° C.); operations were carried out at room or ambient temperature, that is, at a temperature in the range of 18–25° C.;

(ii) organic solutions were dried over anhydrous magnesium sulphate; evaporation of solvent an was carried out using a rotary evaporator under reduced pressure (600–4000 Pascals; 4.5–30 mmHg) with a bath temperature of up to 60° C.;

(iii) chromatography means flash chromatography on silica gel; thin layer chromatography (TLC) was carried out on silica gel plates; where a silica Bond Elut column is referred to, this means a column containing 10 g or 20 g of silica of 40 micron particle size, the silica being contained in a 60 ml disposable syringe and supported by a porous disc, obtained from Varian, Harbor City, Calif., USA under the name "Mega Bond Elut SI", "Mega Bond Elut" is a trademark;

(iv) in general, the course of reactions was followed by TLC and reaction times are given for illustration only, (v) final products had satisfactory proton nuclear magnetic resonance (NMR) spectra and/or mass spectral data;

(vi) yields are given for illustration only and are not necessarily those which can be obtained by diligent process development; preparations were repeated if more material was required;

(vii) when given, NMR data is in the form of delta values for major diagnostic protons, given in parts per million (ppm) relative to tetramethylsilane (TMS) as an internal standard, determined at 300 MHz using perdeuterio dimethyl sulphoxide (DMSO-$d_6$) as solvent unless otherwise indicated;

(viii) chemical symbols have their usual meanings; SI units and symbols are used;

(ix) solvent ratios are given in volume:volume (v/v) terms; and (x) mass spectra were run with an electron energy of 70 electron volts in the chemical ionization (CI) mode using a direct exposure probe; where indicated ionization was effected by electron impact (EI), fast atom bombardment (FAB) or electrospray (ESP); values for m/z are given; generally, only ions which indicate the parent mass are reported;

(xi) unless stated otherwise compounds containing an asymmetrically substituted carbon and/or sulphur atom have not been resolved;
(xii) where a synthesis is described as being analogous to that described in a previous example the amounts used are the millimolar ratio equivalents to those used in the previous example;
(xvi) the following abbreviations have been used:

| | |
|---|---|
| NMP | 1-methyl-2-pyrrolidinone; |
| DMF | N,N-dimethylformamide; |
| DMFDMA | N,N-dimethylformamidedimethylacetyl; |
| DMSO | dimethylsulphoxide; |
| THF | tetrahydrofuran; and |
| EA | elemental analysis. |

Example 1
2-(3-Chloroanilino)-4-(2-methylimidazo[1,2a]pyrid-3-yl)pyrimidine

Sodium hydride (236 mg of a 60% suspension in mineral oil, 5.9 mmol) was added to a solution of 3-chloroaniline (496 mL 4.7 mmol) in NMP (10 ml) under nitrogen. The mixture was stirred for 30 minutes at ambient temperature and a solution of 4-(2-methylimidazo[1,2a]pyrid-3-yl)-2-methylthiopyrimidine (Method 1) (600 mg, 2.3 mmol) in NUT (2 ml) was added. The mixture was heated at 150° C. for 3 hours. The reaction mixture was allowed to cool diluted with water and extracted with ethyl acetate. The combined extracts were dried and the volatiles removed by evaporation. The residue was purified by chromatography eluting with ethyl acetate/hexane (1:1) increasing in polarity to ethyl acetate/methanol (97:3). The purified product was triturated with ether and hexane, collected by filtration and dried to give the title compound (159 mg, 21%). NMR: 2.62 (s, 3H), 6.98–7.04 (m, 2H) 7.12 (d, 1H), 7.25 (dd, 1H), 7.42 (dd, 1H), 7.59–7.64 (m, 2H), 8.02 (s, 1H), 8.55 (d, 1H), 9.72 (d, 1H), 9.84 (s, 1H).

Examples 2–12

Following the procedure of Example 1 and using the appropriate starting materials the following compounds were prepared.

| Ex | Compound | NMR | m/z [MH]+ |
|---|---|---|---|
| 2 | 2-(4-Sylphamoyanilino)-4-2-methylimidazo[1,2a]pyrid-3-yl)pyrimidine | 2.64(s, 3H), 7.05(dd, 1H), 7.15–7.20 (m, 3H), 7.44(dd, 1H), 7.64(d, 1H), 7.74(d, 2H), 7.92(d, 2H), 8.68(d, 1H), 9.75(d, 1H) | 381 |
| 3[1] | 2-Anilino-4-(2-methylmidazo[1,2a]pyrid-3-yl)pyrimidine | 2.64(s, 3H), 6.92–7.00(m, 2H), 7.08(d, 1H), 7.30(dd, 1H), 7.40(dd, 1H), 7.60 (d, 1H), 7.72(d, 2H), 8.50(d, 1H), 9.60 (s, 1H), 9.75(d, 1H) | 302 |
| 4 | 2-(4-Chloroanilino)-4-(2-methylimidazo[1,2a]pyrid-3-yl)pyrimidine | 2.75(s, 3H), 6.82(dd, 1H), 7.01(d, 1H), 7.22(br s, 1H), 7.30(m, 3H), 7.60 (m, 2H), 8.47(d, 1H), 9.53(d, 1H) | 336 |
| 5[1] | 2-(3-Chloroanilino)-4-(imidazo[1,2a]pyrid-3-yl)pyrimdine | 7.02(d, 1H), 7.12(dd, 1H), 7.30(dd, 1H), 7.42(d, 1H), 7.50(dd, 1H), 7.60 (d, 1H), 7.75(d, 1H), 8.00(s, 1H), 8.48 (d, 1H), 8.61(s, 1H), 9.82(s, 1H) | 322 |
| 6[1] | 2-3,4-Dichloroanilino)-4-(imidazo[1,2a]pyrid-3-yl)pyrimidine | 7.15(dd, 1H), 7.50(dd, 2H), 7.58(d, 1H), 7.65(dd, 1H), 7.78(d, 1H), 8.22 (d, 1H), 8.50(d, 1H), 8.62(s, 1H), 9.95 (s, 1H) | |
| 7 | 2-(4-Sulphamoylanilino)-4-(imidazo[1,2a]pyrid-3-yl)pyrimidine | 7.20(d, 3H), 7.55(d, 2H), 8.80(d, 3H), 8.95(d, 2H), 8.50(d, 1H), 8.68(s, 1H), 10.05(s, 1H), 10.10(d, 1H) | 367 |
| 8[1] | 2-(3-Chloro-4-fluoroanilino)-4-(imidazo[1,2a]pyrid-3-yl)pyrimidine | 7.14(dd, 1H), 7.32–7.55(m, 3H), 7.60 (dd, 1H), 7.78(d, 1H), 8.10(dd, 1H), 8.48(d, 1H), 8.62(s, 1H), 9.82(s, 1H) | 340 |
| 9 | 2-(2-Chloroanilino)-4-(imidazo[1,2a]pyrid-3-yl)pyrimidine | 7.08(dd, 1H), 7.17(d, 1H), 7.37(m, 2H), 7.48(dd, 1H), 7.51(br s, 1H), 7.62 (d, 1H), 7.76(d, 1H), 8.30(s, 1H), 8.40 (m, 1H), 9.81(d, 1H), 9.94(dd, 1H) | 322 |
| 10 | 2-(2-Chloro-4-methylanilino)-4-(imidazo[1,2a)pyrid-3-yl)pyrimidine | 2.38(s, 3H), 6.91(dd, 1H), 7.14(d, 1H), 7.28(br s, 1H), 7.38(m, 2H), 7.61 (s, 1H), 7.73(d, 1H), 8.16(d, 1H), 8.28 (s, 1H), 8.40(d, 1H), 9.78(d, 1H) | 336 |
| 11[1] | 2-[4-(3,5-Dioxapiperidin-1-yl)sulphonylanilino]-4-(imidazo[1,2a]pyrid-3-yl)pyrimidine | 4.87(s, 2H), 5.20(s, 4H), 7.16(dd, 1H), 7.51(d, 2H), 7.75(d, 1H), 7.83(d, 2H), 7.98(d, 2H), 8.50(d, 1H), 8.64(s, 1H) | 439 |
| 12[1,2] | 2-[4-(2-Diethylaminoethoxy)anilino]-4-(imidazo[1,2a]pyrid-3-yl)pyrimidine | 0.98(t, 6H), 2.50–2.62(m, 4H), 2.78–2.82(m, 2H), 4.00(t, 2H), 6.84 (dd, 2H), 7.08(dd, 1H), 7.38(d, 1H), | 403 |

| Ex | Compound | NMR | m/z [MH]+ |
|---|---|---|---|
| | | 7.48(dd, 1H), 7.60(s, 2H), 7.75(d, 1H), 8.38(d, 1H), 8.59(s, 1H), 9.42(s, 1H) | |

[1]Sodium bis(trimethylsilyl)amide(1M solution in THF) was used in place of sodium hydride.
[2]The product was purified by chromatography, eluting with dichloromethane/methanol (100:0 increasing to 80:20), triturated with ether and hexane and collected by filtration.

Example 13
2-[4-(3-Dimethylamino-2-hydroxypropoxy)anilino]-4-(imidazo[1,2a]pyrid-3-yl)pyrimidine A mixture of 4-(3-dimethylamino-2-hydroxypropoxy) aniline (497 mg, 1.76 mmol) (Method 11) and cyanamide (185 mg, 4.4 mmol) in NMP (1 ml) were heated at 160° C. for 30 minutes. A mixture of 3-(3-dimethylaminoprop-2-en-1-oyl)imidazo[1,2a]pyridine (Method 5) (400 mg, 1.76 mmol) and sodium methoxide (183 mg, 3.5 mmol) in 1-butanol (10 ml) was then added and the mixture heated at reflux for 3 hours. The mixture was allowed to cool and the residue was purified by chromatography, eluting with ethyl acetate/methanol (97:3 increasing in polarity to 90:10) to give the title compound (30 mg, 4%). NMR: 2.35 (s, 6H), 2.40 2.63 (m, 2H), 3.82 4.02 (m, 3H), 6.90 (d, 2H), 7.06 (dd, 1H), 7.30 (d, 1H), 7.50 (dd, 1H), 7.59 (s, 2H), 7.74 (d, 1H), 8.38 (d, 1H), 8.58 (s, 1H), 9.42 (s, 1H); m/z: 405 [MH]+.

Examples 14–15

Following the procedure of Example 13 and using the appropriate starting materials the following compounds were prepared.

| Ex | Compound | NMR | m/z [MH]+ |
|---|---|---|---|
| 14[1] | 2-[4-3-Dimethyl-amino-2-hydroxypropoxy)anilino]-4-(2-methyl-pyrazolo[2,3a]pyrid-3-yl)pyrimidine | 2.20(s, 6H), 2.26–2.45(m, 2H), 2.65(s, 3H), 3.80–3.95(m, 3H), 4.80(s, 1H), 6.88(d, 2H), 7.00(d, 2H), 7.38(dd, 1H), 7.60(d, 2H), 8.38(d, 1H), 8.44(d, 1H), 8.65(d, 1H), 9.21(s, 1H) | 419 |
| 15[1] | 2-[4-(3-Dimethylamino-2-hydroxypropoxy)anilino]-4-(2 methylimidazo[1,2,a]pyrid-3-yl)pyrimidine. | 2.63(s, 3H), 2.80(s, 6H), 3.12–3.26(m, 2H), 4.27(br s, 1H), 5.93(br s, 1H), 6.90–7.04(m, 4H), 7.40(t, 1H), 7.60 (dd, 2H), 8.45(d, 1H), 9045(s, 1H), 9.73(d, 1H) | 419 |

[1]Product was purified by chromatography eluting with dichloromethane/hexane (1:1) increasing in polarity to dichloromethane/methanol/triethylamine (96:4:0.5).
[2]Product was purified by chromatography eluting with dichloromethane/methanol/triethylamine (96:4:0.5) and recrystallized from acetonitrile/methanol.

Examples 16–36

The following examples were prepared, purified and characterised by the following generic method:

Sodium bis(trimethylsilyl)amide (2.05 ml of a 1M solution in THF, 2.05 mmol) was added to a solution of the aniline (1.65 mmol) in NMP (1.5 ml) under nitrogen. The mixture was stirred for 30 minutes at ambient temperature and a solution of 4-(imidazo[1,2a]pyrid-3-yl)-2-methylthiopyrimidine (Method 4)(200 mg, 0.83 mmol) in NMP (1 ml) was added. The reaction mixture was heated at 150° C. for 2.5 hours. The solvent and volatiles were removed by evaporation and the residue was purified by chromatography eluting with ethyl acetate, then ethyl acetate/methanol (97:3) and finally ethyl acetate/methanol (97:3). The reaction products were characterised by HPLC on a 4.6 mm×10 cm Hichrom RPB 100A column eluting water/acetonitrile/formic acid (95:5:0.1 for 1.5 minutes then on a 10 minute gradient to 5:95:0.1) with a flow rate of 1.0 ml/minute, detecting at 254 nm (bandwidth 10 nm).

| Ex | Compound | HPLC Ret Time (mins) | M/z [MH]+ |
|---|---|---|---|
| 16 | 2-Anilino-4-(imidazo[1,2a]pyrid-3-yl)pyrimidine | 7.26 | 288 |
| 17 | 2-2-Fluoroanilino)-4-(imidazo[1,2a]pyrid-3-yl)pyrimidine | 7.26 | 306 |
| 18 | 2-3-Bromoanilino)-4-(imidazo[1,2a]pyrid-3-yl)pyrimidine | 8.30 | 368 |
| 19 | 2-(3-Fluoroanilino)-4-(imidazo[1,2a]pyrid-3-yl)pyrimidine | 7.70 | 306 |
| 20 | 2-(3-Methoxyanilino)-4-(imidazo[1,2a]pyrid-3-yl)pyrimidine | 7.39 | 318 |
| 21 | 2-(3-Methylthioanilino)-4-(imidazo[1,2a]pyrid-3-yl)pyrimidine | 7.98 | 334 |
| 22 | 2-3-Acetylanilino)-4-(imidazo[1,2a]pyrid-3-yl)pyrimidine | 7.13 | 330 |
| 23 | 2-3-Ethylanilino)-4-(imidazo[1,2a]pyrid-3-yl)pyrimidine | 8.11 | 316 |
| 24 | 2-(4-Fluozoanilino)-4-(imidazo[1,2a]pyrid-3-yl)pyrimidine | 7.47 | 306 |
| 25 | 2-(4-Chloroanilino)-4-(imidazo[1,2a]pyrid-3-yl)pyrimidine | 8.15 | 322 |
| 26 | 2-(4-Methoxyanilino)-4-(imidazo[1,2a]pyrid-3-yl)pyrimidine | 7.02 | 318 |
| 27 | 2-(4-Benzyloxyanilino)-4-(imidazo[1,2a]pyrid-3-yl)pyrimidine | 8.65 | 394 |
| 28 | 2-[4-(Anilinosulphonyl)anilino]-4-(imidazo[1,2a]pyrid-3-yl)pyrimidine | 7.79 | 443 |
| 29 | 2-(4-Mesylanilino)-4-(imidazo[1,2a]pyrid-3-yl)pyrimidine | 6.84 | 366 |
| 30 | 2-(4-Methylthioanilino)-4-(imidazo[1,2a]pyrid-3-yl)pyrimidine | 7.89 | 334 |
| 31 | 2-(4-Methylanilino)-4-(imidazo[1,2a]pyrid-3-yl)pyrimidine | 7.65 | 302 |
| 32 | 2-(3-Sulphamoylaanilino)-4-(imidazo[1,2a]pyrid-3-yl)pyrimidine | 6.30 | 367 |
| 33 | 2-[4-Pyrimid-2-ylaminosulphonyl)anilino]-4-imidazo[1,2a]pyrid-3-yl)pyrimidine | 6.72 | 445 |
| 34 | 2-(Phenoxyanilino)-4-(imidazo[1,2a]pyrid-3-yl)pyrimidine | 8.86 | 380 |
| 35 | 2-(3-Methylanilino)-4-(imidazo[1,2a]pyrid-3-yl)pyrimidine | 7.63 | 302 |
| 36 | 2-(Indan-5-ylamino)-4-imidazo[1,2a]pyrid-3-yl)pyrimidine | 8.20 | 328 |

Example 37

2-(3-Chloroanilino)-4-(2,5-dimethylimidazo[1,2a]pyrid-3-yl)pyrimidine

2-Methylthio-4-(2,5-dimethylimidazo[1,2a]pyrid-3-yl)pyrimidine (Method 14) (200 mg, 0.74 mmol) was added to a solution of 3-chloroaniline (0.16 ml, 1.48 mmol) and sodium hydride (60 mg, 1.48 mmol) in NMP (1 ml) under nitrogen. The mixture was heated at 150° C. for 4 hours and then allowed to cool. The crude reaction mixture was loaded onto a Bond Elut column eluting with dichloromethane to remove the NMP and then with dichloromethane/methanol/methylamine (75:20:5) to elute the product. The product was further purified by chromatography eluting with ethyl acetate/hexane (8:2) and then ethyl acetate to give the title compound (22 mg, 9%). NMR: 2.27 (s, 3H), 2.61 (s, 3H), 7.01 (d, 1H), 7.12 (d, 1H), 7.30 (m, 2H), 7.56 (d, 1H), 7.62 (d, 1H), 8.57 (d, 1H), 9.41 (s 1H), 9.83 (s, 1H); m/z: 350 [MH]+.

Example 38

Following the procedure of Example 37 and using the appropriate starting materials the following compound was prepared.

| Ex | Compound | NMR | m/z [MHI]+ |
|---|---|---|---|
| 38 | 2-(3-Chloroanilino)-4-(2-methylpyrazolo[2,3a]pyrid-3-yl)pyrimidine | 2.64(s, 3H), 6.95–7.03(m, 2H), 7.17(d, 1H), 7.32(d, 1H), 7.44(dd, 1H), 7.58–7.64(m, 2H), 8.04(s, 1H), 8.57(d, 1H), 9.72(d, 1H), 9.84(s, 1H) | 336 |

Example 39

2-[4-(N-Methylsulphamoyl)anilino]-4-(imidazo[1,2a]pyrid-3-yl)pyrimidine

Toluene (4 ml) was added to a mixture of tris(dibenzideneacetone)dipalladium(0) (24 mg, 0.026 mmol), 2,2'-bis(diphenylphosphino)-1,1'-binaphthyl (21 mg, 0.034 mmol), 2-chloro-4-(imidazo[1,2a]pyrid-3-yl)pyrimidine (Method 20; 150 mg, 0.652 mmol) and 4-(N-methylsulphamoyl)aniline (Method 23; 135 mg, 0.725 mmol) under nitrogen. The flask was evacuated and refilled with nitrogen and sodium tert-butoxide (140 mg, 1.46 mmol) was added and the flask was re-evacuated and refilled with nitrogen. The mixture was heated at 100° C. for 3 hours and then allowed to cool. The mixture was diluted with ethyl acetate and washed with water. The organic phase was separated, dried and the volatiles removed by evaporation. The residue was purified by chromatography eluting with ethyl acetate/methanol (100:0 increasing in polarity to 97:3) to give the title compound 15 mg, (60%). NMR: 2.42 (d, 3H), 7.25–7.10 (m, 2H), 7.52–7.45 (m, 2H), 7.79–7.70 (m, 3H), 7.98 (d, 2H), 8.50 (d, 1H), 8.62 (s, 1H); m/z: 381 [MH]+.

Examples 40–44

Following the procedure of Example 39 and using the appropriate starting materials the following compounds were prepared.

| Ex | Compound | NMR | m/z [MH]+ | SM |
|---|---|---|---|---|
| 40[1] | 2-{4-[N-(2-Methoxyethyl) sylphamoyl]anilino}-4-(imidazo[1,2a]pyrid-3-yl) pyrimidine | 2.90(q, 2H), 3.18(s, 3H), 3.28–3.30(m, 2H), 7.16(dd, 1H), 7.48–7.54(m, 3H), 7.71–7.80(m, 3H), 7.95(d, 2H), 8.50(d, 1H), 8.62(s, 1H) | 425 | Meth 24 |
| 41[2] | 2-[(N-Propylsylphamoyl) anilino]-4-(imidazo[1,2a] pyrid-3-yl)pyrimidine | 0.80(t, 3H), 1.34–1.42(m, 2H), 2.65–2.75(m, 2H), 7.15(dd, 1H) 7.17(dd, 1H), 7.55–7.48(m, 2H), 7.70–7.79(m, 3H), 7.95(d, 2H), 8.50(d, 1H), 8.63(s, 1H) | 409 | Meth 25 |
| 42 | 2-[4-N-Cyclopropyl-sulphamoyl)anilino]-4-(imidazo[1,2a]pyrid-3-yl) pyrimidine | 0.00–0.05(m, 2H), 0.09–0.12(m, 2H), 1.70–1.75(m, 1H), 6.79(dd, 1H), 7.10–7.15(m, 2H), 7.32–7.42 (m, 4H), 7.60(d, 2H), 8.12(d, 1H), 8.28(s, 1H), 9.74(s, 1H), 9.75(s, 1H) | 405 [M-H]− | Meth 26 |
| 43 | 2-[4-(N,N-Dimethyl-carbamoy)anilino]-4-(imidazo[1,2a]pyrid-3-yl)pylimidine | 2.98(s, 6H), 7.10(dd, 1H), 7.3.8–7.50(m, 3H), 7.72–7.82(m, 3H), 8.45(d, 1H), 8.61(s, 1H), 9.82(s, 1H) | 359 | |
| 44[3] | 2-[4-(N-Methylcarbamoyl) anilino]-4-(imidazo[1,2a] pyrid-3-yl)pyrimidine | 2.78(d, 3H), 7.15(dd, 1H), 7.43 (d, 1H), 7.50(dd, 1H), 7.75–7.82 (m, 5H), 8.24(d, 1H), 8.48(d, 1H), 8.62(s, 1H), 9.90(s, 1H) | 345 | |

[1] Product was purified by chromatograpby eluting with hexane/ethyl acetate (70:30) increasing in polarity to (0:100).
[2] Product was purified by chromatography eluting with hexane/ethyl acetate (50:50) increasing in polarity to ethyl acetate/methanol (95:5).
[3] Product was purified by chromatography eluting with hexane/ethyl acetate (80:20) increasing in polarity to ethyl acetate/methanol (90:10).

Example 45
2-{4-[N-(3-Hydroxypropyl)sulphamoyl]anilino}-4-(imidazo[1,2a]pyrid-3-yl)pyrimidine 2-Anilino-4-(imidazo[1,2a]pyrid-3-yl)pyrimidine (Example 16; 100 mg, 0.347 mmol) was dissolved in thionyl chloride (4 ml) and the mixture was cooled to 5° C. Chlorosulphonic acid (0.06 ml, 0.90 mmol) was added and the was mixture stirred at 5° C. for 30 minutes, then allowed to warm to ambient temperature and stirred for 60 minutes. The mixture was then heated at reflux for 90 minutes. The volatiles were removed by evaporation and the residue azeotroped with toluene. 3-Aminopropanol (3 ml) was added to residue and the mixture stirred at ambient temperature for 30 minutes. The mixture was purified chromatography eluting with hexane/ethyl acetate (50:50) increasing in polarity to ethyl acetate/methanol (85:15). 60 mg (41%). NMR: 1.45–1.56 (m, 2H), 2.79 (q, 2H), 3.35 (q, 2H), 4.39 (t, 1H), 7.15 (dd, 1H), 7.31 (t, 1H), 7.45–7.54 (m, 2H), 7.70–7.79 (m, 3H), 7.95 (d, 2H), 8.50 (d, 1H), 8.62 (s, 1H); m/z: 423 [M–H]−.

Examples 46–50

Following the procedure of Example 45 and using the appropriate starting materials the following compounds were prepared

| Ex | Compound | NMR | m/z [MH]+ |
|---|---|---|---|
| 46 | 2-{4-[N-Cyclopropylmethyl) sulphamoyl]anilio}-4-(imidazo [1,2a]pyrid-3-yl)pyrimidine | 0.00–0.04(m, 2H), 0.25–0.32(m, 2H), 0.70–0.78(m, 1H), 2.60(t, 2H), 7.10 (dd, 1H), 7.28–7.42(m, 3H), 7.68–7.75 (m, 3H), 7.87(d, 2H), 8.42(d, 1H), 8.60 (s, 1H) | 421 |
| 47 | 2-{4-[N-(5-Hydroxypentyl) sulphamoyl]anilino}-4-(imidazo [1,2a]pyrid-3-yl)pyrimidine | 1.18–1.40(m, 8H), 2.70(t, 2H) 4.25 (br s, 1H), 7.15(dd, 1H), 7.48–7.52(m, 2H), 7.70–7.78(m, 3H), 7.95(d, 2H), 8.50(d, 1H), 8.62(s, 1H) | 453 |
| 48 | 2-(4-{N-[2-(1-Methylpyrrolidin-2-yl)ethyl]sulphamoyl}anilino)-4-(imidazo[1,2a]pyrid-3-yl) pyrimidine | 1.18–1.25(m, 2H), 1.48–1.58(m, 2H), 1.60–1.70(m, 1H), 1.90–2.00(m, 2H), 2.10(s, 3H), 2.70–2.85(m, 4H), 7.15 (dd, 1H), 7.40(s, 1H), 7.48–7.53(m, 2H), 7.70–7.80(m, 3H), 7.95(d, 2H), 8.50(d, 1H), 8.63(s, 1H) | 476 [M-H][31] |
| 49 | 2-{4-[N-(3-Diethylaminopropyl) sulphamoyl]anilino}-4-(imidazo [1,2a]pyrid-3-yl)pyrimidine | 0.86(t, 6H), 1.42(q, 2H), 2.30(q, 4H), 2.38–2.42(m, 2H), 2.75(q, 2H), 7.15 (dd, 1H), 7.42–7.55(m, 2H), 7.70–7.80 (m, 3H), 7.95(d, 2H), 8.50(d, 1H), 8.65 (s, 1H) | 480 |

-continued

| Ex | Compound | NMR | m/z [MH]+ |
|---|---|---|---|
| 50 | 2-{4-[N-(2-Isopropylaminoethyl) suphamoyl]anilino}-4-(imidazo [1,2a]pyrid-3-yl)pyrimidine | 0.87(s, 3H), 0.90(s, 3H), 2.46–2.50(m, 2H), 2.58(q, 2H), 2.80(t, 2H), 7.18(dd, 1H), 7.48–7.52(m, 2H), 7.70–7.80(m, 3H), 7.95(d, 2H), 8.50(d, 1H), 8.62(s, 1H) | 452 |

[1]Product was purified by chromatograpby eluting with hexane/ethyl acetate (70:30) increasing in polarity to (0:100)
[2]Product was purified by chromatography eluting with hexane/ethyl acetate (50:50) increasing in polarity to ethyl acetate/methanol (95:5).
[3]Product was purified by chromatography eluting with hexane/ethyl acetate (80:20) increasing in polarity to ethyl acetate/methanol (90:10).

Example 51
2-(4-{N-[3-(2-Oxopyrolidin-1-yl)propyl] sulphamoyl}anilino)-4-(imidazo[1,2a]pyrid-3-yl) pyrimidine 2-Anilino-4-(imidazo[1,2a]pyrid-3-yl)pyrimidine (Example 16; 100 mg, 0.347 mmol) was dissolved in thionyl chloride (3 ml) and the mixture was cooled to 5° C. Chlorosulphonic acid (0.06 ml, 0.90 mmol) was added and the was mixture stirred at 5° C. for 30 minutes, allowed to warm to ambient temperature and stirred for 60 minutes. The mixture was then heated at reflux for 90 minutes. The volatiles were removed by evaporation and the residue azeotroped with toluene. Pyridine (3 ml) and 3-(2-oxopyrolidin-1-yl)propylamine (3 ml) were added to the residue and the mixture was stirred at ambient temperature for one hour. The mixture was purified by chromatography eluting with hexane/ethyl acetate (50:50) increasing in polarity to ethyl acetate/methanol (80:20). 60 mg (36%). NMR: 1.51–1.60 (m, 2H), 1.80–1.90 (m, 2H), 2.13 (t, 2H), 2.70 (t, 2H), 3.10 (t, 2H), 3.20 (t, 2H), 7.16 (dd, 1H), 7.48–7.55 (m, 2H), 7.70–7.80 (m, 3H), 7.95 (d, 2H), 8.50 (d, 1H), 8.62 (s, 1H); m/z: 492 [MH]+.

Examples 52–70

Following the procedure of Example 45 and using the appropriate starting materials the following compounds were prepared

| Ex | Compound | NMR | m/z [MH]+ |
|---|---|---|---|
| 52 | 2-{4-[N-(3-Methoxypropyl) sulphamoyl]anilino}-4-imidazo [1,2a]pyrid-3-yl)pyrimidine | 1.55–1.62(m, 2H), 2.75–2.81(m, 2H), 3.12(s, 3H), 3.23–328(m, 2H), 7.15 (dd, 1H), 7.38(t, 1H), 7.55(m, 2H), 7.70–7.80(m, 3H), 7.96(d, 2H), 8.50(d, 1H), 8.62(s, 1H) | 439 |
| 53 | 2-{4-[N-(3-Isopropylaminopropyl) sulphamoyl]anilino}-4-(imidazo [1,2a]pyrid-3-yl)pyrimidine | 1.48(t, 2H), 1.88(d, 6H), 2.42(t, 2H), 2.59(m, 1H), 2.79(t, 2H), 7.15(dd, 1H), 7.48–7.55(m, 2H), 7.70–7.80(m, 3H), 7.95(d, 2H), 8.50(d, 1H), 8.62(s, 1H) | 466 |
| 54 | 2-{4-[N-(3-Imidazol-1-ylpropyl) sulphamoyl]anilino}-4-(imidazo [1,2a]pyrid-3-yl)pyrimidine | 1.80(m, 2H), 2.70(q, 2H), 3.94(t, 2H), 6.82(s, 1H), 7.08(s, 1H), 7.14(dd, 1H), 7.48–7.52(m, 4H), 7.70(d, 2H), 7.78(d, 1H), 7.98(d, 2H), 8.50(d, 1H), 8.62(s, 1H) | 473 [M-H]− |
| 55[1] | 2-{4-[N-(3-Dimethylaminopropyl)sulphamoyl]anilino}-4-(imidazo [1,2a]pyrid-3-yl)pyrimidine | 1.48(m, 2H), 2.02(s, 6H), 2.12(t, 2H), 2.78(t, 2H), 7.15(dd, 1H), 7.38(s, 1H), 7.48–7.57(m, 2H), 7.72(d, 2H), 7.78(d, 1H), 7.98(d, 2H), 8.50(d, 1H), 8.62(s, 1H) | 452 |
| 56 | 2-{4-[N-(3-Morpholinopropyl) sulphamoyl]anilino}-4-(imidazo [1,2a]pyrid-3-yl)pyrimidine | 1.52(t, 2H), 2.18–2.22(m, 6H), 2.78(t, 2H), 3.43–3.48(m, 4H), 7.15(dd, 1H), 7.38(s, 1H), 7.48–7.55(m, 2H), 7.74(d, 2H), 7.78(d, 1H), 7.98(d, 2H), 8.50(d, 1H), 8.62(s, 1H) | 494 |
| 57[1] | 2-{4-[N-(3-Aminopropyl) sulphamoyl]anilino}-4-(imidazo [1,2a]pyrid-3-yl)pyrimidine | 1.38–1.45(m, 4H), 2.79(t, 2H), 7.15 (dd, 1H), 7.48–7.56(m, 2H), 7.60–7.64 (m, 1H), 7.72(d, 2H), 7.79(d, 1H), 7.98 (d, 2H), 8.50(d, 1H), 8.62(s, 1H) | 424 |
| 58[1] | 2-(4-{N-[2-(2-Hydroxyethyl amino)ethyl]sulphamoyl}anilino)-4-(imidazo[1,2a]pyrid-3-yl) pyrimidine | 2.75(t, 2H), 2.86–2.90(m, 2H), 3.54(t, 2H), 3.60(t, 2H), 7.08(d, 2H), 7.18(dd, 1H), 7.42–7.55(m, 2H), 7.75–7.80(m, 3H), 8.00(d, 2H), 8.52(d, 1H), 8.62(s, 1H) | 454 |
| 59[2] | 2-{4-[N-(2-Imidazol-4-ylethyl) sulphamoyl]anilino)}-4-imidazo [1,2a]pyrid-3-yl)pyrimidine | 3.10(t, 2H), 3.95(t, 2H), 7.10(d, 2H), 7.40(s, 2H), 7.50(d, 2H), 7.58(d, 2H), 7.69(d, 2H), 7.75(d, 1H), 8.45(d, 1H), | |

| Ex | Compound | NMR | m/z [MH]+ |
|---|---|---|---|
| | | 8.60(s, 1H), 8.79(s, 1H), 9.75(s, 1H), 10.1(s, 1H) | |
| 60[1] | 2-{4-[N-(3-Methylaminopropyl) sulphamoyl]anilino}-4-(imidazo [1,2a]pyrid-3-yl)pyrimidine | 1.70–1.78(m, 2H), 2.66(s, 3H), 2.90(t, 2H), 3.00(t, 2H), 7.08(d, 2H), 7.18(t, 1H), 7.44(d, 2H), 7.51(m, 1H), 7.70–7.80(m, 3H), 8.02(d, 1H), 8.52(d, 1H), 8.63(s, 1H) | 436 [M-H]− |
| 61[1] | 2-{4-[N-(2-Piperazin-1-ylethyl) sulphamoyl]anilino}-4-(imidazo [1,2a]pyrid-3-yl)pyrimidine | 2.30(t, 2H), 2.40–2.43(m, 4H), 2.59(t, 2H), 2.83–2.90(m, 4H), 7.18(dd, 1H), 7.49–7.55(m, 2H), 7.68(d, 2H), 7.78(d, 1H), 8.02(d, 2H), 8.50(d, 1H), 8.62(s, 1H) | |
| 62[1] | 2-(4-{N-[3-(4-Methylpiperazin-1-yl)propyl]sulphamoyl}anilino)-4-(imidazo[1,2a]pyrid-3-yl) pyrimidine | 1.49(m, 2H), 2.10(s, 3H), 2.15–2.25 (m, 8H), 2.78(q, 2H), 3.25–3.29(m, 2H), 7.18(dd, 1H), 7.40(dd, 1H), 7.50 (d, 2H), 7.75(d, 2H), 8.80(d, 1H), 7.95 (d, 1H), 8.52(d, 1H), 8.65(s, 1H) | 507 |
| 63[1] | 2-(4-{N-[2-(2-Diethylaminoethyl-amino)ethyl]sulphamoyl}anilino)-4-(imidazo[1,2a]pyrid-3-yl) pyrimidine | 0.93(t, 6H), 2.40–2.58(m, 4H), 2.62(t, 2H), 2.84(t, 2H), 3.20–3.40(m, 4H), 7.10(d, 1H), 7.18(dd, 1H), 7.42–7.50 (m, 3H), 7.72–7.80(m, 3H), 7.98(d, 2H), 8.50(d, 1H), 8.62(s, 1H) | 509 |
| 64[1] | 2-{4-[N-(2,3-Dihydroxypropyl) sylphamoyl]anilino}-4-(imidazo [1,2a]pyrid-3-yl)pyrimidine | 2.66(m, 1H), 2.86(m, 1H), 3.21–3.30 (m, 2H), 3.46(m, 1H), 4.49(t, 1H), 4.70 (d, 1H), 7.18(dd, 1H), 7.24(dd, 1H), 7.48–7.52(m, 2H), 7.70–7.80(m, 3H), 7.98(d, 2H), 8.50(d, 1H), 8.62(s, 1H) | 441 |
| 65 | 2-{4-[N-(2-Dimethylaminoethyl) sulphamoyl)anilino}-4-(imidazo [1,2a]pyrid-3-yl)pyrimidine | 2.08(s, 6H), 2.24(t, 2H), 2.82(t, 2H), 1.7(dd, 1H), 7.30(s, 1H), 7.44–7.54(m, 2H), 7.70–7.80(m, 3H), 7.95(d, 2H), 8.50(d, 1H), 8.63(s, 1H) | 438 |
| 66 | 2-{4-[N-(2-Morpholinoethyl) sylphamoyl]anilino}-4-(imidazo [1,2a]pyrid-3-yl)pyrimidine | 2.34–2.45(m, 6H), 2.87–2.95(m, 2H), 3.46–3.60(m, 4H), 7.09(d, 2H), 7.18 (dd, 1H), 7.42–7.50(m, 3H), 7.74–7.80 (m, 2H), 7.98(d, 2H), 8.50(d, 1H), 8.62 (s, 1H) | 478 [M-H]− |
| 67 | 2-{4-[N-(2-Pyrrolidin-1-ylethyl) sylphamoyl]anilino}-4-(imidazo [1,2a]pyrid-3-yl)pyrimidine | 1.64–1.74(m, 4H), 2.52–2.64(m, 6H), 2.87–2.92(m, 2H), 7.18(dd, 1H), 7.44–7.54(m, 3H), 7.72–7.80(m, 3H), 7.98(d, 2H), 8.50(d, 1H), 8.62(s, 1H) | 464 |
| 68 | 2-{4-[N-(2-Methylaminoethyl) sulphamoyl]anilino}-4-(imidazo [1,2a]pyrid-3-yl)pyrimidine | 2.61–2.64(m, 2H), 2.68(s, 3H), 2.90(t, 2H), 7.18(dd, 1H), 7.48–7.58(m, 2H), 7.68–7.78(m, 4H), 7.95(d, 1H), 8.00(d, 1H), 8.51(d, 2H), 8.64(s, 1H) | 424 |
| 69 | 2-{4-[N-2-Piperidin-1-ylethyl) sulphamoyl)anilino}4-(imidazo [1,2a]pyrid-3-yl)pyrimidine | 1.28–1.40(m, 2H), 1.40–1.58(m, 4H), 2.20–2.50(m, 6H), 2.84–2.92(m, 2H), 7.18(dd, 1H), 7.48–7.53(d, 2H), 7.72–7.80(m, 3H), 7.98(d, 2H), 8.50(d, 1H), 8.62(s, 1H) | 478 |
| 70 | 2-{4-[N-(2-Diethylaminoethyl) sylphamoyl]anilino}-4-(imidazo [1,2a]pyrid-3-yl)pyrimidine | 0.86(t, 6H), 2.32–2.42(m, 6H), 2.79(t, 2H), 7.18(dd, 1H), 7.23(s, 1H), 7.48–7.52(m, 2H), 7.70–7.80(m, 3H), 7.98(d, 2H), 8.50(d, 1H), 8.62(s, 1H) | 466 |

[1]Product was purified by chromatography eluting with ethyl acetate/methanol (100:0) increasing in polarity to (70:30)
[2]Product was isolated without chromatography by trituration from reaction mixture with dichloromethane and methanol.

Example 71

2-{4-[N-(3-Imidazol-1-ylpropyl)carbamoyl]anilino}-4-(imidazo[1,2a]pyrid-3-yl)pyrimidine Toluene (10 ml) was added to 2-amino-4-(imidazo[1,2a]pyrid-3-yl)pyrimidine (Method 22; 200 mg, 0.95 mmol), 1-[34-bromobenzoylamino)propyl]imidazole (Method 27; 350 mg, 1.14 mmol), tris(dibenzideneacetone)dipalladium (0) (43 mg, 0.047 mmol) and 2,2'-bis(diphenylphosphino)-1,1'-binaphthyl (28 mg, 0.046 mmol) under nitrogen. Sodium tert-butoxide (218 mg, 0.0023 mmol) was added, the reaction mixture was flushed thoroughly with nitrogen and then heated at 100° C. for 24 hours. The volatiles were removed by evaporation and the residue was purified by chromatography eluting with hexane/ethyl acetate (50:50) increasing in polarity to ethyl acetate/methanol (95:5) to give the title compound 99 mg (24%). NMR: 1.90–2.00 (m, 2H), 3.22 (q, 2H), 4.02 (t, 2H), 6.86 (s, 1H), 7.16 (dd, 1H), 7.21 (s, 1H), 7.42–7.55 (m, 2H), 6.80 (s, 3H), 7.78 (d, 1H), 7.83 (s, 4H), 8.38 (t, 1H), 8.48 (d, 1H), 8.62 (s, 1H), 9.92 (s, 1H); m/z: 439 [MH]+.

Examples 72–74

Following the procedure of Example 71 and using the appropriate starting materials the following compounds were prepared.

| Ex | Compound | NMR | m/z [MH]+ | SM |
|---|---|---|---|---|
| 72[1] | 2-(4-{N-[3-(2-Oxopyrolidin-1-yl propyl]carbamoyl} anilino)-4-imidazo[1,2a]pyrid-3-yl)pyrimidine | 1.70(quin, 2H), 1.90(quin, 2H), 2.21(t, 2H), 3.18–3.24(m, 4H), 3.30–3.38(m, 2H), 7.15(dd, 1H), 7.42–7.52(m, 2H), 7.78(d, 1H), 7.82(s, 4H), 8.27(t, 1H), 8.49(d, 1H), 8.62(s, 1H), 9.90(s, 1H). | 456 | Meth 28 |
| 73[2] | 2-{3-Chloro-4-[N-(2-methoxyethyl)sulphamoyl] anilino}-4-(imidazo[1,2a] pyrid-3-yl)pyrimidine | 3.00(q, 2H), 3.12(s, 3H), 3.25–3.30(m, 2H), 7.18(dd, 1H), 7.50–7.58(m, 2H), 7.68(t, 1H), 7.75–7.80(m, 2H), 7.87(s, 1H), 8.22(s, 1H), 8.55(d, 1H), 8.64(s, 1H) | 459 | |
| 74[3] | 2-[3-Chlor-4-N-propyl sylphamoyl)anilino]-4-(imidazo[1,2a]pyrid-3-yl) pyrimidine | 0.80(t, 3H), 1.38(m, 2H), 2.79(q, 2H), 7.18(dd, 1H), 7.48–7.55(m, 2H), 7.66(dd, 1H), 7.78(dd 2H), 7.92(d, 1H), 8.25(s, 1H), 8.55(d, 1H), 8.68(s, 1H), 10.10(d, 1H), 10.26(s, 1H) | 443 | |

[1] Reaction heated at 100° C. for 48 hours and purified by chromatography eluting with dichloromethane/methanol (90:10)
[2] Starting from 2,4-dichloro-1-(2-methoxyethylsylphamoyl)benzene (Method 29)
[3] Starting from 2,4-dichloro-1-(1-propylsulphamoyl)benzene (Method 30)

Example 75

2-(3-Methyl-4-sulphamoylanilino)-4-(imidazo[1,2a]pyrid-3-yl)pyrimidine 2-(3-Methylanilino)-4-(imidazo[1,2a]pyrid-3-yl) pyrimidine (Example 35; 80 mg, 0.266 mmol) was treated as described in Example 45 but with 2M ethanolic ammonia to give the title compound (6 mg, 17%). NMR: 2.60 (s, 3H), 6.95–7.20 (m, 4H), 7.46–7.50 (m, 2H), 7.70–7.80 (m, 4H), 8.50 (d, 1H), 8.62 (s, 1H), 9.87 (s, 1H); m/z: 381 [MH]+.

Examples 76–78

Following the procedure of Example 75 and using the appropriate starting materials the following compounds were prepared.

| Ex | Compound | NMR | m/z [MH]+ |
|---|---|---|---|
| 76 | 2-{3-Methyl-4-[N-(2-methoxy-ethyl)sylphamoyl]anilino}-4-(imidazo[1,2a]pyrid-3-yl) pyrimidine | 2.55(s, 3H), 2.91(q, 2H), 3.11(s, 3H), 3.22(t, 2H), 7.12(dd, 1H), 7.44–7.55 (m, 3H), 7.74–7.80(m, 4H), 8.50(d, 1H), 8.62(s, 1H), 9.98(s, 1H) | 439 |
| 77 | 2-{3-Methyl-4-[N-3-morpholino-propyl)sulphamoyl]anilino}-4-(imidazo[1,2a]pyrid-3-yl) pyrimidine | 1.49(m, 2H), 2.13–2.20(m, 4H), 3.24–3.32(m, 2H), 2.58(s, 3H), 2.80(t, 2H), 3.42–3.48(m, 4H), 7.12(dd, 1H), 7.48–7.53(m, 2H), 7.75–7.80(m, 4H), 8.50(d, 1H), 8.62(s, 1H) | 508 |
| 78 | 2-{3-Methyl-4-[N-(2-morpholino-ethyl)sulphamoyl]anilino}-4-(imidazo[1,2a]pyrid-3-yl) pyrimidine | 2.18–2.21(m, 4H), 2.30–3.38(m, 2H), 2.59(s, 3H), 2.87(t, 2H), 3.42–3A8(m, 4H), 7.12(dd, 1H), 7.42–7.55(m, 3H), 7.75–7.80(m, 4H), 8.50(d, 1H), 8.62(s, 1H), 9.98(s, 1H) | 494 |

Example 79

5-Bromo-2-(4-sulphamoylanilino)-4-(imidazo[1,2a]pyrid-3-yl)pyrimidine

2-Anilino-5-bromo-4-(imidazo[1,2a]pyrid-3-yl) pyrimidine (Example 97; 73 mg, 0.2 mmol) was treated as described in Example 45 but with 2M ethanolic ammonia to give the title compound (18 mg, 21%). NMR: 7.12 (dd, 1H), 7.19 (s, 2H), 7.53 (dd, 2H), 7.72 (d, 2H), 7.79 (d, 1H), 7.84 (d, 2H), 8.76 (s, 1H), 8.78 (s, 1H), 9.62 (s, 1H); m/z: 445 [MH]$^+$.

Examples 80–81

Following the procedure of Example 79 and using the appropriate starting materials the following compounds were prepared.

| Ex | Compound | NMR | m/z [MH]$^+$ |
|---|---|---|---|
| 80 | 5-Bromo-2-{4-[N-(2-methoxy-ethyl)sulphamoyl]anilino}-4-(imidazo[1,2a]pyrid-3-yl) pyrimidine | 2.90(m, 2H), 3.18(s, 3H), 3.28(q, 2H), 7.10(dd, 1H), 7.48–7.58(m, 2H), 7.70 (d, 2H), 7.79(d, 1H), 7.86(d, 2H), 8.76 (s, 1H), 8.78(s, 1H), 9.60(d, 1H) | 503 |
| 81 | 5-Bromo-2-{4-[N-(2-dimethyl-aminoethyl)sulphamoyl]anilino}-4-(imidazo[1,2a]pyrid-3-yl) pyrimidine | 2.06(s, 6H), 2.25(t, 2H), 2.82(t, 2H), 7.15(dd, 1H), 7.30(s, 1H), 7.55(dd, 1H), 7.72(d, 2H), 7.80(d, 1H), 7.90(d, 2H), 8.75(s, 1H), 9.80(s, [H), 9.65(d, 1H), 10.28(s, 1H) | 516 |
| 82[1] | 5-Bromo-2-{4-(N-(3-dimethyl-aminopropyl)sulphamoyl]anilino}-4-(imidazo[1,2a]pyrid-3-yl) pyrimidine | 1.70–1.80(m, 2H), 1.87–1.98(m, 2H), 2.62(d, 6H), 2.79(q, 2H), 7.12(dd, 1H), 7.55(dd, 1H), 7.59(dd, 1H), 7.70 (d, 2H), 7.79(d, 1H), 7.90(d, 2H), 8.78 (s, 1H), 8.79(s, 1H), 9.64(d, 1H), 10.32 (s, 1H) | 530 |

[1]Product was purified by chromatography eluting with hexane/ethyl acetate (50:50) increasing in polarity to ethyl acetate/methanol (70:30)

Example 83

2-{4-[N-(2-Methoxyethyl)sulphamoyl]anilino}-4-(5-bromoimidazo[1,2a]pyrid-3-yl) pyrimidine 2-Anilino-4-(5-bromoimidazo[1,2a]pyrid-3-yl) pyrimidine (Example 98; 70 mg, 0.2 mmol) was treated with 2-methoxyethylamine under the conditions described in Example 51 to give the title compound 23 mg (25%). NMR: 2.90 (q, 2H), 3.18 (s, 3H), 3.26–3.29 (m, 2H), 7.49–7.54 (m, 2H), 7.60 (dd, 1H), 7.74–7.78 (m, 3H), 7.90 (d, 1H), 8.54 (d, 1H), 8.62 (s, 1H); m/z: 503 [MH]$^+$.

Example 84

2-{4-[N-(2-Methoxyethyl)sulphamoyl]anilino}-4-(5-phenylthioimidazo[1,2a]pyrid-3-yl) pyrimidine Sodium hydride (80 mg of a 60% suspension in mineral oil, 2.0 mmol) was added to thiophenol (0.102 ml, 1.0 mmol) in NMP (4 ml) and the mixture was stirred for 30 minutes. 2-[4N-(2-Methoxyethyl)sulphamoyl)anilino]-4-(5-bromoimidazo[1,2a]pyrid-3-yl)pyrimidine (Example 83; 100 mg, 0.19 mmol) in NMP (1 ml) was added and the mixture was heated at 150° C. for 18 hours. The mixture was allowed to cool, diluted with water and extracted with ethyl acetate. The extracts were washed with water, dried and the volatiles removed by evaporation. The residue was triturated with ether and collected by filtration to give the title compound 20 mg (20%). NMR: 2.85 (q, 2H), 3.15 (s, 3H), 3.24 (q, 2H), 7.10–7.30 (m, 5H), 7.38 (d, 1H), 7.46 (dd, 1H), 7.52 (d, 1H), 7.75 (d, 2H), 7.79 (d, 1H), 7.92 (d, 2H), 8.54 (d, 1H), 8.66 (s, 1H); m/z: 533 [MH]$^+$.

Examples 85–88

Following the procedure of Example 84 and using the appropriate starting materials the following compounds were prepared.

| Ex | Compound | NMR | m/z [MH]$^+$ |
|---|---|---|---|
| 85[1] | 2-{4-[N-(2-Methoxyethyl) sulphamoyl]anilino}-4-(5-ethyl-thioimidazo[1,2a]pyrid-3-yl) pyrimidine | 1.18(t, 3H), 2.84–2.95(m, 4H), 3.18(s, 3H), 3.26–3.30(m, 2H), 7.49–7.58(m, 3H), 7.71–7.79(m, 4H), 7.90(d, 2H), 8.50–8.55(m, 1H), 8.60(s, 1H), 8.89(s, 1H) | 485 |
| 86[1] | 2-{4-[N-(2-Methoxyethyl) sylphamoyl[anilino}-4-[5-(2-hydroxyethylthio)imidazo[1,2a] pyrid-3-yl]pyrimidine | 2.90(t, 2H), 3.05(t, 2H), 3.20(s, 3H), 3.32(t, 2H), 3.60(q, 2H), 5.00(t, 1H), 7.45(dd, 1H), 7.50(d, 1H), 7.58(d, 1H), 7.70–7.79(m, 3H), 7.95(d, 2H), 8.50(d, 1H), 8.59(s, 1H), 9.95(s, 1H), 10.05(s, 1H) | 501 |
| 87[2] | 2-{4-[N-(2-Methoxyethyl) sulphamoyl)anilino}-4-[5-(thien-2-ylthio)imidazo[1,2a]pyrid-3-yl]pyrimidine | 2.90(m, 2H), 3.15(s, 3H), 3.24(q, 2H), 7.08–7.10(m, 1H), 7.32(d, 1H), 7.42(d, 1H), 7.50(d, 1H), 7.70–7.80(m, 4H), 7.94(d, 2H), 8.52(d, 1H), 8.63(s, 1H) | 539 |

| Ex | Compound | NMR | m/z [MH]+ |
|---|---|---|---|
| 88[3] | 2-{4-[N-(2-Methoxyethyl) sulphamoyl]anilino}-4-[5-(2-dimethylaminoethylthio)imidazo [1,2a]pyrid-3-yl]pyrimidine | 2.15(s, 6H), 2.40–2.50(m, 2H), 2.90(q, 2H), 3.09(t, 2H), 3.20(s, 3H), 3.28–3.32(m, 2H), 7.48–7.58(m, 3H), 7.72–7.80(m, 3H), 7.95(d, 2H), 8.51(d, 1H), 8.60(s, 1H), 9.90(s, 1H), 10.11(s, 1H) | 528 |

[1]Product was purified by chromatography eluting with ethyl acetate/methanol (100:0) increasing in polarity to (95:5)
[2]Product was purified by chromatography eluting with ethyl acetate
[3]Product was purified by chromatography eluting with ethyl acetate/methanol (100:0) increasing in polarity to (70:30)

Example 89

2-{4-[N-(2-Methoxyethyl)sulphamoyl]anilino}-4-(5-cyanoimidazo[1,2a]pyrid-3-yl)pyrimidine 2-{4-[N-(2-Methoxyethyl)sulphamoyl]anilino}-4-(5-bromoimidazo[1,2a]pyrid-3-yl) pyrimidine (Example 83; 87 mg, 0.17 mmol), tetraethylammonium cyanide (27 mg, 0.17 mmol), diphenylphosphinoferrocene (23 mg, 0.03 mmol) copper (I) cyanide (62 mg, 0.7 mmol) and tris (dibenzideneacetone)dipalladium(0) (7 mg, 0.008 mmol) in dry dioxane (6 ml) was flushed thoroughly with nitrogen and heated at reflux for 48 hours. The volatiles were removed by evaporation and the residue was purified by chromatography eluting with hexane/ethyl acetate (50:50) increasing in polarity to (0:100) to give the title compound 16 mg (21%). NMR. 2.90 (q, 2H), 3.15 (s, 3H), 3.25–3.30 (m, 2H), 7.42 (dd, 1H), 7.58 (d, 1H), 7.72–7.78 (m, 3H), 7.90–7.98 (m, 3H), 8.59 (d, 1H), 8.40 (s, 1H), 10.23 (s, 1H), 10.53 (s, 1H); m/z: 447 [M-H]−.

Example 90

2-{4-[N-(3-Dimethylaminopropyl)sulphamoyl]anilino}-4-(5-bromoimidazo[1,2a]pyrid-3-yl) pyrimidine 2-Anilino-4-(5-bromoimidazo[1,2a]pyrid-3-yl) pyrimidine (Example 98; 20 mg, 0.52 mmol) was treated as described in Example 45 but treated with 3-dimethylaminopropyl-amine to give the title compound (92 mg, 34%). NMR: 1.48–1.58 (m, 2H), 2.10 (s, 6H), 2.20–2.28 (m, 2H), 2.72–2.80 (m, 2H), 7.08 (d, 1H), 7.40748 (m, 2H), 7.51 (d, 1H), 7.61 (dd, 1H), 7.71–7.78 (m, 3H), 7.90 (d, 2H), 8.55 (d, 1H), 8.64 (s, 1H); m/z: 530 [MH]+.

Example 91

5-(2-Hydroxyethylthio)-2-{4-[N-(2-Methoxyethyl) sulphamoyl]anilino}-4-(imidazo[1,2a]pyrid-3-yl) pyrimidine Sodium hydride (158 mg of a 60% suspension in mineral oil, 4.0 mmol) was added to 2-mercaptoethanol (0.139 ml, 2.0 mmol) in NW (4 ml) and the mixture was stirred for 30 minutes. 5-Bromo-2-{4-[N-(2-methoxyethyl)sulphamoyl] anilino}-4-(imidazo[1,2a]pyrid-3-yl) pyrimidine (Example 80; 100 mg, 0.19 mmol) in NMP (1 ml) was added and the mixture was heated at 120° C. for 3 hours. The mixture was allowed to cool, diluted with water, neutralised with 2M hydrochloric acid and extracted with ethyl acetate. The extracts were washed with water and brine, dried and the volatiles removed by evaporation. The residue was purified by chromatography eluting with hexane/ethyl acetate (50:50) increasing in polarity to ethyl acetate/methanol (95:5) to give the title compound 39 mg (20%). NMR: 2.85–2.98 (m, 4H), 3.15 (s, 3H), 3.24–3.30 (m, 2l), 3.51 (q, 2l), 4.82 (t, 1H), 7.10 (dd, 1H), 7.45–7.54 (m, 2H), 7.70 (d, 2l), 7.78 (d, 1H), 7.90 (d, 2l), 8.70 (s, 1H), 8.85 (s, 1H), 9.72 (d, 1H), 10.18 (s, 1H); m/z: 501 [MH]+.

Example 92

2-(4-{N-[3-(tert-Butoxycarbonylamino)propyl] sulphamoyl}anilino)-4-(imidazo[1,2a]pyrid-3-yl) pyrimidine 2-Anilino-4-(imidazo[1,2a]pyrid-3-yl)pyrimidine (Example 16; 290 mg, 11.0 mmol) was dissolved in thionyl chloride (6 ml) and the mixture was cooled to 0° C. Chlorosulphonic acid (0.266 ml, 4.0 mmol) was added slowly and the mixture was stirred at 0° C. for 30 minutes, allowed to warm to ambient temperature stirred for two hours and then heated at reflux for one hour. The volatiles were removed by evaporation. The residue was dissolved in dry pyridine (5 ml) and the resulting solution added slowly to a solution of 3-(tert-butoxycarbonylamino)propylamine (0.209 ml, 1.2 mmol) and diethylmethylamine (1.21 ml, 10 mmol) in pyridine (10 m]) and cooled to 0° C. under nitrogen. The mixture was stirred at 0° C. for one hour, then at ambient temperature for two hours. The volatiles were removed by evaporation and the residue azeotroped with water. The residue was triturated with water, collected by filtration, and then purified by chromatography eluting with dichloromethane/methanol (95:5) increasing in polarity to (90:10) to give the title compound 207 mg, (40%). NMR: 1.30 (s, 9H), 1.50 (quin, 2H), 2.67 (m, 2H), 2.85 (m, 2H), 7.38 (m, 2H), 7.58 (d, 1H), 7.68 (d, 1H), 7.70 (d, 2H), 7.89 (d, 1H), 7.95 (d, 2H), 8.58 (d, 1H), 8.80 (s, 1H); m/z: 524 [MH]+.

Example 93

2-(4-{N-[3-(Benzyloxycarbonylamino)propyl] sulphamoyl}anilino)-4-(imidazo[1,2a]pyrid-3-yl) pyrimidine 2-Anilino-4-(imidazo[1,2a]pyrid-3-yl)pyrimidine (Example 16; 290 mg, 1.0 mmol) and 3-(benzyloxycarbonylamino)propylamine (0.294 ml, 1.2 mmol) were treated as described in Example 92 to give the title compound 212 mg, (38%). NMR: 1.50 (quin, 2H), 2.70 (q, 2H), 2.98 (dd, 2H), 4.98 (s, 2H), 7.12–7.15 (m, [4]H), 7.18 (t, 2H), 7.19 (t, 1H), 7.75 (d, 2H), 7.79 (d, 1H), 7.90 (d, 2H), 8.50 (d, 1H), 8.60 (s, 1H); m/z: 558 [MH]+.

Example 94

2-[4-(2-Diethylaminoethoxy)anilino]4-(6-phenylimidazo[1,2a]pyrid-3-yl)pyrimidine 3-(3-Dimethylaminoprop-2-en-1-oyl)-6-phenylimidazo [1,2a]pyridine (Method 38; 50 mg, 0.17 mmol) was added to a solution of 4-(2-diethylaminoethoxy)phenylguanidine (Method 42; 60 mg, 0.19 mmol) and sodium methoxide (11 mg, 0.21 mmol) in n-butanol (1.5 ml) and the mixture was heated at 115° C. for 15 hours. The volatiles were removed by evaporation and the residue purified by chromatography eluting with hexane/ethyl acetate (50:50) increasing in polarity to ethyl acetate/methanol (80:20) to give the title compound (5 mg, 6%). NMR: 1.07 (t, 6H), 2.64 (q, 4H), 2.92 (t, 2H), 4.10 (t, 2H), 6.98 (d, 2H), 7.08 (m, 2H), 7.15 (d, 1H), 737–7.60 (m, 4H), 7.70 (d, 2H), 7.92 (s, 1H), 8.30 (s, 1H), 8.35 (d, 1H), 9.80 (d, 1H); m/z: 479 [MH]+.

Example 95
4-(6-Methoxy-2-methylimidazo[1,2a]pyrid-3-yl)-2-(4-sulphamoylanilino)pyrimidine 3-(3-Dimethylaminoprop-2-en-1-oyl)-2-methyl-6-methoxyimidazo[1,2a]pyridine (Method 39; 862 mg, 3.51 mmol) was added to a solution of 4-sulphamoylphenylguanidine (Method 41; 1.5 g, 7.0 mmol) and sodium methoxide (758 mg, 14 mmol) in N-butanol (4 ml) and the mixture was heated at reflux for 24 hours. The mixture was allowed to cool and the resulting precipitate collected by filtration and purified by chromatography eluting with hexane/ethyl acetate (50:50) increasing in polarity to ethyl acetate/methanol (90:10) to give the title compound. NMR: 2.60 (s, 3H), 3.88 (s, 3H), 6.70 (dd, 1H), 7.03 (d, 1H), 7.12 (d, 1H), 7.18 (s, 2H), 7.75 (d, 2H), 7.90 (d, 2H), 8.52 (d, 1H), 9.68 (d, 1H), 9.97 (s, 1H); m/z: 411 [MH]+.

Example 96
2-(3-Chloroanilino)-4-(pyrazolo[2,3a]pyrid-3-yl) pyrimidine

Dry n-butanol (6.0 ml) was added to a mixture of 33-dimethylaminoprop-2-en-1-oyl)-2-methylpyrazolo[2,3a]pyridine (Method 18; 180 mg, 0.84 mmol), 3-chlorophenylguanidine (142 mg, 0.84 mmol) and sodium hydride (67 mg of a 60% dispersion in mineral oil, 1.67 mmol) and the mixture was heated under nitrogen at 125° C. for 7 hours. The volatiles were removed by evaporation and the residue was triturated with a mixture of ether and distilled water. The precipitated solid was collected by filtration, washed with ether and distilled water and dried to give the title compound (78 mg, 29%). NMR: 7.00 (d, 1H), 7.10 (t, 1H), 7.35 (m, 2H), 7.50 (t, 1H), 7.60 (d, 2H), 8.08 (s, 1H), 8.43 (d, 1H), 8.70 (d, 1H), 8.82 (d, 21), 9.68 (s, 1H); m/z: 322 [MH]+.

Example 97
2-Anilino-5-bromo-4-(imidazo[1,2a]pyrid-3-yl)pyrimidine

2-Amino-5-bromo-4-(imidazo[1,2a]pyrid-3-yl)pyrimidine (Method 31; 200 mg, 0.67 mmol) and bromobenzene (0.08 ml, 0.76 mmol) were treated as described in Example 71 and the product was purified by chromatography eluting with hexane/ethyl acetate (50:50) increasing in polarity to (0:100) to give the title compound. NMR: 6.98–7.10 (m, 2H), 7.30 (dd, 2H), 7.50 (dd, 1H), 7.66 (d, 2H), 7.78 (d, 1H), 8.64 (s, 2H), 8.72 (s, 1H), 9.01 (d, 1H), 9.82 (s, 1H).

Example 98
2-Anilino-4-(5-bromoimidazo[1,2a]pyrid-3-yl)pyrimidine

2-Amino-4-(5-bromoimidazo[1,2a]pyrid-3-yl)pyrimidine (Method 35; 1.0 g, 3.4 mmol), and bromobenzene (4.36 ml, 4.1 mmol) were treated as described in Example 71 and the product purified by chromatography eluting with ethyl acetate/methanol (98:2) increasing in polarity to (90:10) to give the title compound 70 mg (6%) NMR: 7.00 (dd, 1H), 7.30–7.40 (m, 4H), 7.59 (d, 1H), 7.65–7.75 (m, 3H), 8.42 (d, 1H), 8.60 (s, 1H), 9.70 (s, 1H); m/z: 364 [M–H]−.

Preparation of Starting Materials

The starting materials for the Examples above are either commercially available or are readily prepared by standard methods from known materials. For example the following reactions are illustrations but not limitations of the preparation of some of the starting materials used in the above reactions.

Method 1
4-(2-Methylimidazo[1,2a]pyrid-3-yl)-2-methylthiopyrimidine

A mixture of 3-(3-dimethylaminoprop-2-en-1-oyl)-2-methylimidazo[1,2a]pyridine (Method 2) (20 g, 87 mmol), thiourea (6.52 g, 86 mmol) and sodium methoxide (1.19 g, 22 mmol) in butanol (220 ml) was heated at 85° C. for two hours under nitrogen. Methyl iodide (2 ml, 32 mmol) was added and the mixture heated at 85° C. for a further 1 hour. Methanol was added and the volatiles were removed by evaporation. The residue was purified by chromatography eluting with ethyl acetate/methanol (100:0 increasing in polarity to 97:31) to give the title compound (16 g, 71%). NMR. 2.59 (s, 1H), 2.62 (s, 3H), 7.10 (dd, 1H), 7.40 (dd, 1H), 7.42 (d, 1H), 7.63 (d, 1H), 8.62 (s, 1H), 9.54 (d, 1H), m/z: 257 [MH]+.

Method 2
3-(3-Dimethylaminoprop-2-en-1 oyl)-2-methylimidazo[1,2a]pyridine

A mixture of 3-acetyl-2-methylimidazo[1,2a]pyridine (Method 3) (40 g, 0.23 mol) and DMFDMA (200 ml) was heated at reflux under nitrogen for 4 days. The volatiles were removed by evaporation, the residue was triturated with hot ether and the solid product collected by filtration to give the title compound (21 g, 40%). NMR: 2.64 (s, 3H), 3.29 (s, 6H). 5.50 (d, 1H), 7.00 (dd, 1H), 7.38 (dd, 1H), 7.54 (d, 1H), 7.70 (d, 1H), 9.55 (d, 1H), m/z: 230 [MH]+.

Method 3
3-Acetyl-2-methylimidazo[1,2a]pyridine

A mixture of 2-aminopyridine (60 g, 0.64 mol) and 3-chloro-2,4-pentanedione (101.4 g, 0.75 mol) in ether (450 ml) and THF (750 ml) were heated at reflux for 12 hours, then left to stand at ambient temperature for 18 hours. The solvent was removed by evaporation and the residue was purified by chromatography eluting with dichloromethane/hexane (1:1) increasing in polarity to dichloromethane/methanol (98:2). The purified product was triturated with hexane to give the title compound (46.2 g, 40%). NMR: 2.55 (s, 3H), 2.68 (s, 3H), 7.15 (dd, 1H), 7.56 (dd, 1H), 7.64 (d, 1H), 9.58 (d, 1H), m/z: 175 [MH]+.

Method 4
4-(Imidazo[1,2a]pyrid-3-yl)-2-methylthiopyrimidine

A mixture of 3-(3-dimethylaminoprop-2-en-1-oyl) imidazo[1,2a]pyridine (Method 5) (0.90 g, 4.2 mmol), thiourea (0.32 g, 4.2 mmol) and sodium methoxide (0.34 g, 6.3 mmol) was heated at 85° C. in N-butanol (10 ml) for 2 hours. The mixture was allowed to cool to 30° C., methyl iodide (0.6 ml, 9.6 mmol) was added dropwise and stirring continued for a further 3 hours. The volatiles were removed by evaporation and the residue purified by chromatography, eluting with ethyl acetate/methanol (100:0 increasing in polarity to 97:3) to give the title compound (0.94 g, 93%). NMR: 2.61 (s, 3H), 7.22 (dd, 1H), 7.54 (dd, 1H), 7.72 (d, 1H), 7.77 (d, 1H), 8.56 (d, 1H), 8.66 (s, 1H), 9.83 (d, 1H); m/z: 243 [MH]+.

Method 5
3-(3-Dimethylaminoprop-2-en-1-oyl)imidazo[1,2a]pyridine

A mixture of crude 3-acetylimidazo[1,2a]pyridine (Method 6) (3.3 g, 19.1 mmol) and DMFDMA (40 ml) was heated at reflux for 60 hours. The mixture was allowed to cool, the volatiles were removed by evaporation and the residue triturated with hot ether. The solid product was collected by filtration to give the title compound 2.29 g, 52%. NMR: 2.90 (br s, 3H), 3.10 (br s, 3H), 5.81 (d, 1H), 7.09 (dd, 1H), 7.42 (dd, 1H), 7.65 (d, 1H), 7.70 (d, 1H), 8.43 (s, 1H), 9.72 (d, 1H); m/z: 216 [MH]$^+$.

Method 6

3-Acetylimidazo[1,2a]pyridine

Aluminium chloride (20.4 g, 153.2 mmol) was added in small portions to a solution of imidazo[1,2]pyridine (8.9, 75.7 mmol) in dichloromethane (150 ml) cooled at 5° C. The mixture was then allowed to warm to ambient temperature and stirred for 1 hour and then heated to reflux. Acetic anhydride (5.11 ml, 53.9 mmol) was then added slowly over 30 minutes and the mixture heated at reflux for further 90 minutes. The mixture was allowed to cool, the solvent was removed by evaporation and ice/water added to the residue. The aqueous mixture was made alkaline with 2M aqueous sodium hydroxide solution and extracted with ethyl acetate. The combined extracts were dried and the volatiles removed by evaporation to give a brown oil. This oil was shown to consist of ~35% of the title compound, the remainder being imidazo[1,2a]pyridine. This mixture was used without further purification. NMR. 2.57 (s, 3H), 7.22 (dd, 1H), 7.61 (dd, 1H), 7.79 (d, 1H), 8.60 (s, 1H), 9.52 (d, 1H).

Method 7

4-(3,5-Dioxapiperidin-1-yl)sulphonylaniline

A mixture of 1-(3,5-dioxapiperidin-1-yl)sulphonyl-4-nitrobenzene (Method 8) (500 mg, 1.82 mmol) and 10% palladium on charcoal catalyst (150 mg) in ethanol (25 ml) and ethyl acetate (25 ml) was stirred under an atmosphere of hydrogen for 3 hours. The catalyst was removed by filtration through diatomaceous earth and the filter pad was washed with ethanol and ethyl acetate. The volatiles were removed from the filtrate by evaporation and the residue triturated with ether and hexane to give the tide compound (395 mg, 88%). NMR: 4.90 (s, 2H) 5.10 (s, 4H), 6.02 (s, 2H), 6.58 (d, 2H), 7.50 (d, 2H).

Method 6

1-(3,5-Dioxapiperidin-1-yl)sulphonyl-4-nitrobenzene

4-Nitrobenzenesulphonamide (2.02 g, 10 mmol) was added to a solution of 1,3,5-trioxane (1.96 g, 20 mmol) in acetic acid (5 ml). The mixture was cooled for 5 minutes ated methanesulphonic acid (10 ml) was added slowly. The mixture was then stirred at 35° C. for 20 minutes, cooled to 0° C., diluted with water and extracted with ethyl acetate. The combined extracts were washed twice with water and twice with 5% aqueous sodium hydrogen carbonate solution, then dried and the volatiles removed by evaporation. The residue was recrystallized from ethanol to give the title compound (955 mg, 35%). NMR: 4.87 (s, 2H), 5.30 (s, 4H), 8.20 (d, 2H), 8.42 (d, 2H).

Method 9

4-(2-Diethylaminoethoxy)aniline

A mixture of 4-(2-diethylaminoethoxy)-1-nitrobenzene (Method 10) (1.0 g, 4.2 mmol) and 10% palladium on charcoal catalyst (200 mg) in ethanol (30 ml) was stirred under an atmosphere of hydrogen for 3 hours. The catalyst was removed by filtration through diatomaceous earth and the filter pad was washed with methanol. The volatiles were removed from the filtrate by evaporation to give the title compound (400 mg, 46%) as an oil. M/z: 209 [MH]$^+$.

Method 10

4-(2-Diethylaminoethoxy)-1-nitrobenzene

Water (8 ml) and xylene (35 ml) were added to a mixture of sodium 4-nitrophenoxide (10.5 g, 65 mmol), 2-diethylamino)ethylchloride hydrochloride (8.6 g, 50 mmol) and potassium carbonate (10.4 g, 75 mmol) and the resulting mixture was heated at reflux for 2 hours. A Dean-Stark apparatus was then fitted and the water was removed. The organic solution was allowed to cool to ambient temperature and left to stand for 18 hours. The solution was decanted from the precipitated solid and the volatiles were removed from the decanted solution by evaporation to give the title compound (8.0 g, 52%) as an oil. NMR: 0.90 (t, 6H), 2.50 (q, 2H), 2.89 (t, 2H), 4.15 (t, 2H), 7.15 (d, 2H), 8.18 (d, 2H); m/z: 239 [MH]$^+$.

Method 11

4-[3-(N,N-Dimethyl)amino-2-hydroxypropoxy]aniline

3-N,N-Dimethylamino-2-hydroxy-3-(4-nitrophenoxy) propane (Method 12) (3.75 g) was dissolved in ethanol (40 ml). Under an atmosphere of nitrogen, 10% palladium-on-carbon (0.4 g) was added. The nitrogen atmosphere was replaced by one of hydrogen and the reaction mixture was stirred overnight. The catalyst was removed by filtration through diatomaceous earth and the filtrate was evaporated to dryness. The residue was dissolved in diethyl ether containing a small amount of isopropanol and hydrogen chloride solution (1M in ether, 16 ml) was added. The ether was evaporated and the solid residue was suspended in isopropanol. This mixture was heated on a steam bath for several minutes then allowed to cool to ambient temperature. The resulting powder was collected by filtration, washed with isopropanol, ether and dried (3.04 g 72.4%). NMR: 2.80 (s, 6H), 3.15 (m, 2H), 3.88 (m, 2H), 4.25 (m, 1H), 5.93 (br s, 1H), 6.88 (m, 4H); m/z 211 [MH]$^+$; EA $C_{11}H_{18}N_2O_2$.1.6 HCl requires C; 49.2, H; 7.4, N; 10.4, Cl; 21.7%: found: C; 49.2, H; 7.2, N; 10.1; Cl; 19.1%.

Method 12

3-N,N-Dimethylamino-2-hydroxy-1-(4-nitrophenoxy) propane 1-(4-Nitrophenoxy)-2,3-epoxypropane (Method 13) (4.3 g) was dissolved in methanol (30 ml) and DMF (10 ml). Dimethylamine (2M solution in methanol, 17 ml) was added and the mixture was stirred at ambient temperature overnight. The reaction mixture was evaporated to dryness and the residue was dissolved in saturated sodium bicarbonate solution and ethyl acetate. The ethyl acetate layer was separated and washed twice with saturated brine, dried over anhydrous sodium sulphate, filtered and evaporated to yield an oil that slowly crystallised under high vacuum (4.79 g, 89.9%). NMR (CDCl$_3$): 2.33 (s, 6H), 2.98 (m, 1H), 2.54 (m, 1H), 4.00 (m, 3H), 7.00 (d, 2H), 8.20 (d, 2H); m/z 241 [MH]$^+$.

Method 13

1-(4-Nitrophenoxy)2,3-epoxypropane 1-(4-Nitrophenoxy)-2,3-epoxypropane was prepared by an analogous method to that described by Zhen-Zhong Lui et. al. in Synthetic Communications (1994), 24, 833–838.

4-Nitrophenol (4.0 g), anhydrous potassium carbonate (8.0 g) and tetrabutylammonium bromide (0.4 g) were mixed with epibromohydrin (10 ml). The reaction mixture was heated at 100° C. for 1 hour. After cooling to ambient temperature, the reaction mixture was diluted with ethyl acetate and filtered. The filtrate was evaporated to dryness and the residue was co-distilled twice with toluene. The resulting oil was purified by column chromatography and eluted with ethanol (1.0%):dichloromethane to yield on evaporation an oil that crystallised (4.36 g, 77.7%). NMR (CDCl$_3$): 2.78 (m, 1H), 2.95 (m, 1H), 3.38 (m, 1H), 4.02 (dd, 1H), 4.38 (dd, 1H), 7.00 (d, 2H), 8.20 (d, 2H); m/z 196 [MH]$^+$.

Method 14
2-Methylthio-4-(2,5-dimethylimidazo[1,2a]pyrid-3-yl)pyrimidine

A mixture of 3-(3-dimethylaminoprop-2-en-1-oyl)-2,5-dimethylimidazo[1,2a]pyridine (Method 15) (3.50 g, 14.4 mmol), thiourea (1.09 g, 14.4 mmol) and sodium methoxide (1.01 g, 18.7 mmol) were heated at 85° C. in 1-butanol (50 ml) for 2 hours. The mixture was allowed to cool to 30° C. and methyl iodide (11.8 ml, 28.8 mmol) was added dropwise and the mixture stirred for a further 3 hours. The volatiles were removed by evaporation and the residue purified by chromatography eluting with ethyl acetate/methanol (100:0 increasing in polarity to 97:3) to give the title compound (2.37 g, 61%). NMR: 2.41 (s, 3H), 2.60 (s, 3H), 2.70 (s, 3H), 7.56 (d, 1H), 7.88 (d, 1H), 7.92 (d, 1H), 8.81 (d, 1H), 9.39 (s, 1H); m/z: 271 [MH]$^+$.

Method 15
3-(3-Dimethylaminoprop-2-en-1-oyl)-2,5-dimethylimidazo[1,2a]pyridine

A solution of 3-acetyl-2,5-dimethylimidazo[1,2a]pyridine (Method 16) (3.60 g, 19.1 mmol) in DMFDMA (20 ml) was heated at reflux for 60 hours. The mixture was allowed to cool and the solvent was removed by evaporation. The residue was triturated with hot ether, the solid collected by filtration and dried to give the title compound (3.61 g, 84%). NMR: 2.30 (s, 3H), 2.62 (s, 3H), 2.90 (r s, 3H), 3.10 (br s, 3H), 5.48 (d, 1H), 7.22 (dd, 1H), 7.44 (d, 1H), 7.68 (d, 1H), 9.39 (dd, 1H).

Method 16
3-Acetyl-2,5-dimethylimidazo[1,2a]pyridine

3-Chloro-2,4-pentaneodione (6.5 ml 54.4 mmol) was added to a suspension of 2-amino-4-methylpyridine (5.00 g, 46.3 mmol) and sodium iodide (10 mg) in THF (60 ml) and the mixture was heated at reflux for 16 hours. The reaction mixture was allowed to cool and the solvent was removed by evaporation. The resulting solid residue was triturated with hot hexane, collected by filtration and dried to give the title compound (3.69 g, 436). NMR: 2.35 (s, 3H), 2.75 (s, 3H), 7.41 (dd, 1H), 7.57 (d, 1H), 9.40 (d, 1H); m/z: 189 [MH]$^+$.

Method 17
4-(2-Methylpyrazolo[2,3a]pyrid-3-yl)-2-methylthiopyrimidine

A mixture of 3-(3-dimethylaminoprop-2-en-1-oyl)-2-methyl-pyrazolo[2,3a]pyridine (Method 18) (3.89 g, 17 mmol), thiourea (1.27 g, 17 mmol) and sodium methoxide (0.929 g, 17 mmol) in butanol (45 ml) was heated at 85° C. for two hours under nitrogen. Methyl iodide (1.05 ml, 17 mmol) was added and the mixture heated at 85° C. for a further 2 hours. The volatiles were removed by evaporation and the residue was purified by chromatography eluting with ethyl acetate/methanol (100:0 increasing in polarity to 97:3) to give the title compound (3.1 g, 68%). NMR: 2.58 (s, 1H), 2.68 (s, 3H), 7.04 (dd, 1H), 7.39 (dd, 1H), 7.48 (d, 1H), 8.35 (d, 1H), 8.50 (d, 1H), 8.72 (d, 1H); m/z: 257 [MH]$^+$.

Method 18
3-(3-Dimethylaminoprop-2-en-1-oyl)-2-methylpyrazolo[2,3a]pyridine

A mixture of 3-acetyl-2-methylpyrazolo[2,3a]pyridine (Method 19) (2 g, 11.5 mmol) and DMFDMA (10 ml) was heated 110° C. under nitrogen for 48 hours. The volatiles were removed by evaporation, the residue was triturated with hot ether and the solid product collected by filtration to give the title compound (1.98 g, 75%). NMR: 2.60 (s, 3H), 3.30 (s, 6H), 5.49 (d, 1H), 6.95 (dd, 1H), 7.38 (dd, 1H), 7.62 (d, 1H), 8.10 (d, 1H), 8.62 (d, 1H); m/z: 230 [MH]$^+$.

Method 19
3-Acetyl-2-methylpyrazolo[2,3a]pyridine

Potassium carbonate (53.8 g, 0.39 mol) and then 2,4-pentanedione (24.8 g, 025 mol) were added to a solution of 1-aminopyridinium iodide (26.9 g, 0.12 mol) in water (336 ml) and the mixture was heated at 80° C. for 2 hours, allowed to cool to ambient temperature and left to stand for 18 hours. Water was added and the mixture was extracted to with ethyl acetate. The combined extracts were dried and the volatiles were removed by evaporation. The residue was recrystallized from hot hexane and the product collected by filtration. Solvent was removed from the filtrate by evaporation and was added to the insoluble residue from the recrystallization. This crude mixture was purified by chromatography eluting with dichloromethane/hexane (1:1) increasing in polarity to dichloromethane/methanol (97:3). This product was triturated with hexane and added to the product obtained from the initial recrystallization to give the title compound (9.6 g, 33%). NMR: 2.50 (s, 3H), 2.62 (s, 3H), 7.09 (dd, 1H), 7.55 (dd, 1H), 8.12 (d, 1H), 8.72 (d, 1H); m/z: 175 [MH]$^+$.

Method 20
2-Chloro-4-(imidazo[1,2a]pyrid-3-yl)pyrimidine

A suspension of 2-hydroxy-4-(imidazo[1,2a]pyrid-3-yl)pyrimidine (Method 21; 9.92 g, 46%) in phosphoryl chloride (200 ml) and phosphorus pentachloride (11 g, 53%) was heated at reflux under nitrogen for 24 hours. Excess phosphoryl chloride was removed by evaporation, ice water was added and the mixture neutralised with 2M aqueous sodium hydroxide solution. The aqueous mixture was extracted with ethyl acetate, dried and evaporated to give the title compound 7.42 g (69%). NMR: 7.15 (dd, 1H), 7.59 (dd, 1H), 7.80 (d, 1H), 8.05 (d, 1H), 8.64 (d, 1H), 8.79 (s, 1H), 9.72 (d, 1H); m/z: 231 [MH]$^+$.

Method 21
2-Hydroxy-4-(imidazo[1,2a]pyrid-3-yl)pyrimidine

A solution of sodium nitrate (11.04 g, 0.16 mol) in water (100 ml) was added to a solution of 2-amino-4-(imidazo[1,2a]pyrid-3-yl)pyrimidine (Method 22; 11.27 g, 0.053 mol) in 70% acetic acid (330 ml) at 60° C. The mixture was heated at 60° C. for 3 hours, allowed to cool and neutralised with 5M aqueous sodium hydroxide solution, the resulting precipitate was collected by filtration, washed quickly with cold water and dried in vacuum oven at 50° C. to give the title compound 9.95 g (89%). NMR: 6.98 (d, 1H), 7.12 (dd, 1H), 7.55 (dd, 1H), 7.80 (d, 1H), 7.82 (d, 1H), 8.70 (s, 1H); m/z: 213 [MH]$^+$.

Method 22
2-Amino-4-(imidazo[1,2a]pyrid-3-yl)pyrimidine

A mixture of 3-(3-dimethylaminoprop-2-en-1-oyl)imidazo[1,2a]pyridine (Method 5; 20 g, 0.093 mol), sodium methoxide (20.1 g, 0.372 mol) and guanidine hydrochloride (22.09 g, 0.233 mol) in n-butanol (1500 ml) and methanol (1000 ml) were heated at reflux for 60 hours. The resulting solution was decanted from insoluble material, the volatiles were removed by evaporation and the residue was purified by chromatography eluting with dichloromethane/methanol (97:3) to give the title compound 13 g (67%). NMR: 6.78 (s, 1H), 7.15–7.05 (m, 2H), 7.45 (dd, 2H), 7.70 (d, 1H), 8.20 (d, 1H), 8.50 (s, 1H), 10.15 (d, 1H); m/z: 212 [MH]$^+$.

Method 23
4-(N-Methylsulphamoyl)aniline

Methylamine (3 ml of a 33% solution in ethanol) and then triethylamine (0.159 ml, 1.1 mmol) was added to sulphanilyl fluoride (200 mg, 1.1 mmol), and the mixture heated at 80° C. for 6 hours then at ambient temperature for 18 hours. The volatiles were removed by evaporation and the residue azeotroped with toluene to give the title compound (160 mg, 76%). NMR: 2.30 (s, 3H), 5.85 (s, 2H), 6.60 (d, 2H), 7.39 (d, 2H); m/z: 187 [MH]$^+$.

Method 24
4-[N-(2-Methoxyethyl)sulphamoyl]aniline

A mixture of 2-methoxyethylamine (859 mg, 11.4 mmol), sulphanilyl fluoride (1.0 g, 5.71 mmol), and triethylamine (1.72 g, 22.9 mmol) in n-butanol (15 ml) was heated at reflux for 18 hours. The mixture was allowed to cool and the volatiles were removed by evaporation. The residue was purified by chromatography eluting with ethyl acetate/hexane (50:50) increasing in polarity to (70:30) to give the title compound (860 mg, 65%). NMR: 2.78 (q, 2H), 3.15 (s, 3H), 3.25 (t, 2H), 5.87 (s, 2H), 6.58 (d, 2H), 7.10 (t, 1H), 7.40 (d, 2H); m/z: 231 [MH]$^+$.

Method 25–26

The following compounds were prepared using the procedure of Method 24.

| Meth | Compound Name | NMR | m/z |
|---|---|---|---|
| 25 | 4-(N-Propyl-sylphamoyl)-aniline | 0.78(t, 3H), 1.40–1.25(m, 2H), 2.60(q, 2H), 5.84(s, 2H), 6.59(d, 2H), 7.00(t, 1H), 7.39(d, 2H) | |
| 26 | 4-(N-Cyclo-propyl-sylphamoyl) aniline | 0.01–0.15(m, 4H), 1.70–1.75(m, 1H), 5.60(s, 2H), 6.30(d, 2H), 7.05(s, 1H), 7.10(d, 2H) | 211 [M–H]$^-$ |

Method 27
1-[3-(4-Bromobenzoylamino)propyl]imidazole 1-(3-Aminopropyl)imidazole (2.39 ml, 0.02 mol) was added to a solution of 4-bromobenzoyl chloride (4.0 g, 0.218 mol) in ethanol (250 ml). The mixture was stirred at ambient temperature for 18 hours. The volatiles were removed by evaporation and the residue was purified by chromatography eluting with hexane/dichloromethane (50:50) increasing in polarity to dichloromethane/methanol (80:20) to give the title compound. NMR: 1.95 (m, 2H), 3.20 (q, 2H), 4.0 (t, 2H), 6.87 (s, 1H), 7.19 (s, 1H), 7.64 (d, 2H), 7.68 (s, 1H), 7.78 (d, 2H), 8.58 (t, 1H); m/z: 308 [MH]$^+$.

Method 28
1-[3-(4-Bromobenzoylamino)propyl]-2-oxopyrolidine 1-(3-Aminopropyl)-2-oxopyrolidine (3.07 ml 14 mmol) was treated as described in Method 27 to give the title compound. NR: 1.68 (quin, 2H, 1.90 (quin, 2H), 2.0 (t, 2H), 3.15–3.22 (m, 4H), 3.29–3.33 (m, 2H), 7.64 (d, 2H), 7.78 (d, 2H), 8.48 (t, 1H).

Method 29
2,4-Dichloro-1-(2-methoxyethylsulphamoyl)benzene 2,4-Dichlorobenzenesulphonyl chloride (500 mg 2.1 mmol) and 2-methoxyethylamine (230 mg, 3.1 mmol) in n-butanol (10 ml) was heated at reflux for one hour. The volatiles were removed by evaporation and residue purified by chromatography eluting with hexane/ethyl acetate (50:50) to give the title compound. NMR: 3.04 (q, 21), 3.08 (s, 3H), 3.22 (t, 2H), 7.60 (dd, 31), 7.82 (d, 1H), 7.92 (d, 1H), 8.0 (s, 2H); m/z: 282 [M–H]$^-$.

Method 30
2,4-Dichloro-1-(1-propylsulphamoyl)benzene 2,4-Dichlorobenzenesulphonyl chloride (500 mg 2.1 mmol) and 1-propylamine (0.2 ml, 2.4 mmol) in n-butanol (10 ml) was heated at reflux for 48 hour. The volatiles were removed by evaporation and the residue triturated with ether and the product collected by filtration to give the title compound. NMR: 0.78 (t, 3H), 1.35 (q, 2H), 2.79 (t, 2H), 7.60 (dd, 1H), 7.84 (d, 1H), 7.92 (d, 2H)

Method 31
2-Amino-5-bromo-4-(imidazo[1,2a]pyrid-3-yl)pyrimidine

Bromine (54 ml, 0.001 mmol) was added dropwise to a solution of 2-amino-4-(imidazo[1,2a]pyrid-3-yl)pyrimidine (Method 22; 200 mg, 0.95 mmol) in acetic acid (4 ml) at ambient temperature. The mixture was heated at 65° C. for 90 minutes and allowed to cool. The resulting precipitate was collected by filtration, washed with hexane and dried to give the title compound. NMR: 7.44 (dd, 1H), 7.90–8.00 (m, 2H), 8.59 (s, 1H), 8.99 (s, 1H), 9.78 (d, 1H); m/z: 290 [MH]$^+$.

Method 32
5-Bromoimidazo[1,2a]pyridine

A solution of bromoacetaldehyde diethylacetyl (50 ml, 0.332 mol) in dioxane (143 ml), water (85 ml) and conc. hydrochloric acid (5 ml) was heated at reflux for 30 minutes and the mixture allowed to cool. Sodium hydrogen carbonate (53 g) was added followed by a solution of 5-bromo-2-aminopyridine (30 g, 0.174 mol) in dioxane (230 ml) and water (85 ml) and the mixture was heated at reflux for 24 hours. The mixture was allowed to cool, poured into water and acidified with 2M hydrochloric acid. The mixture was washed with ethyl acetate and the aqueous layer was basified with 2M aqueous sodium hydroxide solution. The aqueous mixture was extracted with ethyl acetate. The extracts were combined, dried and the volatiles removed by evaporation. The residue was purified by chromatography eluting with hexane/ethyl acetate (50:50) in creasing in polarity to (25:50) to give the title compound 20 g (59%). NMR: 7.30 (dd, 1H), 7.54 (d, 1H), 7.59 (s, 1H), 7.90 (s, 1H), 8.89 (s, 1H); m/z: 197 [MH]$^+$.

Method 33
3-Acetyl-5-bromoimidazo[1,2a]pyridine

Aluminium chloride (10.2 g, 77 mmol) was added in portions over 10 minutes to a solution of 5-bromoimidazo[1,2a]pyridine (Method 32; 5.0 g, 26 mmol) in dichloromethane (100 ml) cooled to 0° C. The mixture was heated to reflux and acetyl chloride (2.54 ml, 36 mmol) was added over 15 minutes. The mixture was heated at reflux for 24 hours, cooled to 0° C., and further aluminum chloride (10.2 g, 77 mmol) followed by acetyl chloride (3.26 ml) were added. The mixture heated at reflux for 24 hours and then the volatiles were removed by evaporation. Iced water was added, the mixture was basified with 2M aqueous sodium hydroxide solution and extracted with ethyl acetate. The extracts were washed with water, dried and the solvent evaporated to the title compound which was used without further purification 4.0 g. NMR: 2.58 (s, 3H), 7.74–7.82 (m, 2H), 8.62 (s, 1H), 9.62 (s, 1H); m/z: 241 [MH]$^+$.

Method 34
5-Bromo-3-(3-dimethylaminoprop-2-en-1-oyl)imidazo[1,2a]pyridine

3-Acetyl-5-bromoimidazo[1,2a]pyridine (Method 33; 4.0 g) was dissolved in DMFDMA (200 ml) and the mixture was heated at reflux under nitrogen for 72 hours. The excess DMFDMA was removed by evaporation and the residue triturated with hot ether, collected by filtration and washed with ether to give the title compound 2.6 g (53%). NMR: 2.90 (s, 3H), 3.12 (s, 1H), 5.82 (d, 1H), 7.58 (dd, 1H), 7.64 (d, 1H), 7.70 (s, 1H), 8.44 (s, 1H), 9.90 (s, 1H); m/z: 294 [MH]$^+$.

Method 35
2-Amino-4-(5-bromoimidazo[1,2a]pyrid-3-yl)pyrimidine

A mixture of 5-bromo-3-(3-dimethylaminoprop-2-en-1-oyl)imidazo[1,2a]pyridine (Method 34; 2.5 g, 8.5 mmol) guanidine hydrochloride (2.01 g, 21 mmol) and sodium methoxide (1.83 g, 34 mmol) in n-butanol (140 ml) and methanol (45 ml) was heated at reflux for 18 hours. The volatiles were removed by evaporation and the residue purified by chromatography eluting with dichloromethane/methanol (95:5) to give the title compound 1.1 g (45%). NMR: 6.86 (s, 2H), 7.12 (d, 1H), 7.57 (dd, 1H), 7.68 (d, 1H), 8.22 (d, 1H), 8.51 (s, 1H); m/z: 290 [MH]$^+$.

Method 36
6-Phenylimidazo[1,2a]pyridine

2-Amino-4-phenylpyridine (0.90 g, 5.29 mmol) was treated as described in Method 32 to give the title compound. NMR: 7.07 (d, 1H), 7.35–7.53 (m, 4H), 7.59 (s, 1H), 7.64 (d, 2H), 7.83 (s, 1H), 8.18 (d, 1H); m/z: 195 [MH]$^+$.

Method 37
3-Bromo-6-phenylimidazo[1,2a]pyridine

A solution of bromine (0.24 ml, 4.6 mmol) in water (10 ml) was added to a solution of 6-phenylimidazo[1,2a]pyridine (Method 36; 0.85 g, 4.88 mmol) in ethanol (15 ml) and the mixture stirred for 14 hours in the dark. The mixture was basified with aqueous sodium hydrogen carbonate solution and extracted with dichloromethane. The extracts were dried, the solvent removed by evaporation and the residue triturated with ether an collected by filtration to give the title compound. NMR: 7.38–7.56 (m, 4H), 7.77 (s, 1H), 7.83 (d, 2H), 7.96 (s, 1H), 8.39 (d, 1H); m/z: 273 [MH]$^+$.

Method 38
3-(3-Dimethylaminoprop-2-en-1-oyl)-6-phenylimidazo[1,2a]pyridine

Phenylmagnesium bromide (2.7 ml of a 1M solution in THF) was added to a solution of 3-bromo-6-phenylimidazo[1,2a]pyridine (Method 37; 0.48 g, 1.76 mmol) in THF under nitrogen and the mixture was heated at reflux for 2 hours. The mixture was cooled to 0° C. and N-methoxy-N-methylacetamide (0.3 ml 2.64 mmol) was added dropwise. The mixture was allowed to warm to ambient temperature and stirred for 18 hours. The reaction mixture was diluted with ether washed with aqueous sodium hydrogen carbonate solution, then brine dried and the volatiles removed by evaporation. The residue was dissolved in DMFDMA (10 ml) and the mixture heated at reflux under nitrogen for 60 hours. The excess DMFDMA was removed by evaporation and the residue triturated with hot ether, collected by filtration and washed with ether to give the title compound 170 mg (33%). NMR: 2.8–3.2 (br d, 6H), 5.85 (d, 1H), 7.38–7.58 (m, 4H), 7.67 (d, 1H), 7.86 (d, 2H), 8.00 (s, 1H), 8.48 (s, 1H), 9.76 (d, 1H); m/z: 292 [MH]$^+$.

Method 39
3-(3-Dimethylaminoprop-2-en-1-oyl)-2-methyl-6-methoxyimidazo[1,2a]pyridine 3-Acetyl-6-methoxy-2-methylimidazo[1,2a]pyridine (Method 40; 1.49 g, 7.3 mmol) and toluenesulphonic acid (5 mg) in DMFDMA (25 ml) was heated at reflux for 20 hours. The excess DMFDMA was removed by evaporation. The residue was triturated with ether and the product collected by filtration to give the title compound. NMR: 2.69 (s, 3H), 3.28 (s, 6H), 3.82 (s, 3H), 5.44 (d, 1H), 6.69 (dd, 1H), 6.97 (d, 1H), 7.65 (d, 1H), 9.21 (d, 1H); m/z: 260 [MH]$^+$.

Method 40
3-Acetyl-6-methoxy-2-methylimidazo[1,2a]pyridine

A solution of 3-chloroacetoacetone (2.86 ml) in THF (6 ml) was added to a solution of 2-amino-4-methoxypyridine (2.71 g, 21.8 mmol) in THF (14 ml) and the mixture was stirred at ambient temperature for 30 minutes and then heated at reflux for 3 hours. The solvent was removed by evaporation and the residue purified by chromatography eluting with dichloromethane/methanol (100:0) increasing in polarity to (97:3). The product was recrystallized from tert-butylmethyl ether to give the title compound (2.1 g, 47%). NMR: 2.05 (s, 3H), 2.63 (s, 3H), 3.86 (s, 3H), 6.83 (dd, 1H), 7.07 (d, 1H), 9.20 (d, 1H); m/z: 205 [MH]$^+$.

Method 41
4-Sulphamoylphenylguanidine

A mixture of sulphanilamide (20 g, 0.166 mol), benzoyl cyanamide (34 g, 0.33 mmol) in ethanol (60 ml) and concentrated hydrochloric acid (11 ml) was heated on a steam bath until the solvent had evaporated. Water was added and the mixture heated at reflux for 5 minutes. Sodium hydroxide (14.4 g) was added and the mixture heated at reflux. The mixture was allowed to cool and was adjusted to pH2 with hydrochloric acid and the precipitated solid removed by filtration. The filtrate was neutralised and the solvent removed by evaporation. The residue was recrystallized from water to give crude title product. m/z: 215 [MH]$^+$.

Method 42
4-(2-Diethylaminoethoxy)phenylguanidine

A mixture of 3,5-dimethylpyrazolylformidinium nitrate (0.20 g, 1 mmol), 4-(2-diethylaminoethoxy)aniline (Method 9; 1.0 g, 4.8 mmol) in water (1 ml) was heated at reflux for 3 hours. The solvent was removed by evaporation, the residue triturated with hot ether and the product collected by filtration to give crude title compound. NMR: 0.98 (t, 6H), 2.57 (q, 4H), 2.79 (t, 2H), 4.00 (t, 2H), 6.99 (d, 2H), 7.15 (d, 2H); m/z: 251 [MH]$^+$.

Example 99

The following illustrate representative pharmaceutical dosage forms containing the compound of formula (I), or a pharmaceutically acceptable salt or in vivo hydrolysable ester thereof (hereafter compound X), for therapeutic or prophylactic use in humans:

| (a): Tablet I | mg/tablet |
| --- | --- |
| Compound X | 100 |
| Lactose Ph. Eur | 182.75 |
| Croscarmellose sodium | 12.0 |
| Maize starch paste (5% w/v paste) | 2.25 |
| Magnesium stearate | 3.0 |

| (b): Tablet II | mg/tablet |
| --- | --- |
| Compound X | 50 |
| Lactose Ph. Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| (c): Tablet III | mg/tablet |
| --- | --- |
| Compound X | 1.0 |
| Lactose Ph. Eur | 93.25 |
| Croscarmellose sodium | 4.0 |
| Maize starch paste (5% w/v paste) | 0.75 |
| Magnesium stearate | 1.0 |

| (d): Capsule | mg/capsule |
| --- | --- |
| Compound X | 10 |
| Lactose Ph. Eur | 488.5 |
| Magnesium stearate | 1.5 |

| (e): Injection | (50 mg/ml) |
| --- | --- |
| Compound X | 5.0% w/v |
| 1M Sodium hydroxide solution | 15.0% v/v |

-continued

| | |
|---|---|
| 0.1M Hydrochloric acid | (to adjust pH to 7.6) |
| Polyethylene glycol 400 | 4.5% w/v |
| Water for injection | to 100% |

| (f): Injection II | 10 mg/ml |
|---|---|
| Compound X | 1.0% w/v |
| Sodium phosphate BP | 3.6% w/v |
| 0.1M Sodium hydroxide solution | 15.0% v/v |
| Water for injection | to 100% |

| (g): Injection III | (1 mg/ml, buffered to pH6) |
|---|---|
| Compound X | 0.1% w/v |
| Sodium phosphate BP | 2.26% w/v |
| Citric acid | 0.38% w/v |
| Polyethylene glycol 400 | 3.5% w/v |
| Water for injection | to 100% |

Note
The above formulations may be obtained by conventional procedures well known in the pharmaceutical art. The tablets (a)–(c) may be enteric coated by conventional means, for example to provide a coating of cellulose acetate phthalate.

What is claimed is:

1. A compound of formula (I):

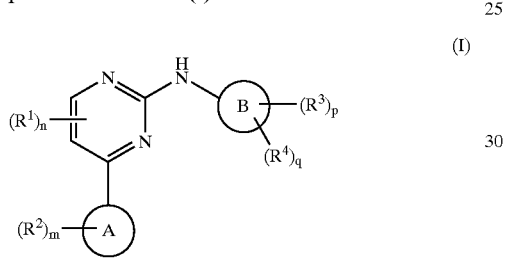

(I)

wherein:

Ring A is imidazo[1,2a]pyrid-3-yl or pyrazolo[2,3a]pyrid-3-yl;

$R^2$ is attached to a ring carbon and is selected from halo, nitro, cyano, hydroxy, trifluoromethyl, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, C, alkanoyloxy, N-($C_{1-6}$alkyl)amino, N,N-($C_{1-6}$alkyl)$_2$amino, $C_{1-6}$alkanoylamino, N-($C_{1-6}$alkyl)carbamoyl, N,N-($C_{1-6}$alkyl)$_2$carbamoyl, $C_{1-6}$alkylS(O)$_a$ wherein a is 0 to 2, $C_{1-6}$alkoxycarbonyl, N-($C_{1-6}$alkyl)sulphamoyl, N,N-($C_{1-6}$alkyl)$_2$sulphamoyl, phenyl, heterocyclic group, phenylthio or (heterocyclic group)thio; wherein any $C_{1-6}$alkyl, $C_{2-6}$alkenyl, $C_{2-6}$alkynyl, phenyl or heterocyclic group may be optionally substituted on carbon by one or more G; and wherein if said heterocyclic group contains an —NH— moiety that nitrogen may be optionally substituted by a group selected from Q;

m is 0–5; wherein the values of $R^2$ may be the same or different;

$R^1$ is halo, nitro, cyano, hydroxy, trifluoromethyl, trifluoromethoxy, amino, carboxy, carbamoyl, mercapto, sulphamoyl, $C_{1-3}$alkyl, $C_{2-3}$alkenyl, $C_{2-3}$alkynyl, $C_{1-3}$alkoxy, $C_{1-3}$alkanoyl, N-($C_{1-3}$alkyl)amino, N,N-($C_{1-2}$alkyl)$_2$amino, $C_{1-3}$alkanoylamino, N-($C_{1-3}$alkyl)carbamoyl, N,N-($C_{1-2}$alkyl)$_2$carbamoyl, $C_{1-3}$alkylS(O)$_a$ wherein a is 0 to 2, N-($C_{1-3}$alkyl)sulphamoyl or N,N-($C_{1-3}$alkyl)$_2$sulphamoyl; wherein any $C_{1-2}$alkyl, $C_{1-3}$alkyl, $C_{2-3}$alkenyl or $C_{2-3}$alkynyl may be optionally substituted on carbon by one or more J;

n is 0 to 2, wherein the values of $R^1$ may be the same or different;

Ring B is phenyl or phenyl fused to a $C_{5-7}$cycloalkyl ring;

$R^3$ is halo, nitro, cyano, hydroxy, amino, carboxy, carbamoyl, mercapto, sulphamoyl, $C_{2-6}$alkenyl or $C_{2-6}$alkynyl;

p is 0–4; wherein the values of $R^3$ may be the same or different;

$R^4$ is a group A—E—; wherein
A is selected from $C_{1-6}$alkyl, phenyl, a heterocyclic group, $C_{1-3}$cycloalkyl, phenyl$C_{1-6}$alkyl, (heterocyclic group)$C_{1-6}$alkyl or $C_{3-8}$cycloalkyl$C_{1-6}$cycloalkyl; which $C_{1-6}$alkyl, phenyl, a heterocyclic group, $C_{3-8}$cycloalkyl, phenyl$C_{1-6}$alkyl, (heterocyclic group)$C_{1-6}$alkyl or $C_{3-8}$cycloalkyl$C_{1-6}$cycloalkyl may be optionally substituted on carbon by one or more D; and wherein if said heterocyclic group contains an —NH— moiety that nitrogen may be optionally substituted by a group selected from R;
E is a direct bond or —O—, —C(O)—, —OC(O)—, —C(O)O—, —N($R^a$)C(O)—, —C(O)N($R^a$), —N($R^a$)—, —S(O)$_r$—, —SO$_2$N($R^a$)— or —N($R^a$)SO$_2$—; wherein $R^a$ is hydrogen or $C_{1-6}$alkyl optionally substituted by one or more D and r is 0–2;
D is independently selected from oxo, halo, nitro, cyano, hydroxy, trifluoromethyl, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N-($C_{1-6}$alkyl)amino, N,N-($C_{1-6}$alkyl)$_2$amino, $C_{1-6}$alkanoylamino, N-($C_{1-6}$alkyl)carbamoyl, N,N-($C_{1-6}$alkyl)$_2$carbamoyl, $C_{1-6}$alkylS(O)$_a$ wherein a is 0 to 2, $C_{1-6}$alkoxycarbonyl, $C_{1-6}$alkoxycarbonylamino, benzyloxycarbonylamino, N-($C_{1-6}$alkyl)sulphamoyl and N,N-($C_{1-6}$alkyl)$_2$sulphamoyl; wherein any $C_{1-6}$alkyl, $C_{2-6}$alkenyl, $C_{2-6}$alkynyl or phenyl may be optionally substituted on carbon by one or more K;

q is 0–2; wherein the values of $R^4$ may be the same or different; and wherein p+q≦5;
G, J and K are independently selected from halo, nitro, cyano, hydroxy, trifluoromethoxy, trifluoromethyl, amino, carboxy, carbamoyl, mercapto, sulphamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl or N-methyl-N-ethylsulphamoyl; and
Q and R are independently selected from $C_{1-4}$alkyl, $C_{1-4}$alkanoyl, $C_{1-4}$alkylsulphonyl, $C_{1-4}$alkoxycarbonyl, carbamoyl, N-($C_{1-4}$alkyl)carbamoyl, N,N-($C_{1-4}$alkyl)carbamoyl, benzyl, benzyloxycarbonyl, benzoyl and phenylsulphonyl;
or a pharmaceutically acceptable salt or an in vivo hydrolysable ester formed from an available carboxy or hydroxy group thereof.

2. A compound of formula (I) according to claim 1 wherein $R^1$ is bromo or 2-hydroxyethylthio and n is 0–1; or a pharmaceutically acceptable salt or an in vivo hydrolysable formed from an available carboxy or hydroxy group ester thereof.

3. A compound of formula (I) according to claim 1 wherein Ring A is imidazo[1,2a]pyrid-3-yl; or a pharmaceutically acceptable salt or an in vivo hydrolysable ester formed from an available carboxy or hydroxy group thereof.

4. A compound of formula (I) according to claim 1 wherein $R^2$ is attached to a ring carbon and is selected from fluoro, chloro, bromo, cyano, methyl, methoxy, ethylthio, 2-hydroxyethylthio or 2-dimethylaminoethylthio and m is 0–2; wherein the values of $R^2$ may be the same or different; or a pharmaceutically acceptable salt or an in vivo hydrolysable ester formed from an available carboxy or hydroxy group thereof.

5. A compound of formula (I) according to claim 1 wherein $R^3$ is fluoro, chloro, bromo or sulphamoyl; and p is 1; or a pharmaceutically acceptable salt or an in vivo hydrolysable ester formed from an available carboxy or hydroxy group thereof.

6. A compound of formula (I) according to claim 1 wherein $R^4$ is methyl, ethyl, methoxy, methylthio, acetyl, benzyloxy, mesyl, N,N-diethylaminoethoxy, 3-N,N-dimethylamino-2-hydroxypropoxy, phenoxy, N-methylcarbamoyl, N,N-dimethylcarbamoyl, N-(3-imidazol-1-ylpropyl)carbamoyl, N-[3-(2-oxo-pyrrolidin-1-yl)propyl]carbamoyl, 3,5-dioxapiperidin-1-ylsulphonyl, N-cyclopropylsulphamoyl, N-cyclopropylmethylsulphamoyl, anilinosulphonyl, N-pyrimidin-2-ylsulphamoyl, N-methylsulphamoyl, N-propylsulphamoyl, N-(2-methoxyethyl)sulphamoyl, N-(2-methylaminoethyl)sulphamoyl, N-(2-isopropylaminoethyl)sulphamoyl, N-(2-dimethylaminoethyl)sulphamoyl, N-(2-diethylaminoethyl)sulphamoyl, N-[2-(hydroxyethylamino)ethyl]sulphamoyl, N-[2-(diethylaminoethyl)ethyl]sulphamoyl, N-(pyrrolidin-1-ylethyl)sulphamoyl, N-[2-(1-methylpyrrolidin-2-yl)ethyl]sulphamoyl, N-(2-piperidin-1-ylethyl)sulphamoyl, N-(2-piperazin-1-ylethyl)sulphamoyl, N-(2-morpholinoethyl)sulphamoyl, N-(2-imidazol-4-ylethyl)sulphamoyl, N-(3-hydroxypropyl)sulphamoyl, N-(2,3-dihydroxypropyl)sulphamoyl, N-(3-methoxypropyl)sulphamoyl, N-(3-aminopropyl)sulphamoyl, N-(3-methylaminopropyl)sulphamoyl, N-(3-dimethylaminopropyl)sulphamoyl, N-(3-diethylaminopropyl)sulphamoyl, N-(3-isopropylaminopropyl)sulphamoyl, N-(3-t-butoxycarbonylaminopropyl)sulphamoyl, N-(3-benzyloxycarbonylaminopropyl)sulphamoyl, N-[3-(2-oxopyrrolidin-1-yl)propyl]sulphamoyl, N-(3-morpholinopropyl)sulphamoyl, N-[3-(4-methylpiperazin-1-yl)propyl]sulphamoyl, N-(3-imidazol-1-ylpropyl)sulphamoyl or N-(5-hydroxypentyl)sulphamoyl; and q is 1; or a pharmaceutically acceptable salt or an in vivo hydrolysable ester formed from an available carboxy or hydroxy group thereof.

7. A compound of formula (I) according to claim 1 wherein Ring B is phenyl; or a pharmaceutically acceptable salt or an in vivo hydrolysable ester formed from an available carboxy or hydroxy group thereof.

8. A compound of formula (I) selected from:
2-(4-Sulphamoylanilino)-4-(imidazo[1,2a]pyrid-3-yl) pyrimidine;
2-[4-(N-Methylsulphamoyl)anilino]-4-(imidazo[1,2a]pyrid-3-yl)pyrimidine;
2-{4-[N-(2-Methoxyethyl)sulphamoyl]anilino}-4-(imidazo[1,2a]pyrid-3-yl)pyrimidine;
2-{4-[N-(3-Methoxypropyl)sulphamoyl]anilino}-4-(imidazo[1,2a]pyrid-3-yl)pyrimidine;
2-{4-[N-(3-Isopropylaminopropyl)sulphamoyl]anilino}-4-(imidazo[1,2a]pyrid-3-yl) pyrimidine;
2-{4-[N-(3-Dimethylaminopropyl)sulphamoyl]anilino}-4-(imidazo[1,2a]pyrid-3-yl) pyrimidine;
2-{4-[N-(2-Dimethylaminoethyl)sulphamoyl]anilino}-4-(imidazo[1,2a]pyrid-3-yl)pyrimidine;
2-{4-[N-(2-Methylaminoethyl)sulphamoyl]anilino}-4-(imidazo[1,2a]pyrid-3-yl)pyrimidine; or
2-{4-[N-(2-Methoxyethyl)sulphamoyl]anilino}-4-[5-(2-hydroxyethylthio)imidazo[1,2a]pyrid-3-yl]pyrimidine;

or a pharmaceutically acceptable salt or an in vivo hydrolysable ester formed from an available carboxy or hydroxy group thereof.

9. A process for preparing a compound of formula (I) according to claim 1, or a pharmaceutically acceptable salt or an in vivo hydrolysable ester formed from an available carboxy or hydroxy group thereof, which process (wherein $R^1$, $R^2$, $R^3$, $R^4$, Ring A, Ring B, m, p, q and n are, unless otherwise specified, as defined in formula (I)) comprises of:

a) reaction of a pyrimidine of formula (II):

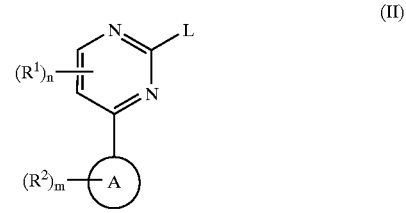

wherein L is a displaceable group; with an amine of formula (III):

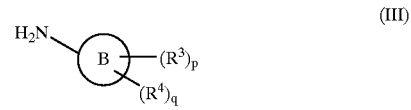

b) reacting a pyrimidine of formula (IV):

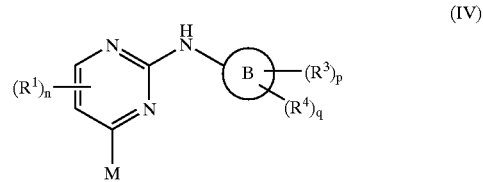

with a compound of the formula (V):

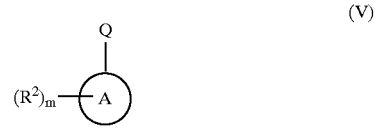

wherein one of M and Q is a displaceable group X and the other is an metallic reagent Y; or c) reacting a compounds of formula (VI):

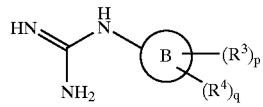

(VI)

with a compound of formula (VII):

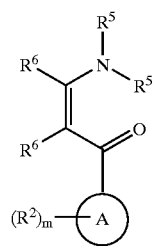

(VII)

wherein $R^5$ is $C_{1-6}$alkyl and $R^6$ is hydrogen or $R^1$;
and thereafter optionally:
i) converting a compound of the formula (I) into another compound of the formula (I);
ii) removing any protecting groups;
iii) forming a pharmaceutically acceptable salt or in vivo hydrolysable ester formed from an available carboxy or hydroxy group.

10. A pharmaceutical composition which comprises a compound of formula (I) according to any one of claims 1–8, or a pharmaceutically acceptable salt or in vivo hydrolysable ester thereof formed from an available carboxy or hydroxy group, in association with a pharmaceutically-acceptable diluent or carrier.

11. A method for treating cancer in a warm blooded animal in need thereof which comprises administering to said animal an effective amount of a compound of the formula (I) as claimed in any one of claims 1–8, or a pharmaceutically acceptable salt or in vivo hydrolysable ester formed from an available carboxy or hydroxy group thereof.

12. A method for inhibiting CDK2 in a warm blooded animal in need thereof which comprises administering to said animal an inhibiting amount of a compound of the formula (I) as claimed in any one of claims 1–8, or a pharmaceutically acceptable salt or in vivo hydrolysable ester formed from an available carboxy or hydroxy group thereof.

* * * * *

UNITED STATES PATENT AND TRADEMARK OFFICE
CERTIFICATE OF CORRECTION

PATENT NO. : 6,855,719 B1
DATED : February 15, 2005
INVENTOR(S) : Andrew P. Thomas et al.

It is certified that error appears in the above-identified patent and that said Letters Patent is hereby corrected as shown below:

Column 56,
Line 11, change "$C_{1-3}$cycloalkyl" to -- $C_{3-8}$cycloalkyl --.

Signed and Sealed this

Seventh Day of February, 2006

JON W. DUDAS
*Director of the United States Patent and Trademark Office*